(12) United States Patent
Gruber et al.

(10) Patent No.: US 7,998,702 B2
(45) Date of Patent: Aug. 16, 2011

(54) MUTANT ARABINOSE PROMOTER FOR INDUCIBLE GENE EXPRESSION

(75) Inventors: Tanja Maria Gruber, Media, PA (US); Lisa L. Huang, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 500 days.

(21) Appl. No.: 12/212,271

(22) Filed: Sep. 17, 2008

(65) Prior Publication Data

US 2010/0068758 A1    Mar. 18, 2010

(51) Int. Cl.
  *C07H 21/04* (2006.01)
  *C12N 15/63* (2006.01)
  *C12N 15/00* (2006.01)
  *C12P 21/00* (2006.01)

(52) U.S. Cl. .................. 435/69.1; 435/71.1; 435/320.1; 536/24.1

(58) Field of Classification Search ........................ None
See application file for complete search history.

(56) References Cited

U.S. PATENT DOCUMENTS

| | | |
|---|---|---|
| 5,028,530 A | 7/1991 | Lai et al. |
| 5,648,244 A | 7/1997 | Kuliopulos et al. |
| 6,030,807 A | 2/2000 | DeLencastre et al. |
| 6,696,089 B2 | 2/2004 | Kabanov et al. |
| 6,815,426 B2 | 11/2004 | Scialdone et al. |
| 7,220,405 B2 | 5/2007 | Huang et al. |
| 7,285,264 B2 | 10/2007 | O'Brien et al. |
| 7,309,482 B2 | 12/2007 | Buseman-Williams et al. |
| 2002/0098524 A1 | 7/2002 | Murray et al. |
| 2003/0152976 A1 | 8/2003 | Janssen et al. |
| 2005/0226839 A1 | 10/2005 | Huang et al. |
| 2005/0249682 A1 | 11/2005 | Buseman-Williams et al. |
| 2006/0073111 A1 | 4/2006 | O'Brien et al. |
| 2006/0199206 A1 | 9/2006 | Wang et al. |
| 2007/0065387 A1 | 3/2007 | Beck et al. |
| 2007/0067924 A1 | 3/2007 | Beck et al. |
| 2007/0110686 A1 | 5/2007 | Lowe et al. |
| 2007/0141628 A1 | 6/2007 | Cunningham et al. |
| 2007/0141629 A1 | 6/2007 | Cunningham et al. |
| 2007/0196305 A1 | 8/2007 | Wang et al. |
| 2007/0249805 A1 | 10/2007 | Ittel et al. |
| 2007/0261775 A1 | 11/2007 | Cunningham et al. |
| 2007/0264720 A1 | 11/2007 | Cunningham et al. |
| 2008/0096245 A1 | 4/2008 | DeCarolis et al. |
| 2008/0096246 A1 | 4/2008 | DeCarolis et al. |
| 2008/0175798 A1 | 7/2008 | Beck et al. |
| 2008/0207872 A1 | 8/2008 | Cunningham et al. |
| 2008/0280810 A1 | 11/2008 | O'Brien et al. |

FOREIGN PATENT DOCUMENTS

| | | |
|---|---|---|
| WO | WO0179479 | 10/2001 |
| WO | WO04000257 | 12/2003 |
| WO | WO2004048399 | 6/2004 |

OTHER PUBLICATIONS

Gavit, P. and Better, M., J. Biotechnol., 79:127-136 (2000).
Szoka et al., DNA, 5(1):11-20 (1986).
Thornberry et al., J. Biol. Chem., 272:17907-17911 (1997).
Tyas et al., EMBO Reports, 1(3):266-270 (2000).
Horwitz et al., Gene 14:309-319 (1981).
Lin et al., Gene 34:111-122 (1985).
Lin et al., Gene 34:123-128 (1985).
Lin et al., Gene 34:129-134 (1985).
Schleif, R., Trends in Genet. 16(12):559-565 (2000).
Guzman et al., J. Bacteriol. 177:4121-4130 (1995).
Deshpande, Mukund V., Appl. Biochem. Biotechno., 36:227-234 (1992).
Biochemistry, Voet, D. & Voet J. G., John Wiley & Sons, Inc., Hoboken, NJ, pp. 855-858; 1st Edition (1990).
The Following Applications Are Commonly Owned by Dupont and Are Reported Herein: U.S. Appl. No. 11/782,836, filed Jul. 25, 2007.

*Primary Examiner* — Michele Joike

(57) ABSTRACT

An L-arabinose inducible expression system comprising a mutant arabinose promoter. This system exhibits an increase in heterologous protein production upon induction with L-arabinose and comprises a mutant araB promoter and an AraC transcription binding region. This system retains the tight regulatory control characteristic of the wild type arabinose operon.

22 Claims, 5 Drawing Sheets

```
                              -35                                                      -10
wt    TTTTTATCCATAAGATTAGCGGATCCTACCTGACGCGTTTTTTATCGCAACTCTCTACTGTT    (SEQ ID NO: 1)
mut1  TTTTTATCCATAAGATTAGCGGATCGTACCTGACGCGTTTTTTATCGCAACTCTCTCGTGTT    (SEQ ID NO: 9)
mut2  TTTTTATCCATAAGATTAGCGGATCGTACCTGACGCGTTTTTTATCGCAACTCTCCTCTGCT    (SEQ ID NO: 10)
mut3  TTTTTATCCATAAGATTAGCGGATCGTACCTGACGCGTTTTTTATCGCAACTCTCAACCATT    (SEQ ID NO: 11)
mut4  TTTTTATCCATAAGATTAGCGGATCGTACCTGACGCGTTTTTTATCGCAACTCTCATGAATT    (SEQ ID NO: 12)
mut5  TTTTTATCCATAAGATTAGCGGATCGTACCTGACGCGTTTTTATCGCAACTCTCAACCTAT    (SEQ ID NO: 13)
mut6  TTTTTATCCATAAGATTAGCGGATCGTACCTGACGCGTTTTTATCGCAACTCTCATGCTAT    (SEQ ID NO: 14)
mut7  TTTTTATCCATAAGATTAGCGGATCGTACCTGACGCGTTTTTATCGCAACTCTCGTAACCT    (SEQ ID NO: 15)
mut8  TTTTTATCCATAAGATTAGCGGATCGTACCTGACGCGTTTTTATCGCAACTCTCCCAGAGT    (SEQ ID NO: 16)
      ******************** **** ************* **************

RBS
wt    TCTCCATACCCGTTTTTTGGGCTAACAGAGGAATTAACC
mut1  TCTCCATACCCGTTTTTTGGGCTAACAGAGGAGAATTAACC
mut2  TCTCCATACCCGTTTTTTGGGCTAACAGAGGAGAATTAACC
mut3  TCTCCATACCCGTTTTTTGGGCTAACAG--AGGATTAAC-
mut4  TCTCCATACCCGTTTTTTGGGCTAACAG---AAATTACC-
mut5  TCTCCATACCCGTTTTTTGGGCTAACAGAGGAGGAATTAACC
mut6  TCTCCATACCCGTTTTTTGGGCTAACAGAGGAGGAATTAC--
mut7  TCTCCATACCCGTTTTTTGGGCTAACAGAGGAGGAATTAACC
mut8  TCTCCATACCCGTTTTTTGGGCTAACAGGA-GAATTAA--
      ****************************            ****
```

```
                              -35                                         -10
GFP B1 (SEQ ID NO: 17)  CTGACGCTTTTTATCGCAACTCTCCGTATATTCTCCATACCCGTTTTTG
GFP M1 (SEQ ID NO: 18)  CTGACGCTTTTTATCGCAACTCTCCTCTTGCTTTTCTCCATACCCGTTTTTG
GFP M2 (SEQ ID NO: 19)  CTGACGCTTTTTATCGCAACTCTCCATAGCCTTCTCCATACCCGTTTTTG
GFP M3 (SEQ ID NO: 20)  CTGACGCTTTTTATCGCAACTCTCCTAAACTTTCTCCATACCCGTTTTTG
wt     (SEQ ID NO:  1)  CTGACGCTTTTTATCGCAACTCTCTACTGTTTCTCCATACCCGTTTTTG

RBS
GFP B1  GGCTAACAGGAGGAATTAACCATGGTACCTGACGGCTTTTTATCGCAACTC
GFP M1  GGCTAACAGGAGGAATTAACC---------------------------------
GFP M2  GGCTAACAGGAGGAATTAACCATGGTACCTGACGGCTTTTTATCGCAACTC
GFP M3  GGCTAACAGGAGGAATTAACC---------------------------------
GFP wt  GGCTAACAGGAGGAATTAACC---------------------------------

GFP B1  TCTCAATATTCTCCATACCCGTTTTTGG-CTAACAG---AAATACC
GFP M1  -----------------------------------------------
GFP M2  TCGATCTTTTCTCCATACCCGTTTTTGGGCTAACAGGAGGAATTAAC
GFP M3  -----------------------------------------------
GFP wt  -----------------------------------------------

GFP B1  TTTTTATCCATAAGATTAGCGGATCGTAC
GFP M1  TTTTTATCCATAAGATTAGCGGATCGTAC
GFP M2  TTTTTATCCATAAGATTAGCGGATCGTAC
GFP M3  TTTTTATCCATAAGATTAGCGGATCCTAC
wt      TTTTTATCCATAAGATTAGCGGATCCTAC
```

| GFP_B1 | (SEQ ID NO. 17) | TTTTTATCCATAAGATTAGCGGATCGTACCTGACGCTTTTTATCGCAACTCTCCGTATAT |
| GFP_ara1B | (SEQ ID NO. 22) | TTTTTATCCATAAGATTAGCGGATCGTACCTGACGCTTTTTATCGCAACTCTCCGTATAT |
| GFP_ara4a | (SEQ ID NO. 23) | TTTTTATCCATAAGATTAGCGGATCGTACCTGACGCTTTTTATCGCAACTCTCTACTGTT |
| GFP_ara5a | (SEQ ID NO. 24) | TTTTTATCCATAAGATTAGCGGATCGTACCTGACGCTTTTTATCGCAACTCTCCGTATAT |
| GFP_ara8a | (SEQ ID NO. 25) | TTTTTATCCATAAGATTAGCGGATCGTACCTGACGCTTTTTATCGCAACTCTCATAGCCT |
| Consensus | (SEQ ID NO. 2) | TTTTTATCCATAAGATTAGCGGATCNTACCTGACGCTTTTTATCGCAACTCTCNNNNNNT |

-35                                              -10

| GFP_B1 | TCTCCATACCCGTTTTTTGGGCTAACAGAGGAGAATTAACCATGGTACCTGACGCTTTTTA |
| GFP_ara1B | TCTCCATACCCGTTTTTTGGGCTAACAGAGGAGAATTAACCATCGTACCTGACGCTTTTTA |
| GFP_ara4a | TCTCCATACCCGTTTTTTGGGCTAACAGAGGAGAATTAACCATGGTACCTGACGCTTTTTA |
| GFP_ara5a | TCTCCATACCCGTTTTTTGGGCTAACAGAGGAGAATTAACCATGGTACCTGACGCTTTTTA |
| GFP_ara8a | TCTCCATACCCGTTTTTTGGGCTAACAGAGGAGAATTAACCATGGTACCTGACGCTTTTTA |
| Consensus | TCTCCATACCCGTTTTTTGGGCTAACAGAGGAGAATTAACCATNGTACCTGACGCTTTTTA |

RBS                                       -35

| GFP_B1 | TCGCAACTCTCTCAATATTCTCCATACCCGTTTTTTGGCTAACAGAGAAATACC |
| GFP_ara1B | TCGCAACTCTCTCAATATTCTCCATACCCGTTTTTTGGCTAACAGAGAAATACC |
| GFP_ara4a | TCGCAACTCTCTCAATATTCTCCATACCCGTTTTTTGGCTAACAGAGAAATACC |
| GFP_ara5a | TCGCAACTCTCTCAATATTCTCCATACCCGTTTTTTGGCTAACAGAGAAATACC |
| GFP_ara8a | TCGCAACTCTCTGATCTTTCTCCATACCCGTTTTTTGGCTAACAGAGAAATCAT |
| GFP_ara8a | TCGCAACTCTCNNNNTNTTCTCCATACCCGTTTTTTGGCTAACAGAGAAATNNN |

SEQUENCE LISTING

```
<160> NUMBER OF SEQ ID NOS: 270

<210> SEQ ID NO 1
<211> LENGTH: 100
<212> TYPE: DNA
<213> ORGANISM: artificial sequence
<220> FEATURE:
<223> OTHER INFORMATION: synthetic construct

<400> SEQUENCE: 1
tttttatcca taagattagc ggatcctacc tgacgctttt tatcgcaact ctctactgtt      60
tctccatacc cgtttttttgg gctaacagga ggaattaacc                          100

<210> SEQ ID NO 2
<211> LENGTH: 172
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (26)..(26)
<223> OTHER INFORMATION: n  = c or g
<220> FEATURE:
<221> NAME/KEY: misc_feature
<222> LOCATION: (54)..(54)
<223> OTHER INFORMATION: n  = a, c or t
<220> FEATURE:
<221> NAME/KEY: misc_feature
<222> LOCATION: (55)..(55)
<223> OTHER INFORMATION: n  = a, g or t
<220> FEATURE:
<221> NAME/KEY: misc_feature
<222> LOCATION: (56)..(56)
<223> OTHER INFORMATION: n  = a, c or t
<220> FEATURE:
<221> NAME/KEY: misc_feature
<222> LOCATION: (57)..(57)
<223> OTHER INFORMATION: n  = a, g or t
<220> FEATURE:
<221> NAME/KEY: misc_feature
<222> LOCATION: (58)..(58)
<223> OTHER INFORMATION: n  = t, g or c
<220> FEATURE:
<221> NAME/KEY: misc_feature
<222> LOCATION: (59)..(59)
<223> OTHER INFORMATION: n  = a, c or t
<220> FEATURE:
<221> NAME/KEY: misc_feature
```

```
<222> LOCATION: (103)..(103)
<223> OTHER INFORMATION: n = g or c
<220> FEATURE:
<221> NAME/KEY: misc_feature
<222> LOCATION: (132)..(132)
<223> OTHER INFORMATION: n = t or g
<220> FEATURE:
<221> NAME/KEY: misc_feature
<222> LOCATION: (133)..(133)
<223> OTHER INFORMATION: n = a or c
<220> FEATURE:
<221> NAME/KEY: misc_feature
<222> LOCATION: (134)..(134)
<223> OTHER INFORMATION: n = a or t
<220> FEATURE:
<221> NAME/KEY: misc_feature
<222> LOCATION: (135)..(135)
<223> OTHER INFORMATION: n = a or c
<220> FEATURE:
<221> NAME/KEY: misc_feature
<222> LOCATION: (137)..(137)
<223> OTHER INFORMATION: n = a or t
<220> FEATURE:
<221> NAME/KEY: misc_feature
<222> LOCATION: (170)..(170)
<223> OTHER INFORMATION: n = a or c
<220> FEATURE:
<221> NAME/KEY: misc_feature
<222> LOCATION: (171)..(171)
<223> OTHER INFORMATION: n = a or c
<220> FEATURE:
<221> NAME/KEY: misc_feature
<222> LOCATION: (172)..(172)
<223> OTHER INFORMATION: n = c or t

<400> SEQUENCE: 2
tttttatcca taagattagc ggatcntacc tgacgctttt tatcgcaact ctcnnnnnnt      60
tctccatacc cgttttttgg gctaacagga ggaattaacc atngtacctg acgcttttta     120
tcgcaactct cnnnntnttc tccatacccg ttttttggct aacagaaatn nn             172

<210> SEQ ID NO 3
<211> LENGTH: 82
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (33)..(38)
<223> OTHER INFORMATION: n is a, c, g, or t

<400> SEQUENCE: 3
gatcctacct gacgcttttt atcgcaactc tcnnnnnntt ctccataccc gttttttggg      60
ctaacaggag gaattaacca tg                                              82

<210> SEQ ID NO 4
<211> LENGTH: 78
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (45)..(50)
<223> OTHER INFORMATION: n is a, c, g, or t

<400> SEQUENCE: 4
catggttaat tcctcctgtt agcccaaaaa acgggtatgg agaannnnnn gagagttgcg      60
ataaaaagcg tcaggtag                                                   78
```

<210> SEQ ID NO 5
<211> LENGTH: 4092
<212> TYPE: DNA
<213> ORGANISM: artificial sequence
<220> FEATURE:
<223> OTHER INFORMATION: vector pBAD.HisB

<400> SEQUENCE: 5

| | | | | | | |
|---|---|---|---|---|---|---|
| aagaaaccaa | ttgtccatat | tgcatcagac | attgccgtca | ctgcgtcttt | tactggctct | 60 |
| tctcgctaac | caaaccggta | accccgctta | ttaaaagcat | tctgtaacaa | agcgggacca | 120 |
| aagccatgac | aaaaacgcgt | aacaaaagtg | tctataatca | cggcagaaaa | gtccacattg | 180 |
| attatttgca | cggcgtcaca | ctttgctatg | ccatagcatt | tttatccata | agattagcgg | 240 |
| atcctacctg | acgctttta | tcgcaactct | ctactgtttc | tccatacccg | ttttttgggc | 300 |
| taacaggagg | aattaaccat | gggggttct | catcatcatc | atcatcatgg | tatggctagc | 360 |
| atgactggtg | gacagcaaat | gggtcgggat | ctgtacgacg | atgacgataa | ggatccgagc | 420 |
| tcgagatctg | cagctggtac | catatgggaa | ttcgaagctt | ggctgttttg | gcggatgaga | 480 |
| gaagattttc | agcctgatac | agattaaatc | agaacgcaga | agcggtctga | taaacagaa | 540 |
| tttgcctggc | ggcagtagcg | cggtggtccc | acctgacccc | atgccgaact | cagaagtgaa | 600 |
| acgccgtagc | gccgatggta | gtgtggggtc | tccccatgcg | agagtaggga | actgccaggc | 660 |
| atcaaataaa | acgaaaggct | cagtcgaaag | actgggcctt | tcgttttatc | tgttgtttgt | 720 |
| cggtgaacgc | tctcctgagt | aggacaaatc | cgccgggagc | ggatttgaac | gttgcgaagc | 780 |
| aacggcccgg | agggtggcgg | gcaggacgcc | cgccataaac | tgccaggcat | caaattaagc | 840 |
| agaaggccat | cctgacggat | ggccttttg | cgtttctaca | aactcttttg | tttatttttc | 900 |
| taaatacatt | caaatatgta | tccgctcatg | agacaataac | cctgataaat | gcttcaataa | 960 |
| tattgaaaaa | ggaagagtat | gagtattcaa | catttccgtg | tcgcccttat | tcccttttt | 1020 |
| gcggcatttt | gccttcctgt | ttttgctcac | ccagaaacgc | tggtgaaagt | aaaagatgct | 1080 |
| gaagatcagt | tgggtgcacg | agtgggttac | atcgaactgg | atctcaacag | cggtaagatc | 1140 |
| cttgagagtt | ttcgccccga | agaacgtttt | ccaatgatga | gcactttaa | agttctgcta | 1200 |
| tgtggcgcgg | tattatcccg | tgttgacgcc | gggcaagagc | aactcggtcg | ccgcatacac | 1260 |
| tattctcaga | atgacttggt | tgagtactca | ccagtcacag | aaaagcatct | tacggatggc | 1320 |
| atgacagtaa | gagaattatg | cagtgctgcc | ataaccatga | gtgataacac | tgcggccaac | 1380 |
| ttacttctga | caacgatcgg | aggaccgaag | gagctaaccg | cttttttgca | caacatgggg | 1440 |
| gatcatgtaa | ctcgccttga | tcgttgggaa | ccggagctga | atgaagccat | accaaacgac | 1500 |
| gagcgtgaca | ccacgatgcc | tgtagcaatg | gcaacaacgt | tgcgcaaact | attaactggc | 1560 |
| gaactactta | ctctagcttc | ccggcaacaa | ttaatagact | ggatggaggc | ggataaagtt | 1620 |
| gcaggaccac | ttctgcgctc | ggcccttccg | gctggctggt | ttattgctga | taaatctgga | 1680 |
| gccggtgagc | gtgggtctcg | cggtatcatt | gcagcactgg | ggccagatgg | taagccctcc | 1740 |
| cgtatcgtag | ttatctacac | gacggggagt | caggcaacta | tggatgaacg | aaatagacag | 1800 |
| atcgctgaga | taggtgcctc | actgattaag | cattggtaac | tgtcagacca | agtttactca | 1860 |
| tatatacttt | agattgattt | aaaacttcat | ttttaattta | aaaggatcta | ggtgaagatc | 1920 |
| cttttgata | atctcatgac | caaaatccct | taacgtgagt | tttcgttcca | ctgagcgtca | 1980 |
| gaccccgtag | aaaagatcaa | aggatcttct | tgagatcctt | ttttctgcg | cgtaatctgc | 2040 |
| tgcttgcaaa | caaaaaaacc | accgctacca | gcggtggttt | gtttgccgga | tcaagagcta | 2100 |
| ccaactcttt | ttccgaaggt | aactggcttc | agcagagcgc | agataccaaa | tactgtcctt | 2160 |

| | |
|---|---|
| ctagtgtagc cgtagttagg ccaccacttc aagaactctg tagcaccgcc tacatacctc | 2220 |
| gctctgctaa tcctgttacc agtggctgct gccagtggcg ataagtcgtg tcttaccggg | 2280 |
| ttggactcaa gacgatagtt accggataag gcgcagcggt cgggctgaac gggggggttcg | 2340 |
| tgcacacagc ccagcttgga gcgaacgacc tacaccgaac tgagatacct acagcgtgag | 2400 |
| ctatgagaaa gcgccacgct tcccgaaggg agaaaggcgg acaggtatcc ggtaagcggc | 2460 |
| agggtcggaa caggagagcg cacgagggag cttccagggg gaaacgcctg gtatctttat | 2520 |
| agtcctgtcg ggtttcgcca cctctgactt gagcgtcgat ttttgtgatg ctcgtcaggg | 2580 |
| gggcggagcc tatggaaaaa cgccagcaac gcggcctttt tacggttcct ggccttttgc | 2640 |
| tggccttttg ctcacatgtt ctttcctgcg ttatcccctg attctgtgga taaccgtatt | 2700 |
| accgcctttg agtgagctga taccgctcgc cgcagccgaa cgaccgagcg cagcgagtca | 2760 |
| gtgagcgagg aagcggaaga gcgcctgatg cggtattttc tccttacgca tctgtgcggt | 2820 |
| atttcacacc gcatatggtg cactctcagt acaatctgct ctgatgccgc atagttaagc | 2880 |
| cagtatacac tccgctatcg ctacgtgact gggtcatggc tgcgccccga cacccgccaa | 2940 |
| cacccgctga cgcgccctga cgggcttgtc tgctcccggc atccgcttac agacaagctg | 3000 |
| tgaccgtctc cgggagctgc atgtgtcaga ggttttcacc gtcatcaccg aaacgcgcga | 3060 |
| ggcagcagat caattcgcgc gcgaaggcga agcggcatgc ataatgtgcc tgtcaaatgg | 3120 |
| acgaagcagg gattctgcaa accctatgct actccgtcaa gccgtcaatt gtctgattcg | 3180 |
| ttaccaatta tgacaacttg acggctacat cattcacttt ttcttcacaa ccggcacgga | 3240 |
| actcgctcgg gctggccccg gtgcattttt taaatacccg cgagaaatag agttgatcgt | 3300 |
| caaaaccaac attgcgaccg acggtggcga taggcatccg ggtggtgctc aaaagcagct | 3360 |
| tcgcctggct gatacgttgg tcctcgcgcc agcttaagac gctaatccct aactgctggc | 3420 |
| ggaaaagatg tgacagacgc gacggcgaca agcaaacatg ctgtgcgacg ctggcgatat | 3480 |
| caaaattgct gtctgccagg tgatcgctga tgtactgaca agcctcgcgt acccgattat | 3540 |
| ccatcggtgg atggagcgac tcgttaatcg cttccatgcg ccgcagtaac aattgctcaa | 3600 |
| gcagatttat cgccagcagc tccgaatagc gcccttcccc ttgcccggcg ttaatgattt | 3660 |
| gcccaaacag gtcgctgaaa tgcggctggt gcgcttcatc cgggcgaaag aaccccgtat | 3720 |
| tggcaaatat tgacggccag ttaagccatt catgccagta ggcgcgcgga cgaaagtaaa | 3780 |
| cccactggtg ataccattcg cgagcctccg gatgacgacc gtagtgatga atctctcctg | 3840 |
| gcgggaacag caaaatatca cccggtcggc aaacaaattc tcgtccctga ttttcacca | 3900 |
| ccccctgacc gcgaatggtg agattgagaa tataaccttt cattcccagc ggtcggtcga | 3960 |
| taaaaaaatc gagataaccg ttggcctcaa tcggcgttaa accgccacc agatgggcat | 4020 |
| taaacgagta tcccggcagc aggggatcat tttgcgcttc agccatactt ttcatactcc | 4080 |
| cgccattcag ag | 4092 |

<210> SEQ ID NO 6
<211> LENGTH: 720
<212> TYPE: DNA
<213> ORGANISM: Aequorea coerulescens
<220> FEATURE:
<221> NAME/KEY: CDS
<222> LOCATION: (1)..(720)

<400> SEQUENCE: 6

| | |
|---|---|
| atg gtg agc aag ggc gcc gag ctg ttc acc ggc atc gtg ccc atc ctg<br>Met Val Ser Lys Gly Ala Glu Leu Phe Thr Gly Ile Val Pro Ile Leu | 48 |

```
                1               5                    10                    15
atc gag ctg aat ggc gat gtg aat ggc cac aag ttc agc gtg agc ggc      96
Ile Glu Leu Asn Gly Asp Val Asn Gly His Lys Phe Ser Val Ser Gly
                    20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
                35                  40                  45 tgc acc acc ggc aag ctg cct gtg ccc tgg ccc acc ctg gtg acc acc     192
Cys Thr Thr Gly Lys Leu Pro Val Pro Trp Pro Thr Leu Val Thr Thr
 50                  55                  60 ctg agc tac ggc gtg cag tgc ttc tca cgc tac ccc gat cac atg aag     240
Leu Ser Tyr Gly Val Gln Cys Phe Ser Arg Tyr Pro Asp His Met Lys
 65                  70                  75                  80 cag cac gac ttc ttc aag agc gcc atg cct gag ggc tac atc cag gag     288
Gln His Asp Phe Phe Lys Ser Ala Met Pro Glu Gly Tyr Ile Gln Glu
                    85                  90                  95 cgc acc atc ttc ttc gag gat gac ggc aac tac aag tcg cgc gcc gag     336
Arg Thr Ile Phe Phe Glu Asp Asp Gly Asn Tyr Lys Ser Arg Ala Glu
                100                 105                 110 gtg aag ttc gag ggc gat acc ctg gtg aat cgc atc gag ctg acc ggc     384
Val Lys Phe Glu Gly Asp Thr Leu Val Asn Arg Ile Glu Leu Thr Gly
            115                 120                 125 acc gat ttc aag gag gat ggc aac atc ctg ggc aat aag atg gag tac     432
Thr Asp Phe Lys Glu Asp Gly Asn Ile Leu Gly Asn Lys Met Glu Tyr
130                 135                 140 aac tac aac gcc cac aat gtg tac atc atg acc gac aag gcc aag aat     480
Asn Tyr Asn Ala His Asn Val Tyr Ile Met Thr Asp Lys Ala Lys Asn
145                 150                 155                 160 ggc atc aag gtg aac ttc aag atc cgc cac aac atc gag gat ggc agc     528
Gly Ile Lys Val Asn Phe Lys Ile Arg His Asn Ile Glu Asp Gly Ser
                165                 170                 175 gtg cag ctg gcc gac cac tac cag cag aat acc ccc atc ggc gat ggc     576
Val Gln Leu Ala Asp His Tyr Gln Gln Asn Thr Pro Ile Gly Asp Gly
            180                 185                 190 cct gtg ctg ctg ccc gat aac cac tac ctg tcc acc cag agc gcc ctg     624
Pro Val Leu Leu Pro Asp Asn His Tyr Leu Ser Thr Gln Ser Ala Leu
            195                 200                 205 tcc aag gac ccc aac gag aag cgc gat cac atg atc tac ttc ggc ttc     672
Ser Lys Asp Pro Asn Glu Lys Arg Asp His Met Ile Tyr Phe Gly Phe
210                 215                 220 gtg acc gcc gcc gcc atc acc cac ggc atg gat gag ctg tac aag tga    720
Val Thr Ala Ala Ala Ile Thr His Gly Met Asp Glu Leu Tyr Lys
225                 230                 235

<210> SEQ ID NO 7
<211> LENGTH: 239
<212> TYPE: PRT
<213> ORGANISM: Aequorea coerulescens

<400> SEQUENCE: 7

Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80
```

```
Gln His Asp Phe Phe Lys Ser Ala Met Pro Glu Gly Tyr Ile Gln Glu
                 85                  90                  95
Arg Thr Ile Phe Phe Glu Asp Asp Gly Asn Tyr Lys Ser Arg Ala Glu
            100                 105                 110
Val Lys Phe Glu Gly Asp Thr Leu Val Asn Arg Ile Glu Leu Thr Gly
        115                 120                 125
Thr Asp Phe Lys Glu Asp Gly Asn Ile Leu Gly Asn Lys Met Glu Tyr
130                 135                 140
Asn Tyr Asn Ala His Asn Val Tyr Ile Met Thr Asp Lys Ala Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Ile Tyr Phe Gly Phe
210                 215                 220
Val Thr Ala Ala Ala Ile Thr His Gly Met Asp Glu Leu Tyr Lys
225                 230                 235
```

<210> SEQ ID NO 8
<211> LENGTH: 4092
<212> TYPE: DNA
<213> ORGANISM: artificial sequence
<220> FEATURE:
<223> OTHER INFORMATION: vector pBAD.GFP

<400> SEQUENCE: 8

| | | |
|---|---|---|
| aagaaaccaa ttgtccatat tgcatcagac attgccgtca ctgcgtcttt tactggctct | 60 |
| tctcgctaac caaaccggta accccgctta ttaaaagcat tctgtaacaa agcgggacca | 120 |
| aagccatgac aaaaacgcgt aacaaaagtg tctataatca cggcagaaaa gtccacattg | 180 |
| attatttgca cggcgtcaca ctttgctatg ccatagcatt tttatccata agattagcgg | 240 |
| atcctacctg acgcttttta tcgcaactct ctactgtttc tccatacccg ttttttgggc | 300 |
| taacaggagg aattaaccat ggggggttct catcatcatc atcatcatgg tatggctagc | 360 |
| atgactggtg gacagcaaat gggtcgggat ctgtacgacg atgacgataa ggatccgagc | 420 |
| tcgagatctg cagctggtac catatgggaa ttcgaagctt ggctgttttg gcggatgaga | 480 |
| gaagattttc agcctgatac agattaaatc agaacgcaga agcggtctga taaaacagaa | 540 |
| tttgcctggc ggcagtagcg cggtggtccc acctgacccc atgccgaact cagaagtgaa | 600 |
| acgccgtagc gccgatggta gtgtgggtc tccccatgcg agagtaggga actgccaggc | 660 |
| atcaaataaa acgaaaggct cagtcgaaag actgggcctt tcgttttatc tgttgtttgt | 720 |
| cggtgaacgc tctcctgagt aggacaaatc cgccgggagc ggatttgaac gttgcgaagc | 780 |
| aacggcccgg agggtggcgg gcaggacgcc cgccataaac tgccaggcat caaattaagc | 840 |
| agaaggccat cctgacggat ggcctttttg cgtttctaca aactcttttg tttatttttc | 900 |
| taaatacatt caaatatgta tccgctcatg agacaataac cctgataaat gcttcaataa | 960 |
| tattgaaaaa ggaagagtat gagtattcaa catttccgtg tcgcccttat tcccttttt | 1020 |
| gcggcatttt gccttcctgt ttttgctcac ccagaaacgc tggtgaaagt aaaagatgct | 1080 |
| gaagatcagt tgggtgcacg agtgggttac atcgaactgg atctcaacag cggtaagatc | 1140 |
| cttgagagtt ttcgccccga agaacgtttt ccaatgatga gcacttttaa agttctgcta | 1200 |

```
tgtggcgcgg tattatcccg tgttgacgcc gggcaagagc aactcggtcg ccgcatacac    1260
tattctcaga atgacttggt tgagtactca ccagtcacag aaaagcatct tacggatggc    1320
atgacagtaa gagaattatg cagtgctgcc ataaccatga gtgataacac tgcggccaac    1380
ttacttctga caacgatcgg aggaccgaag gagctaaccg cttttttgca caacatgggg    1440
gatcatgtaa ctcgccttga tcgttgggaa ccggagctga atgaagccat accaaacgac    1500
gagcgtgaca ccacgatgcc tgtagcaatg gcaacaacgt tgcgcaaact attaactggc    1560
gaactactta ctctagcttc ccggcaacaa ttaatagact ggatggaggc ggataaagtt    1620
gcaggaccac ttctgcgctc ggcccttccg gctggctggt ttattgctga taaatctgga    1680
gccggtgagc gtgggtctcg cggtatcatt gcagcactgg ggccagatgg taagccctcc    1740
cgtatcgtag ttatctacac gacggggagt caggcaacta tggatgaacg aaatagacag    1800
atcgctgaga taggtgcctc actgattaag cattggtaac tgtcagacca agtttactca    1860
tatatacttt agattgattt aaaacttcat ttttaattta aaaggatcta ggtgaagatc    1920
ctttttgata atctcatgac caaaatccct taacgtgagt tttcgttcca ctgagcgtca    1980
gaccccgtag aaaagatcaa aggatcttct tgagatcctt ttttctgcg cgtaatctgc    2040 tgcttgcaaa caaaaaaacc accgctacca gcggtggttt gtttgccgga tcaagagcta    2100
ccaactcttt ttccgaaggt aactggcttc agcagagcgc agataccaaa tactgtcctt    2160
ctagtgtagc cgtagttagg ccaccacttc aagaactctg tagcaccgcc tacatacctc    2220
gctctgctaa tcctgttacc agtggctgct gccagtggcg ataagtcgtg tcttaccggg    2280
ttggactcaa gacgatagtt accggataag gcgcagcggt cgggctgaac ggggggttcg    2340
tgcacacagc ccagcttgga gcgaacgacc tacaccgaac tgagatacct acagcgtgag    2400
ctatgagaaa gcgccacgct tcccgaaggg agaaaggcgg acaggtatcc ggtaagcggc    2460
agggtcggaa caggagagcg cacgagggag cttccagggg gaaacgcctg gtatctttat    2520
agtcctgtcg ggtttcgcca cctctgactt gagcgtcgat ttttgtgatg ctcgtcaggg    2580
gggcggagcc tatggaaaaa cgccagcaac gcggcctttt tacggttcct ggccttttgc    2640
tggccttttg ctcacatgtt ctttcctgcg ttatcccctg attctgtgga taaccgtatt    2700
accgcctttg agtgagctga taccgctcgc cgcagccgaa cgaccgagcg cagcgagtca    2760
gtgagcgagg aagcggaaga gcgcctgatg cggtattttc tccttacgca tctgtgcggt    2820
atttcacacc gcatatggtg cactctcagt acaatctgct ctgatgccgc atagttaagc    2880
cagtatacac tccgctatcg ctacgtgact gggtcatggc tgcgccccga cacccgccaa    2940
cacccgctga cgcgccctga cgggcttgtc tgctcccggc atccgcttac agacaagctg    3000
tgaccgtctc cgggagctgc atgtgtcaga ggttttcacc gtcatcaccg aaacgcgcga    3060
ggcagcagat caattcgcgc gcgaaggcga agcggcatgc ataatgtgcc tgtcaaatgg    3120
acgaagcagg gattctgcaa accctatgct actccgtcaa gccgtcaatt gtctgattcg    3180
ttaccaatta tgacaacttg acggctacat cattcacttt tcttcacaa ccggcacgga    3240 actcgctcgg gctggccccg gtgcattttt taaatacccg cgagaaatag agttgatcgt    3300 caaaccaac attgcgaccg acggtggcga taggcatccg ggtggtgctc aaaagcagct    3360
tcgcctggct gatacgttgg tcctcgcgcc agcttaagac gctaatccct aactgctggc    3420
ggaaaagatg tgacagacgc gacggcgaca agcaaacatg ctgtgcgacg ctggcgatat    3480
caaaattgct gtctgccagg tgatcgctga tgtactgaca agcctcgcgt acccgattat    3540
ccatcggtgg atggagcgac tcgttaatcg cttccatgcg ccgcagtaac aattgctcaa    3600
```

```
gcagatttat cgccagcagc tccgaatagc gcccttcccc ttgcccggcg ttaatgattt    3660
gcccaaacag gtcgctgaaa tgcggctggt gcgcttcatc cgggcgaaag aaccccgtat    3720
tggcaaatat tgacggccag ttaagccatt catgccagta ggcgcgcgga cgaaagtaaa    3780
cccactggtg ataccattcg cgagcctccg gatgacgacc gtagtgatga atctctcctg    3840
gcgggaacag caaaatatca cccggtcggc aaacaaattc tcgtccctga ttttcacca     3900 ccccctgacc gcgaatggtg agattgagaa tataaccttt cattcccagc ggtcggtcga    3960
taaaaaaatc gagataaccg ttggcctcaa tcggcgttaa acccgccacc agatgggcat    4020
taaacgagta tcccggcagc aggggatcat tttgcgcttc agccatactt ttcatactcc    4080
cgccattcag ag                                                        4092

<210> SEQ ID NO 9
<211> LENGTH: 100
<212> TYPE: DNA
<213> ORGANISM: artificial sequence
<220> FEATURE:
<223> OTHER INFORMATION: synthetic construct

<400> SEQUENCE: 9
tttttatcca taagattagc ggatcgtacc tgacgctttt tatcgcaact ctctcgtgtt     60
tctccatacc cgttttttgg gctaacagga ggaattaacc                          100

<210> SEQ ID NO 10
<211> LENGTH: 100
<212> TYPE: DNA
<213> ORGANISM: artificial sequence
<220> FEATURE:
<223> OTHER INFORMATION: synthetic construct

<400> SEQUENCE: 10
tttttatcca taagattagc ggatcgtacc tgacgctttt tatcgcaact ctcctctgct     60
tctccatacc cgttttttgg gctaacagga ggaattaacc                          100

<210> SEQ ID NO 11
<211> LENGTH: 97
<212> TYPE: DNA
<213> ORGANISM: artificial sequence
<220> FEATURE:
<223> OTHER INFORMATION: synthetic construct

<400> SEQUENCE: 11
tttttatcca taagattagc ggatcgtacc tgacgctttt tatcgcaact ctcaaccatt     60
tctccatacc cgttttttgg gctaacagag gattaac                              97

<210> SEQ ID NO 12
<211> LENGTH: 96
<212> TYPE: DNA
<213> ORGANISM: artificial sequence
<220> FEATURE:
<223> OTHER INFORMATION: synthetic construct

<400> SEQUENCE: 12
tttttatcca taagattagc ggatcgtacc tgacgctttt tatcgcaact ctcatgaatt     60
tctccatacc cgttttttgg gctaacagaa attacc                               96

<210> SEQ ID NO 13
<211> LENGTH: 100
<212> TYPE: DNA
<213> ORGANISM: artificial sequence
```

```
<220> FEATURE:
<223> OTHER INFORMATION: synthetic construct

<400> SEQUENCE: 13
tttttatcca taagattagc ggatcgtacc tgacgctttt tatcgcaact ctcaacctat      60
tctccatacc cgttttttgg gctaacagga ggaattaacc                           100

<210> SEQ ID NO 14
<211> LENGTH: 98
<212> TYPE: DNA
<213> ORGANISM: artificial sequence
<220> FEATURE:
<223> OTHER INFORMATION: synthetic construct

<400> SEQUENCE: 14
tttttatcca taagattagc ggatcgtacc tgacgctttt tatcgcaact ctcatgctat      60
tctccatacc cgttttttgg gctaacagga ggaattac                              98

<210> SEQ ID NO 15
<211> LENGTH: 100
<212> TYPE: DNA
<213> ORGANISM: artificial sequence
<220> FEATURE:
<223> OTHER INFORMATION: synthetic construct

<400> SEQUENCE: 15
tttttatcca taagattagc ggatcgtacc tgacgctttt tatcgcaact ctcgtaacct      60
tctccatacc cgttttttgg gctaacagga ggaattaacc                           100

<210> SEQ ID NO 16
<211> LENGTH: 97
<212> TYPE: DNA
<213> ORGANISM: artificial sequence
<220> FEATURE:
<223> OTHER INFORMATION: synthetic construct

<400> SEQUENCE: 16
tttttatcca taagattagc ggatcgtacc tgacgctttt tatcgcaact ctcccagagt      60
tctccatacc cgttttttgg gctaacagga gaattaa                               97

<210> SEQ ID NO 17
<211> LENGTH: 136
<212> TYPE: DNA
<213> ORGANISM: artificial sequence
<220> FEATURE:
<223> OTHER INFORMATION: synthetic construct

<400> SEQUENCE: 17
tttttatcgc aactctccgt atattctcca tacccgtttt ttgggctaac aggaggaatt      60
aaccatggta cctgacgctt tttatcgcaa ctctctcaat attctccata cccgtttttt     120
ggctaacaga aatacc                                                     136

<210> SEQ ID NO 18
<211> LENGTH: 64
<212> TYPE: DNA
<213> ORGANISM: artificial sequence
<220> FEATURE:
<223> OTHER INFORMATION: synthetic construct

<400> SEQUENCE: 18
tttttatcgc aactctcttg cttttctcca tacccgtttt ttgggctaac aggaggaatt      60
aacc                                                                   64
```

<210> SEQ ID NO 19
<211> LENGTH: 140
<212> TYPE: DNA
<213> ORGANISM: artificial sequence
<220> FEATURE:
<223> OTHER INFORMATION: synthetic construct

<400> SEQUENCE: 19
tttttatcgc aactctcata gccttctcca tacccgtttt ttgggctaac aggaggaatt    60
aaccatggta cctgacgctt tttatcgcaa ctctcgatct tttctccata cccgtttttt   120
gggctaacag gagaattaac                                               140

<210> SEQ ID NO 20
<211> LENGTH: 64
<212> TYPE: DNA
<213> ORGANISM: artificial sequence
<220> FEATURE:
<223> OTHER INFORMATION: synthetic construct

<400> SEQUENCE: 20
tttttatcgc aactctctaa actttctcca tacccgtttt ttgggctaac aggaggaatt    60
aacc                                                                64

<210> SEQ ID NO 21
<211> LENGTH: 11
<212> TYPE: PRT
<213> ORGANISM: artificial sequence
<220> FEATURE:
<223> OTHER INFORMATION: synthetic construct

<400> SEQUENCE: 21

Met Val Pro Asp Ala Phe Tyr Arg Asn Ser Leu
1               5                   10

<210> SEQ ID NO 22
<211> LENGTH: 172
<212> TYPE: DNA
<213> ORGANISM: artificial sequence
<220> FEATURE:
<223> OTHER INFORMATION: synthetic construct

<400> SEQUENCE: 22
tttttatcca taagattagc ggatcgtacc tgacgctttt tatcgcaact ctccgtatat    60
tctccatacc cgttttttgg gctaacagga ggaattaacc atcgtacctg acgcttttta   120
tcgcaactct ctcaatattc tccatacccg ttttttggct aacagaaata cc           172

<210> SEQ ID NO 23
<211> LENGTH: 172
<212> TYPE: DNA
<213> ORGANISM: artificial sequence
<220> FEATURE:
<223> OTHER INFORMATION: synthetic construct

<400> SEQUENCE: 23
tttttatcca taagattagc ggatcctacc tgacgctttt tatcgcaact ctctactgtt    60
tctccatacc cgttttttgg gctaacagga ggaattaacc atggtacctg acgcttttta   120
tcgcaactct ctcaatattc tccatacccg ttttttggct aacagaaata cc           172

<210> SEQ ID NO 24
<211> LENGTH: 172
<212> TYPE: DNA

<213> ORGANISM: artificial sequence
<220> FEATURE:
<223> OTHER INFORMATION: synthetic construct

<400> SEQUENCE: 24

```
tttttatcca taagattagc ggatcgtacc tgacgctttt tatcgcaact ctccgtatat    60
tctccatacc cgttttttgg gctaacagga ggaattaacc atggtacctg acgcttttta   120
tcgcaactct ctcaatattc tccatacccg ttttttggct aacagaaatc at           172
```

<210> SEQ ID NO 25
<211> LENGTH: 172
<212> TYPE: DNA
<213> ORGANISM: artificial sequence
<220> FEATURE:
<223> OTHER INFORMATION: synthetic construct

<400> SEQUENCE: 25

```
tttttatcca taagattagc ggatcgtacc tgacgctttt tatcgcaact ctcatagcct    60
tctccatacc cgttttttgg gctaacagga ggaattaacc atggtacctg acgcttttta   120
tcgcaactct cgatcttttc tccatacccg ttttttggct aacagaaata cc           172
```

<210> SEQ ID NO 26
<211> LENGTH: 927
<212> TYPE: DNA
<213> ORGANISM: Escherichia coli
<220> FEATURE:
<221> NAME/KEY: CDS
<222> LOCATION: (1)..(927)

<400> SEQUENCE: 26

```
atg caa tat gga caa ttg gtt tct tct ctg aat ggc ggg agt atg aaa    48
Met Gln Tyr Gly Gln Leu Val Ser Ser Leu Asn Gly Gly Ser Met Lys
1               5                   10                  15 agt atg gct gaa gcg caa aat gat ccc ctg ctg ccg gga tac tcg ttt    96
Ser Met Ala Glu Ala Gln Asn Asp Pro Leu Leu Pro Gly Tyr Ser Phe
            20                  25                  30 aat gcc cat ctg gtg gcg ggt tta acg ccg att gag gcc aac ggt tat   144
Asn Ala His Leu Val Ala Gly Leu Thr Pro Ile Glu Ala Asn Gly Tyr
        35                  40                  45 ctc gat ttt ttt atc gac cga ccg ctg gga atg aaa ggt tat att ctc   192
Leu Asp Phe Phe Ile Asp Arg Pro Leu Gly Met Lys Gly Tyr Ile Leu
    50                  55                  60 aat ctc acc att cgc ggt cag ggg gtg gtg aaa aat cag gga cga gaa   240
Asn Leu Thr Ile Arg Gly Gln Gly Val Val Lys Asn Gln Gly Arg Glu
65                  70                  75                  80 ttt gtt tgc cga ccg ggt gat att ttg ctg ttc ccg cca gga gag att   288
Phe Val Cys Arg Pro Gly Asp Ile Leu Leu Phe Pro Pro Gly Glu Ile
                85                  90                  95 cat cac tac ggt cgt cat ccg gag gct cgc gaa tgg tat cac cag tgg   336
His His Tyr Gly Arg His Pro Glu Ala Arg Glu Trp Tyr His Gln Trp
            100                 105                 110 gtt tac ttt cgt ccg cgc gcc tac tgg cat gaa tgg ctt aac tgg ccg   384
Val Tyr Phe Arg Pro Arg Ala Tyr Trp His Glu Trp Leu Asn Trp Pro
        115                 120                 125 tca ata ttt gcc aat acg ggt tc ttt cgc ccg gat gaa gcg cac cag   432
Ser Ile Phe Ala Asn Thr Gly Phe Phe Arg Pro Asp Glu Ala His Gln
    130                 135                 140 ccg cat ttc agc gac ctg ttt ggg caa atc att aac gcc ggg caa ggg   480
Pro His Phe Ser Asp Leu Phe Gly Gln Ile Ile Asn Ala Gly Gln Gly
145                 150                 155                 160 gaa ggg cgc tat tcg gag ctg ctg gcg ata aat ctg ctt gag caa ttg   528
Glu Gly Arg Tyr Ser Glu Leu Leu Ala Ile Asn Leu Leu Glu Gln Leu
```

-continued

```
                Glu Gly Arg Tyr Ser Glu Leu Leu Ala Ile Asn Leu Leu Glu Gln Leu
                            165                 170                 175 tta ctg cgg cgc atg gaa gcg att aac gag tcg ctc cat cca ccg atg         576
Leu Leu Arg Arg Met Glu Ala Ile Asn Glu Ser Leu His Pro Pro Met
            180                 185                 190 gat aat cgg gta cgc gag gct tgt cag tac atc agc gat cac ctg gca         624
Asp Asn Arg Val Arg Glu Ala Cys Gln Tyr Ile Ser Asp His Leu Ala
        195                 200                 205 gac agc aat ttt gat atc gcc agc gtc gca cag cat gtt tgc ttg tcg         672
Asp Ser Asn Phe Asp Ile Ala Ser Val Ala Gln His Val Cys Leu Ser
    210                 215                 220 ccg tcg cgt ctg tca cat ctt ttc cgc cag cag tta ggg att agc gtc         720
Pro Ser Arg Leu Ser His Leu Phe Arg Gln Gln Leu Gly Ile Ser Val
225                 230                 235                 240 tta agc tgg cgc gag gac caa cgt atc agc cag gcg aag ctg ctt ttg         768
Leu Ser Trp Arg Glu Asp Gln Arg Ile Ser Gln Ala Lys Leu Leu Leu
                245                 250                 255 agc acc acc cgg atg cct atc gcc acc gtc ggt cgc aat gtt ggt ttt         816
Ser Thr Thr Arg Met Pro Ile Ala Thr Val Gly Arg Asn Val Gly Phe
            260                 265                 270 gac gat caa ctc tat ttc tcg cgg gta ttt aaa aaa tgc acc ggg gcc         864
Asp Asp Gln Leu Tyr Phe Ser Arg Val Phe Lys Lys Cys Thr Gly Ala
        275                 280                 285 agc ccg agc gag ttc cgt gcc ggt tgt gaa gaa aaa gtg aat gat gta         912
Ser Pro Ser Glu Phe Arg Ala Gly Cys Glu Glu Lys Val Asn Asp Val
    290                 295                 300 gcc gtc aag ttg tca                                                      927
Ala Val Lys Leu Ser
305

<210> SEQ ID NO 27
<211> LENGTH: 309
<212> TYPE: PRT
<213> ORGANISM: Escherichia coli

<400> SEQUENCE: 27

Met Gln Tyr Gly Gln Leu Val Ser Ser Leu Asn Gly Gly Ser Met Lys
1               5                   10                  15

Ser Met Ala Glu Ala Gln Asn Asp Pro Leu Leu Pro Gly Tyr Ser Phe
            20                  25                  30

Asn Ala His Leu Val Ala Gly Leu Thr Pro Ile Glu Ala Asn Gly Tyr
        35                  40                  45

Leu Asp Phe Phe Ile Asp Arg Pro Leu Gly Met Lys Gly Tyr Ile Leu
    50                  55                  60

Asn Leu Thr Ile Arg Gly Gln Gly Val Val Lys Asn Gln Gly Arg Glu
65                  70                  75                  80

Phe Val Cys Arg Pro Gly Asp Ile Leu Leu Phe Pro Pro Gly Glu Ile
                85                  90                  95

His His Tyr Gly Arg His Pro Glu Ala Arg Glu Trp Tyr His Gln Trp
            100                 105                 110

Val Tyr Phe Arg Pro Arg Ala Tyr Trp His Glu Trp Leu Asn Trp Pro
        115                 120                 125

Ser Ile Phe Ala Asn Thr Gly Phe Phe Arg Pro Asp Glu Ala His Gln
    130                 135                 140

Pro His Phe Ser Asp Leu Phe Gly Gln Ile Ile Asn Ala Gly Gln Gly
145                 150                 155                 160

Glu Gly Arg Tyr Ser Glu Leu Leu Ala Ile Asn Leu Leu Glu Gln Leu
                165                 170                 175
```

```
Leu Leu Arg Arg Met Glu Ala Ile Asn Glu Ser Leu His Pro Pro Met
            180                 185                 190

Asp Asn Arg Val Arg Glu Ala Cys Gln Tyr Ile Ser Asp His Leu Ala
        195                 200                 205

Asp Ser Asn Phe Asp Ile Ala Ser Val Ala Gln His Val Cys Leu Ser
    210                 215                 220

Pro Ser Arg Leu Ser His Leu Phe Arg Gln Gln Leu Gly Ile Ser Val
225                 230                 235                 240

Leu Ser Trp Arg Glu Asp Gln Arg Ile Ser Gln Ala Lys Leu Leu Leu
                245                 250                 255

Ser Thr Thr Arg Met Pro Ile Ala Thr Val Gly Arg Asn Val Gly Phe
            260                 265                 270

Asp Asp Gln Leu Tyr Phe Ser Arg Val Phe Lys Lys Cys Thr Gly Ala
        275                 280                 285

Ser Pro Ser Glu Phe Arg Ala Gly Cys Glu Glu Lys Val Asn Asp Val
    290                 295                 300

Ala Val Lys Leu Ser
305

<210> SEQ ID NO 28
<211> LENGTH: 154
<212> TYPE: DNA
<213> ORGANISM: artificial sequence
<220> FEATURE:
<223> OTHER INFORMATION: synthetic construct

<400> SEQUENCE: 28
tgcctggcgg cagtagcgcg gtggtcccac ctgaccccat gccgaactca gaagtgaaac     60
gccgtagcgc cgatggtagt gtggggtctc cccatgcgag agtagggaac tgccaggcat    120
caaataaaac gaaaggctca gtcgaaagac tggg                                154

<210> SEQ ID NO 29
<211> LENGTH: 16
<212> TYPE: DNA
<213> ORGANISM: artificial sequence
<220> FEATURE:
<223> OTHER INFORMATION: synthetic construct

<400> SEQUENCE: 29
aaaccaattg tccata                                                     16

<210> SEQ ID NO 30
<211> LENGTH: 22
<212> TYPE: DNA
<213> ORGANISM: artificial sequence
<220> FEATURE:
<223> OTHER INFORMATION: synthetic construct

<400> SEQUENCE: 30
cggcagaaaa gtccacattg at                                              22

<210> SEQ ID NO 31
<211> LENGTH: 14
<212> TYPE: DNA
<213> ORGANISM: artificial sequence
<220> FEATURE:
<223> OTHER INFORMATION: synthetic construct

<400> SEQUENCE: 31
ttgctatgcc atag                                                       14
```

```
<210> SEQ ID NO 32
<211> LENGTH: 38
<212> TYPE: DNA
<213> ORGANISM: artificial sequence
<220> FEATURE:
<223> OTHER INFORMATION: synthetic construct

<400> SEQUENCE: 32
atagcatttt tatccataag attagcggat cctacctg                              38

<210> SEQ ID NO 33
<211> LENGTH: 214
<212> TYPE: DNA
<213> ORGANISM: artificial sequence
<220> FEATURE:
<223> OTHER INFORMATION: synthetic construct

<400> SEQUENCE: 33
aaaccaattg tccatattgc atcagacatt gccgtcactg cgtcttttac tggctcttct      60
cgctaaccaa accggtaacc ccgcttatta aaagcattct gtaacaaagc gggaccaaag     120
ccatgacaaa aacgcgtaac aaaagtgtct ataatcacgg cagaaaagtc cacattgatt     180
atttgcacgg cgtcacactt tgctatgcca taca                                 214

<210> SEQ ID NO 34
<211> LENGTH: 386
<212> TYPE: DNA
<213> ORGANISM: artificial sequence
<220> FEATURE:
<223> OTHER INFORMATION: synthetic construct
<220> FEATURE:
<221> NAME/KEY: misc_feature
<222> LOCATION: (240)..(240)
<223> OTHER INFORMATION: n = c or g
<220> FEATURE:
<221> NAME/KEY: misc_feature
<222> LOCATION: (268)..(268)
<223> OTHER INFORMATION: n = a, c or t
<220> FEATURE:
<221> NAME/KEY: misc_feature
<222> LOCATION: (269)..(269)
<223> OTHER INFORMATION: n = a, g or t
<220> FEATURE:
<221> NAME/KEY: misc_feature
<222> LOCATION: (270)..(270)
<223> OTHER INFORMATION: n = a, c or t
<220> FEATURE:
<221> NAME/KEY: misc_feature
<222> LOCATION: (271)..(271)
<223> OTHER INFORMATION: n = a, g or t
<220> FEATURE:
<221> NAME/KEY: misc_feature
<222> LOCATION: (272)..(272)
<223> OTHER INFORMATION: n = t, c or g
<220> FEATURE:
<221> NAME/KEY: misc_feature
<222> LOCATION: (273)..(273)
<223> OTHER INFORMATION: n = a, c or t
<220> FEATURE:
<221> NAME/KEY: misc_feature
<222> LOCATION: (317)..(317)
<223> OTHER INFORMATION: n = g or c
<220> FEATURE:
<221> NAME/KEY: misc_feature
<222> LOCATION: (346)..(346)
<223> OTHER INFORMATION: n = t or g
<220> FEATURE:
<221> NAME/KEY: misc_feature
<222> LOCATION: (347)..(347)
<223> OTHER INFORMATION: n = a or c
<220> FEATURE:
<221> NAME/KEY: misc_feature
<222> LOCATION: (348)..(348)
<223> OTHER INFORMATION: n = a or t
```

```
<220> FEATURE:
<221> NAME/KEY: misc_feature
<222> LOCATION: (349)..(349)
<223> OTHER INFORMATION: n = a or c
<220> FEATURE:
<221> NAME/KEY: misc_feature
<222> LOCATION: (351)..(351)
<223> OTHER INFORMATION: n = a or t
<220> FEATURE:
<221> NAME/KEY: misc_feature
<222> LOCATION: (384)..(384)
<223> OTHER INFORMATION: n = a or c
<220> FEATURE:
<221> NAME/KEY: misc_feature
<222> LOCATION: (385)..(385)
<223> OTHER INFORMATION: n = a or c
<220> FEATURE:
<221> NAME/KEY: misc_feature
<222> LOCATION: (386)..(386)
<223> OTHER INFORMATION: n = c or t

<400> SEQUENCE: 34
aaaccaattg tccatattgc atcagacatt gccgtcactg cgtctttac tggctcttct      60 cgctaaccaa accggtaacc ccgcttatta aaagcattct gtaacaaagc gggaccaaag    120
ccatgacaaa aacgcgtaac aaaagtgtct ataatcacgg cagaaaagtc cacattgatt    180
atttgcacgg cgtcacactt tgctatgcca tacatttta tccataagat tagcggatcn    240
tacctgacgc ttttatcgc aactctcnnn nnnttctcca tacccgtttt ttgggctaac    300
aggaggaatt aaccatngta cctgacgctt tttatcgcaa ctctcnnnnt nttctccata    360 cccgttttt ggctaacaga aatnnn                                         386

<210> SEQ ID NO 35
<211> LENGTH: 386
<212> TYPE: DNA
<213> ORGANISM: artificial sequence
<220> FEATURE:
<223> OTHER INFORMATION: synthetic construct

<400> SEQUENCE: 35
aaaccaattg tccatattgc atcagacatt gccgtcactg cgtctttac tggctcttct      60 cgctaaccaa accggtaacc ccgcttatta aaagcattct gtaacaaagc gggaccaaag    120
ccatgacaaa aacgcgtaac aaaagtgtct ataatcacgg cagaaaagtc cacattgatt    180
atttgcacgg cgtcacactt tgctatgcca tacatttta tccataagat tagcggatcg    240
tacctgacgc ttttatcgc aactctccgt atattctcca tacccgtttt ttgggctaac    300
aggaggaatt aaccatggta cctgacgctt tttatcgcaa ctctctcaat attctccata    360 cccgttttt ggctaacaga aatacc                                         386

<210> SEQ ID NO 36
<211> LENGTH: 386
<212> TYPE: DNA
<213> ORGANISM: artificial sequence
<220> FEATURE:
<223> OTHER INFORMATION: synthetic construct

<400> SEQUENCE: 36
aaaccaattg tccatattgc atcagacatt gccgtcactg cgtctttac tggctcttct      60 cgctaaccaa accggtaacc ccgcttatta aaagcattct gtaacaaagc gggaccaaag    120
ccatgacaaa aacgcgtaac aaaagtgtct ataatcacgg cagaaaagtc cacattgatt    180
atttgcacgg cgtcacactt tgctatgcca tacatttta tccataagat tagcggatcg    240
tacctgacgc ttttatcgc aactctccgt atattctcca tacccgtttt ttgggctaac    300
```

```
aggaggaatt aaccatcgta cctgacgctt tttatcgcaa ctctctcaat attctccata    360 cccgttttt ggctaacaga aatacc                                          386

<210> SEQ ID NO 37
<211> LENGTH: 386
<212> TYPE: DNA
<213> ORGANISM: artificial sequence
<220> FEATURE:
<223> OTHER INFORMATION: synthetic construct

<400> SEQUENCE: 37
aaaccaattg tccatattgc atcagacatt gccgtcactg cgtctttac tggctcttct     60 cgctaaccaa accggtaacc ccgcttatta aaagcattct gtaacaaagc gggaccaaag    120
ccatgacaaa aacgcgtaac aaaagtgtct ataatcacgg cagaaaagtc cacattgatt   180
atttgcacgg cgtcacactt tgctatgcca tacattttta tccataagat tagcggatcc   240
tacctgacgc ttttatcgc aactctctac tgtttctcca tacccgtttt ttgggctaac    300
aggaggaatt aaccatggta cctgacgctt tttatcgcaa ctctctcaat attctccata   360 cccgttttt ggctaacaga aatacc                                          386

<210> SEQ ID NO 38
<211> LENGTH: 386
<212> TYPE: DNA
<213> ORGANISM: artificial sequence
<220> FEATURE:
<223> OTHER INFORMATION: synthetic construct

<400> SEQUENCE: 38
aaaccaattg tccatattgc atcagacatt gccgtcactg cgtctttac tggctcttct     60 cgctaaccaa accggtaacc ccgcttatta aaagcattct gtaacaaagc gggaccaaag    120
ccatgacaaa aacgcgtaac aaaagtgtct ataatcacgg cagaaaagtc cacattgatt   180
atttgcacgg cgtcacactt tgctatgcca tacattttta tccataagat tagcggatcg   240
tacctgacgc ttttatcgc aactctccgt atattctcca tacccgtttt ttgggctaac   300
aggaggaatt aaccatggta cctgacgctt tttatcgcaa ctctctcaat attctccata   360 cccgttttt ggctaacaga aatcat                                          386

<210> SEQ ID NO 39
<211> LENGTH: 386
<212> TYPE: DNA
<213> ORGANISM: artificial sequence
<220> FEATURE:
<223> OTHER INFORMATION: synthetic construct

<400> SEQUENCE: 39
aaaccaattg tccatattgc atcagacatt gccgtcactg cgtctttac tggctcttct     60 cgctaaccaa accggtaacc ccgcttatta aaagcattct gtaacaaagc gggaccaaag    120
ccatgacaaa aacgcgtaac aaaagtgtct ataatcacgg cagaaaagtc cacattgatt   180
atttgcacgg cgtcacactt tgctatgcca tacattttta tccataagat tagcggatcg   240
tacctgacgc ttttatcgc aactctcata gccttctcca tacccgtttt ttgggctaac    300
aggaggaatt aaccatggta cctgacgctt tttatcgcaa ctctcgatct tttctccata   360 cccgttttt ggctaacaga aatacc                                          386

<210> SEQ ID NO 40
<211> LENGTH: 26
```

```
<212> TYPE: DNA
<213> ORGANISM: artificial sequence
<220> FEATURE:
<223> OTHER INFORMATION: primer

<400> SEQUENCE: 40
gaggaattaa ccatcgtacc tgacgc                                          26

<210> SEQ ID NO 41
<211> LENGTH: 26
<212> TYPE: DNA
<213> ORGANISM: artificial sequence
<220> FEATURE:
<223> OTHER INFORMATION: primer

<400> SEQUENCE: 41
gcgtcaggta cgatggttaa ttcctc                                          26

<210> SEQ ID NO 42
<211> LENGTH: 31
<212> TYPE: DNA
<213> ORGANISM: artificial sequence
<220> FEATURE:
<223> OTHER INFORMATION: primer

<400> SEQUENCE: 42
ggctaacaga aatcatatgg tgagcaaggg c                                    31

<210> SEQ ID NO 43
<211> LENGTH: 31
<212> TYPE: DNA
<213> ORGANISM: artificial sequence
<220> FEATURE:
<223> OTHER INFORMATION: primer

<400> SEQUENCE: 43
gcccttgctc accatatgat ttctgttagc c                                    31

<210> SEQ ID NO 44
<211> LENGTH: 49
<212> TYPE: DNA
<213> ORGANISM: artificial sequence
<220> FEATURE:
<223> OTHER INFORMATION: primer

<400> SEQUENCE: 44
ccatacccgt tttttggcta acagaaatac catggtgagc aagggcgcc                 49

<210> SEQ ID NO 45
<211> LENGTH: 49
<212> TYPE: DNA
<213> ORGANISM: artificial sequence
<220> FEATURE:
<223> OTHER INFORMATION: primer

<400> SEQUENCE: 45
ggcgcccttg ctcaccatgg tatttctgtt agccaaaaaa cgggtatgg                 49

<210> SEQ ID NO 46
<211> LENGTH: 12
<212> TYPE: PRT
<213> ORGANISM: artificial sequence
<220> FEATURE:
<223> OTHER INFORMATION: Synthetic construct

<400> SEQUENCE: 46

Arg Val Pro Asn Lys Thr Val Thr Val Asp Gly Ala
```

```
1               5                   10

<210> SEQ ID NO 47
<211> LENGTH: 12
<212> TYPE: PRT
<213> ORGANISM: artificial sequence
<220> FEATURE:
<223> OTHER INFORMATION: Synthetic construct

<400> SEQUENCE: 47

Asp Arg His Lys Ser Lys Tyr Ser Ser Thr Lys Ser
1               5                   10

<210> SEQ ID NO 48
<211> LENGTH: 12
<212> TYPE: PRT
<213> ORGANISM: artificial sequence
<220> FEATURE:
<223> OTHER INFORMATION: Synthetic construct

<400> SEQUENCE: 48

Lys Asn Phe Pro Gln Gln Lys Glu Phe Pro Leu Ser
1               5                   10

<210> SEQ ID NO 49
<211> LENGTH: 12
<212> TYPE: PRT
<213> ORGANISM: artificial sequence
<220> FEATURE:
<223> OTHER INFORMATION: Synthetic construct

<400> SEQUENCE: 49

Gln Arg Asn Ser Pro Ala Met Ser Arg Arg Asp
1               5                   10

<210> SEQ ID NO 50
<211> LENGTH: 12
<212> TYPE: PRT
<213> ORGANISM: artificial sequence
<220> FEATURE:
<223> OTHER INFORMATION: Synthetic construct

<400> SEQUENCE: 50

Thr Arg Lys Pro Asn Met Pro His Gly Gln Tyr Leu
1               5                   10

<210> SEQ ID NO 51
<211> LENGTH: 12
<212> TYPE: PRT
<213> ORGANISM: artificial sequence
<220> FEATURE:
<223> OTHER INFORMATION: Synthetic construct

<400> SEQUENCE: 51

Lys Pro Pro His Leu Ala Lys Leu Pro Phe Thr Thr
1               5                   10

<210> SEQ ID NO 52
<211> LENGTH: 12
<212> TYPE: PRT
<213> ORGANISM: artificial sequence
<220> FEATURE:
<223> OTHER INFORMATION: Synthetic construct

<400> SEQUENCE: 52

Asn Lys Arg Pro Pro Thr Ser His Arg Ile His Ala
1               5                   10
```

<210> SEQ ID NO 53
<211> LENGTH: 12
<212> TYPE: PRT
<213> ORGANISM: artificial sequence
<220> FEATURE:
<223> OTHER INFORMATION: Synthetic construct

<400> SEQUENCE: 53

Asn Leu Pro Arg Tyr Gln Pro Pro Cys Lys Pro Leu
1               5                   10

<210> SEQ ID NO 54
<211> LENGTH: 12
<212> TYPE: PRT
<213> ORGANISM: artificial sequence
<220> FEATURE:
<223> OTHER INFORMATION: Synthetic construct

<400> SEQUENCE: 54

Arg Pro Pro Trp Lys Lys Pro Ile Pro Pro Ser Glu
1               5                   10

<210> SEQ ID NO 55
<211> LENGTH: 12
<212> TYPE: PRT
<213> ORGANISM: artificial sequence
<220> FEATURE:
<223> OTHER INFORMATION: Synthetic construct

<400> SEQUENCE: 55

Arg Gln Arg Pro Lys Asp His Phe Phe Ser Arg Pro
1               5                   10

<210> SEQ ID NO 56
<211> LENGTH: 12
<212> TYPE: PRT
<213> ORGANISM: artificial sequence
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 56

Ser Val Pro Asn Lys Xaa Val Thr Val Asp Gly Xaa
1               5                   10

<210> SEQ ID NO 57
<211> LENGTH: 12
<212> TYPE: PRT
<213> ORGANISM: artificial sequence
<220> FEATURE:
<223> OTHER INFORMATION: Synthetic construct

<400> SEQUENCE: 57

Thr Thr Lys Trp Arg His Arg Ala Pro Val Ser Pro
1               5                   10

<210> SEQ ID NO 58
<211> LENGTH: 12
<212> TYPE: PRT
<213> ORGANISM: artificial sequence
<220> FEATURE:
<223> OTHER INFORMATION: Synthetic construct

```
<400> SEQUENCE: 58

Trp Leu Gly Lys Asn Arg Ile Lys Pro Arg Ala Ser
1               5                   10

<210> SEQ ID NO 59
<211> LENGTH: 12
<212> TYPE: PRT
<213> ORGANISM: artificial sequence
<220> FEATURE:
<223> OTHER INFORMATION: Synthetic construct

<400> SEQUENCE: 59

Ser Asn Phe Lys Thr Pro Leu Pro Leu Thr Gln Ser
1               5                   10

<210> SEQ ID NO 60
<211> LENGTH: 12
<212> TYPE: PRT
<213> ORGANISM: artificial sequence
<220> FEATURE:
<223> OTHER INFORMATION: Synthetic construct

<400> SEQUENCE: 60

Ser Val Ser Val Gly Met Lys Pro Ser Pro Arg Pro
1               5                   10

<210> SEQ ID NO 61
<211> LENGTH: 7
<212> TYPE: PRT
<213> ORGANISM: artificial sequence
<220> FEATURE:
<223> OTHER INFORMATION: Synthetic construct

<400> SEQUENCE: 61

Asp Leu His Thr Val Tyr His
1               5

<210> SEQ ID NO 62
<211> LENGTH: 7
<212> TYPE: PRT
<213> ORGANISM: artificial sequence
<220> FEATURE:
<223> OTHER INFORMATION: Synthetic construct

<400> SEQUENCE: 62

His Ile Lys Pro Pro Thr Arg
1               5

<210> SEQ ID NO 63
<211> LENGTH: 7
<212> TYPE: PRT
<213> ORGANISM: artificial sequence
<220> FEATURE:
<223> OTHER INFORMATION: Synthetic construct

<400> SEQUENCE: 63

His Pro Val Trp Pro Ala Ile
1               5

<210> SEQ ID NO 64
<211> LENGTH: 7
<212> TYPE: PRT
<213> ORGANISM: artificial sequence
<220> FEATURE:
<223> OTHER INFORMATION: Synthetic construct

<400> SEQUENCE: 64
```

Met Pro Leu Tyr Tyr Leu Gln
1               5

<210> SEQ ID NO 65
<211> LENGTH: 26
<212> TYPE: PRT
<213> ORGANISM: artificial sequence
<220> FEATURE:
<223> OTHER INFORMATION: Synthetic construct

<400> SEQUENCE: 65

His Leu Thr Val Pro Trp Arg Gly Gly Ser Ala Val Pro Phe Tyr
1               5                   10                  15

Ser His Ser Gln Ile Thr Leu Pro Asn His
            20                  25

<210> SEQ ID NO 66
<211> LENGTH: 41
<212> TYPE: PRT
<213> ORGANISM: artificial sequence
<220> FEATURE:
<223> OTHER INFORMATION: Synthetic construct

<400> SEQUENCE: 66

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
        35                  40

<210> SEQ ID NO 67
<211> LENGTH: 7
<212> TYPE: PRT
<213> ORGANISM: artificial sequence
<220> FEATURE:
<223> OTHER INFORMATION: Synthetic construct

<400> SEQUENCE: 67

Lys His Pro Thr Tyr Arg Gln
1               5

<210> SEQ ID NO 68
<211> LENGTH: 7
<212> TYPE: PRT
<213> ORGANISM: artificial sequence
<220> FEATURE:
<223> OTHER INFORMATION: Synthetic construct

<400> SEQUENCE: 68

His Pro Met Ser Ala Pro Arg
1               5

<210> SEQ ID NO 69
<211> LENGTH: 7
<212> TYPE: PRT
<213> ORGANISM: artificial sequence
<220> FEATURE:
<223> OTHER INFORMATION: Synthetic construct

<400> SEQUENCE: 69

Met Pro Lys Tyr Tyr Leu Gln
1               5

<210> SEQ ID NO 70

```
<211> LENGTH: 7
<212> TYPE: PRT
<213> ORGANISM: artificial sequence
<220> FEATURE:
<223> OTHER INFORMATION: Synthetic construct

<400> SEQUENCE: 70

Met His Ala His Ser Ile Ala
1               5

<210> SEQ ID NO 71
<211> LENGTH: 12
<212> TYPE: PRT
<213> ORGANISM: artificial sequence
<220> FEATURE:
<223> OTHER INFORMATION: Synthetic construct

<400> SEQUENCE: 71

Ala Lys Pro Ile Ser Gln His Leu Gln Arg Gly Ser
1               5                   10

<210> SEQ ID NO 72
<211> LENGTH: 12
<212> TYPE: PRT
<213> ORGANISM: artificial sequence
<220> FEATURE:
<223> OTHER INFORMATION: Synthetic construct

<400> SEQUENCE: 72

Ala Pro Pro Thr Pro Ala Ala Ala Ser Ala Thr Thr
1               5                   10

<210> SEQ ID NO 73
<211> LENGTH: 12
<212> TYPE: PRT
<213> ORGANISM: artificial sequence
<220> FEATURE:
<223> OTHER INFORMATION: Synthetic construct

<400> SEQUENCE: 73

Asp Pro Thr Glu Gly Ala Arg Arg Thr Ile Met Thr
1               5                   10

<210> SEQ ID NO 74
<211> LENGTH: 12
<212> TYPE: PRT
<213> ORGANISM: artificial sequence
<220> FEATURE:
<223> OTHER INFORMATION: Synthetic construct

<400> SEQUENCE: 74

Leu Asp Thr Ser Phe Pro Pro Val Pro Phe His Ala
1               5                   10

<210> SEQ ID NO 75
<211> LENGTH: 12
<212> TYPE: PRT
<213> ORGANISM: artificial sequence
<220> FEATURE:
<223> OTHER INFORMATION: Synthetic construct

<400> SEQUENCE: 75

Leu Asp Thr Ser Phe His Gln Val Pro Phe His Gln
1               5                   10

<210> SEQ ID NO 76
<211> LENGTH: 11
<212> TYPE: PRT
```

```
<213> ORGANISM: artificial sequence
<220> FEATURE:
<223> OTHER INFORMATION: Synthetic construct

<400> SEQUENCE: 76

Leu Pro Arg Ile Ala Asn Thr Trp Ser Pro Ser
1               5                   10

<210> SEQ ID NO 77
<211> LENGTH: 12
<212> TYPE: PRT
<213> ORGANISM: artificial sequence
<220> FEATURE:
<223> OTHER INFORMATION: Synthetic construct

<400> SEQUENCE: 77

Arg Thr Asn Ala Ala Asp His Pro Ala Ala Val Thr
1               5                   10

<210> SEQ ID NO 78
<211> LENGTH: 12
<212> TYPE: PRT
<213> ORGANISM: artificial sequence
<220> FEATURE:
<223> OTHER INFORMATION: Synthetic construct

<400> SEQUENCE: 78

Ser Leu Asn Trp Val Thr Ile Pro Gly Pro Lys Ile
1               5                   10

<210> SEQ ID NO 79
<211> LENGTH: 12
<212> TYPE: PRT
<213> ORGANISM: artificial sequence
<220> FEATURE:
<223> OTHER INFORMATION: Synthetic construct

<400> SEQUENCE: 79

Thr Asp Met Gln Ala Pro Thr Lys Ser Tyr Ser Asn
1               5                   10

<210> SEQ ID NO 80
<211> LENGTH: 12
<212> TYPE: PRT
<213> ORGANISM: artificial sequence
<220> FEATURE:
<223> OTHER INFORMATION: Synthetic construct

<400> SEQUENCE: 80

Thr Ile Met Thr Lys Ser Pro Ser Leu Ser Cys Gly
1               5                   10

<210> SEQ ID NO 81
<211> LENGTH: 12
<212> TYPE: PRT
<213> ORGANISM: artificial sequence
<220> FEATURE:
<223> OTHER INFORMATION: Synthetic construct

<400> SEQUENCE: 81

Thr Pro Ala Leu Asp Gly Leu Arg Gln Pro Leu Arg
1               5                   10

<210> SEQ ID NO 82
<211> LENGTH: 12
<212> TYPE: PRT
<213> ORGANISM: artificial sequence
<220> FEATURE:
```

<223> OTHER INFORMATION: Synthetic construct

<400> SEQUENCE: 82

Thr Tyr Pro Ala Ser Arg Leu Pro Leu Leu Ala Pro
1               5                   10

<210> SEQ ID NO 83
<211> LENGTH: 12
<212> TYPE: PRT
<213> ORGANISM: artificial sequence
<220> FEATURE:
<223> OTHER INFORMATION: Synthetic construct

<400> SEQUENCE: 83

Ala Lys Thr His Lys His Pro Ala Pro Ser Tyr Ser
1               5                   10

<210> SEQ ID NO 84
<211> LENGTH: 12
<212> TYPE: PRT
<213> ORGANISM: artificial sequence
<220> FEATURE:
<223> OTHER INFORMATION: Synthetic construct

<400> SEQUENCE: 84

Thr Asp Pro Thr Pro Phe Ser Ile Ser Pro Glu Arg
1               5                   10

<210> SEQ ID NO 85
<211> LENGTH: 12
<212> TYPE: PRT
<213> ORGANISM: artificial sequence
<220> FEATURE:
<223> OTHER INFORMATION: Synthetic construct

<400> SEQUENCE: 85

Ser Gln Asn Trp Gln Asp Ser Thr Ser Tyr Ser Asn
1               5                   10

<210> SEQ ID NO 86
<211> LENGTH: 12
<212> TYPE: PRT
<213> ORGANISM: artificial sequence
<220> FEATURE:
<223> OTHER INFORMATION: Synthetic construct

<400> SEQUENCE: 86

Trp His Asp Lys Pro Gln Asn Ser Ser Lys Ser Thr
1               5                   10

<210> SEQ ID NO 87
<211> LENGTH: 12
<212> TYPE: PRT
<213> ORGANISM: artificial sequence
<220> FEATURE:
<223> OTHER INFORMATION: Synthetic construct

<400> SEQUENCE: 87

Leu Asp Val Glu Ser Tyr Lys Gly Thr Ser Met Pro
1               5                   10

<210> SEQ ID NO 88
<211> LENGTH: 7
<212> TYPE: PRT
<213> ORGANISM: artificial sequence
<220> FEATURE:
<223> OTHER INFORMATION: Synthetic construct

```
<400> SEQUENCE: 88

Asn Thr Pro Lys Glu Asn Trp
1               5

<210> SEQ ID NO 89
<211> LENGTH: 7
<212> TYPE: PRT
<213> ORGANISM: artificial sequence
<220> FEATURE:
<223> OTHER INFORMATION: Synthetic construct

<400> SEQUENCE: 89

Asn Thr Pro Ala Ser Asn Arg
1               5

<210> SEQ ID NO 90
<211> LENGTH: 7
<212> TYPE: PRT
<213> ORGANISM: artificial sequence
<220> FEATURE:
<223> OTHER INFORMATION: Synthetic construct

<400> SEQUENCE: 90

Pro Arg Gly Met Leu Ser Thr
1               5

<210> SEQ ID NO 91
<211> LENGTH: 7
<212> TYPE: PRT
<213> ORGANISM: artificial sequence
<220> FEATURE:
<223> OTHER INFORMATION: Synthetic construct

<400> SEQUENCE: 91

Pro Pro Thr Tyr Leu Ser Thr
1               5

<210> SEQ ID NO 92
<211> LENGTH: 12
<212> TYPE: PRT
<213> ORGANISM: artificial sequence
<220> FEATURE:
<223> OTHER INFORMATION: Synthetic construct

<400> SEQUENCE: 92

Thr Ile Pro Thr His Arg Gln His Asp Tyr Arg Ser
1               5                   10

<210> SEQ ID NO 93
<211> LENGTH: 7
<212> TYPE: PRT
<213> ORGANISM: artificial sequence
<220> FEATURE:
<223> OTHER INFORMATION: Synthetic construct

<400> SEQUENCE: 93

Thr Pro Pro Thr His Arg Leu
1               5

<210> SEQ ID NO 94
<211> LENGTH: 7
<212> TYPE: PRT
<213> ORGANISM: artificial sequence
<220> FEATURE:
<223> OTHER INFORMATION: Synthetic construct

<400> SEQUENCE: 94
```

```
Leu Pro Thr Met Ser Thr Pro
1               5

<210> SEQ ID NO 95
<211> LENGTH: 7
<212> TYPE: PRT
<213> ORGANISM: artificial sequence
<220> FEATURE:
<223> OTHER INFORMATION: Synthetic construct

<400> SEQUENCE: 95

Leu Gly Thr Asn Ser Thr Pro
1               5

<210> SEQ ID NO 96
<211> LENGTH: 12
<212> TYPE: PRT
<213> ORGANISM: artificial sequence
<220> FEATURE:
<223> OTHER INFORMATION: Synthetic construct

<400> SEQUENCE: 96

Thr Pro Leu Thr Gly Ser Thr Asn Leu Leu Ser Ser
1               5                   10

<210> SEQ ID NO 97
<211> LENGTH: 7
<212> TYPE: PRT
<213> ORGANISM: artificial sequence
<220> FEATURE:
<223> OTHER INFORMATION: Synthetic construct

<400> SEQUENCE: 97

Thr Pro Leu Thr Lys Glu Thr
1               5

<210> SEQ ID NO 98
<211> LENGTH: 7
<212> TYPE: PRT
<213> ORGANISM: artificial sequence
<220> FEATURE:
<223> OTHER INFORMATION: Synthetic construct

<400> SEQUENCE: 98

Lys Gln Ser His Asn Pro Pro
1               5

<210> SEQ ID NO 99
<211> LENGTH: 7
<212> TYPE: PRT
<213> ORGANISM: artificial sequence
<220> FEATURE:
<223> OTHER INFORMATION: Synthetic construct

<400> SEQUENCE: 99

Gln Gln Ser His Asn Pro Pro
1               5

<210> SEQ ID NO 100
<211> LENGTH: 7
<212> TYPE: PRT
<213> ORGANISM: artificial sequence
<220> FEATURE:
<223> OTHER INFORMATION: Synthetic construct

<400> SEQUENCE: 100

Thr Gln Pro His Asn Pro Pro
1               5
```

```
<210> SEQ ID NO 101
<211> LENGTH: 12
<212> TYPE: PRT
<213> ORGANISM: artificial sequence
<220> FEATURE:
<223> OTHER INFORMATION: Synthetic construct

<400> SEQUENCE: 101

Ser Thr Asn Leu Leu Arg Thr Ser Thr Val His Pro
1               5                   10

<210> SEQ ID NO 102
<211> LENGTH: 12
<212> TYPE: PRT
<213> ORGANISM: artificial sequence
<220> FEATURE:
<223> OTHER INFORMATION: Synthetic construct

<400> SEQUENCE: 102

His Thr Gln Pro Ser Tyr Ser Ser Thr Asn Leu Phe
1               5                   10

<210> SEQ ID NO 103
<211> LENGTH: 7
<212> TYPE: PRT
<213> ORGANISM: artificial sequence
<220> FEATURE:
<223> OTHER INFORMATION: Synthetic construct

<400> SEQUENCE: 103

Ser Leu Leu Ser Ser His Ala
1               5

<210> SEQ ID NO 104
<211> LENGTH: 12
<212> TYPE: PRT
<213> ORGANISM: artificial sequence
<220> FEATURE:
<223> OTHER INFORMATION: Synthetic construct

<400> SEQUENCE: 104

Gln Gln Ser Ser Ile Ser Leu Ser Ser His Ala Val
1               5                   10

<210> SEQ ID NO 105
<211> LENGTH: 7
<212> TYPE: PRT
<213> ORGANISM: artificial sequence
<220> FEATURE:
<223> OTHER INFORMATION: Synthetic construct

<400> SEQUENCE: 105

Asn Ala Ser Pro Ser Ser Leu
1               5

<210> SEQ ID NO 106
<211> LENGTH: 7
<212> TYPE: PRT
<213> ORGANISM: artificial sequence
<220> FEATURE:
<223> OTHER INFORMATION: Synthetic construct

<400> SEQUENCE: 106

His Ser Pro Ser Ser Leu Arg
1               5
```

```
<210> SEQ ID NO 107
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= H, R or N

<400> SEQUENCE: 107

Lys Xaa Ser His His Thr His
1               5

<210> SEQ ID NO 108
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X = H, R or N

<400> SEQUENCE: 108

Glu Xaa Ser His His Thr His
1               5

<210> SEQ ID NO 109
<211> LENGTH: 12
<212> TYPE: PRT
<213> ORGANISM: artificial sequence
<220> FEATURE:
<223> OTHER INFORMATION: Synthetic construct

<400> SEQUENCE: 109

Ser His His Thr His Tyr Gly Gln Pro Gly Pro Val
1               5                   10

<210> SEQ ID NO 110
<211> LENGTH: 7
<212> TYPE: PRT
<213> ORGANISM: artificial sequence
<220> FEATURE:
<223> OTHER INFORMATION: Synthetic construct

<400> SEQUENCE: 110

Leu Glu Ser Thr Ser Leu Leu
1               5

<210> SEQ ID NO 111
<211> LENGTH: 7
<212> TYPE: PRT
<213> ORGANISM: artificial sequence
<220> FEATURE:
<223> OTHER INFORMATION: Synthetic construct

<400> SEQUENCE: 111

Asp Leu Thr Leu Pro Phe His
1               5

<210> SEQ ID NO 112
<211> LENGTH: 8
<212> TYPE: PRT
<213> ORGANISM: artificial sequence
<220> FEATURE:
<223> OTHER INFORMATION: Synthetic construct
```

```
<400> SEQUENCE: 112

Arg Thr Asn Ala Ala Asp His Pro
1               5

<210> SEQ ID NO 113
<211> LENGTH: 12
<212> TYPE: PRT
<213> ORGANISM: artificial sequence
<220> FEATURE:
<223> OTHER INFORMATION: Synthetic construct

<400> SEQUENCE: 113

Ile Pro Trp Trp Asn Ile Arg Ala Pro Leu Asn Ala
1               5                   10

<210> SEQ ID NO 114
<211> LENGTH: 18
<212> TYPE: PRT
<213> ORGANISM: artificial sequence
<220> FEATURE:
<223> OTHER INFORMATION: Synthetic construct

<400> SEQUENCE: 114

Glu Gln Ile Ser Gly Ser Leu Val Ala Ala Pro Trp Glu Gly Glu Gly
1               5                   10                  15

Glu Arg

<210> SEQ ID NO 115
<211> LENGTH: 29
<212> TYPE: PRT
<213> ORGANISM: artificial sequence
<220> FEATURE:
<223> OTHER INFORMATION: Synthetic construct

<400> SEQUENCE: 115

Pro Lys Arg Gly Arg His Lys Arg Pro Lys Arg His Lys Gly Gly
1               5                   10                  15

Thr Pro Pro Glu Leu Leu His Gly Ala Pro Arg Ser Cys
            20                  25

<210> SEQ ID NO 116
<211> LENGTH: 18
<212> TYPE: PRT
<213> ORGANISM: artificial sequence
<220> FEATURE:
<223> OTHER INFORMATION: Synthetic construct

<400> SEQUENCE: 116

Leu Asp Thr Ser Phe His Gln Val Pro Phe His Gln Lys Arg Lys Arg
1               5                   10                  15

Lys Asp

<210> SEQ ID NO 117
<211> LENGTH: 18
<212> TYPE: PRT
<213> ORGANISM: artificial sequence
<220> FEATURE:
<223> OTHER INFORMATION: Synthetic construct

<400> SEQUENCE: 117

Glu Gln Ile Ser Gly Ser Leu Val Ala Ala Pro Trp Lys Arg Lys Arg
1               5                   10                  15

Lys Asp
```

```
<210> SEQ ID NO 118
<211> LENGTH: 18
<212> TYPE: PRT
<213> ORGANISM: artificial sequence
<220> FEATURE:
<223> OTHER INFORMATION: Synthetic construct

<400> SEQUENCE: 118

Thr Pro Pro Glu Leu Leu His Gly Asp Pro Arg Ser Lys Arg Lys Arg
1               5                   10                  15

Lys Asp

<210> SEQ ID NO 119
<211> LENGTH: 13
<212> TYPE: PRT
<213> ORGANISM: artificial sequence
<220> FEATURE:
<223> OTHER INFORMATION: Synthetic construct

<400> SEQUENCE: 119

Asn Thr Ser Gln Leu Ser Thr Glu Gly Glu Gly Glu Asp
1               5                   10

<210> SEQ ID NO 120
<211> LENGTH: 13
<212> TYPE: PRT
<213> ORGANISM: artificial sequence
<220> FEATURE:
<223> OTHER INFORMATION: Synthetic construct

<400> SEQUENCE: 120

Thr Pro Pro Glu Leu Leu His Gly Asp Pro Arg Ser Cys
1               5                   10

<210> SEQ ID NO 121
<211> LENGTH: 20
<212> TYPE: PRT
<213> ORGANISM: artificial sequence
<220> FEATURE:
<223> OTHER INFORMATION: Synthetic construct

<400> SEQUENCE: 121

His Ile Asn Lys Thr Asn Pro His Gln Gly Asn His His Ser Glu Lys
1               5                   10                  15

Thr Gln Arg Gln
            20

<210> SEQ ID NO 122
<211> LENGTH: 15
<212> TYPE: PRT
<213> ORGANISM: artificial sequence
<220> FEATURE:
<223> OTHER INFORMATION: Synthetic construct

<400> SEQUENCE: 122

His Ala His Lys Asn Gln Lys Glu Thr His Gln Arg His Ala Ala
1               5                   10                  15

<210> SEQ ID NO 123
<211> LENGTH: 15
<212> TYPE: PRT
<213> ORGANISM: artificial sequence
<220> FEATURE:
<223> OTHER INFORMATION: Synthetic construct

<400> SEQUENCE: 123

His Glu His Lys Asn Gln Lys Glu Thr His Gln Arg His Ala Ala
```

-continued

<210> SEQ ID NO 124
<211> LENGTH: 20
<212> TYPE: PRT
<213> ORGANISM: artificial sequence
<220> FEATURE:
<223> OTHER INFORMATION: Synthetic construct

<400> SEQUENCE: 124

His Asn His Met Gln Glu Arg Tyr Thr Glu Pro Gln His Ser Pro Ser
1               5                   10                  15

Val Asn Gly Leu
            20

<210> SEQ ID NO 125
<211> LENGTH: 17
<212> TYPE: PRT
<213> ORGANISM: artificial sequence
<220> FEATURE:
<223> OTHER INFORMATION: Synthetic construct

<400> SEQUENCE: 125

Thr His Ser Thr His Asn His Gly Ser Pro Arg His Thr Asn Ala Asp
1               5                   10                  15

Ala

<210> SEQ ID NO 126
<211> LENGTH: 20
<212> TYPE: PRT
<213> ORGANISM: artificial sequence
<220> FEATURE:
<223> OTHER INFORMATION: Synthetic construct

<400> SEQUENCE: 126

Gly Ser Cys Val Asp Thr His Lys Ala Asp Ser Cys Val Ala Asn Asn
1               5                   10                  15

Gly Pro Ala Thr
            20

<210> SEQ ID NO 127
<211> LENGTH: 20
<212> TYPE: PRT
<213> ORGANISM: artificial sequence
<220> FEATURE:
<223> OTHER INFORMATION: Synthetic construct

<400> SEQUENCE: 127

Ala Gln Ser Gln Leu Pro Asp Lys His Ser Gly Leu His Glu Arg Ala
1               5                   10                  15

Pro Gln Arg Tyr
            20

<210> SEQ ID NO 128
<211> LENGTH: 20
<212> TYPE: PRT
<213> ORGANISM: artificial sequence
<220> FEATURE:
<223> OTHER INFORMATION: Synthetic construct

<400> SEQUENCE: 128

Ala Gln Ser Gln Leu Pro Ala Lys His Ser Gly Leu His Glu Arg Ala
1               5                   10                  15

Pro Gln Arg Tyr
            20

```
<210> SEQ ID NO 129
<211> LENGTH: 20
<212> TYPE: PRT
<213> ORGANISM: artificial sequence
<220> FEATURE:
<223> OTHER INFORMATION: Synthetic construct

<400> SEQUENCE: 129

Ala Gln Ser Gln Leu Pro Glu Lys His Ser Gly Leu His Glu Arg Ala
1               5                   10                  15

Pro Gln Arg Tyr
            20

<210> SEQ ID NO 130
<211> LENGTH: 20
<212> TYPE: PRT
<213> ORGANISM: artificial sequence
<220> FEATURE:
<223> OTHER INFORMATION: Synthetic construct

<400> SEQUENCE: 130

Thr Asp Met Met His Asn His Ser Asp Asn Ser Pro Pro His Arg Arg
1               5                   10                  15

Ser Pro Arg Asn
            20

<210> SEQ ID NO 131
<211> LENGTH: 20
<212> TYPE: PRT
<213> ORGANISM: artificial sequence
<220> FEATURE:
<223> OTHER INFORMATION: Synthetic construct

<400> SEQUENCE: 131

Thr Pro Pro Glu Leu Ala His Thr Pro His His Leu Ala Gln Thr Arg
1               5                   10                  15

Leu Thr Asp Arg
            20

<210> SEQ ID NO 132
<211> LENGTH: 12
<212> TYPE: PRT
<213> ORGANISM: artificial sequence
<220> FEATURE:
<223> OTHER INFORMATION: Synthetic construct

<400> SEQUENCE: 132

Arg Leu Leu Arg Leu Leu Arg Leu Leu Arg Leu Leu
1               5                   10

<210> SEQ ID NO 133
<211> LENGTH: 12
<212> TYPE: PRT
<213> ORGANISM: artificial sequence
<220> FEATURE:
<223> OTHER INFORMATION: Synthetic construct

<400> SEQUENCE: 133

Thr Pro Pro Glu Leu Leu His Gly Glu Pro Arg Ser
1               5                   10

<210> SEQ ID NO 134
<211> LENGTH: 12
<212> TYPE: PRT
<213> ORGANISM: artificial sequence
```

```
<220> FEATURE:
<223> OTHER INFORMATION: Synthetic construct

<400> SEQUENCE: 134

Thr Pro Pro Glu Leu Leu His Gly Ala Pro Arg Ser
1               5                   10

<210> SEQ ID NO 135
<211> LENGTH: 12
<212> TYPE: PRT
<213> ORGANISM: artificial sequence
<220> FEATURE:
<223> OTHER INFORMATION: Synthetic construct

<400> SEQUENCE: 135

Glu Gln Ile Ser Gly Ser Leu Val Ala Ala Pro Trp
1               5                   10

<210> SEQ ID NO 136
<211> LENGTH: 12
<212> TYPE: PRT
<213> ORGANISM: artificial sequence
<220> FEATURE:
<223> OTHER INFORMATION: Synthetic construct

<400> SEQUENCE: 136

Asn Glu Val Pro Ala Arg Asn Ala Pro Trp Leu Val
1               5                   10

<210> SEQ ID NO 137
<211> LENGTH: 13
<212> TYPE: PRT
<213> ORGANISM: artificial sequence
<220> FEATURE:
<223> OTHER INFORMATION: Synthetic construct

<400> SEQUENCE: 137

Asn Ser Pro Gly Tyr Gln Ala Asp Ser Val Ala Ile Gly
1               5                   10

<210> SEQ ID NO 138
<211> LENGTH: 12
<212> TYPE: PRT
<213> ORGANISM: artificial sequence
<220> FEATURE:
<223> OTHER INFORMATION: Synthetic construct

<400> SEQUENCE: 138

Ala Lys Pro Ile Ser Gln His Leu Gln Arg Gly Ser
1               5                   10

<210> SEQ ID NO 139
<211> LENGTH: 12
<212> TYPE: PRT
<213> ORGANISM: artificial sequence
<220> FEATURE:
<223> OTHER INFORMATION: Synthetic construct

<400> SEQUENCE: 139

Leu Asp Thr Ser Phe Pro Pro Val Pro Phe His Ala
1               5                   10

<210> SEQ ID NO 140
<211> LENGTH: 12
<212> TYPE: PRT
<213> ORGANISM: artificial sequence
<220> FEATURE:
<223> OTHER INFORMATION: Synthetic construct
```

```
<400> SEQUENCE: 140

Ser Leu Asn Trp Val Thr Ile Pro Gly Pro Lys Ile
1               5                   10

<210> SEQ ID NO 141
<211> LENGTH: 12
<212> TYPE: PRT
<213> ORGANISM: artificial sequence
<220> FEATURE:
<223> OTHER INFORMATION: Synthetic construct

<400> SEQUENCE: 141

Thr Gln Asp Ser Ala Gln Lys Ser Pro Ser Pro Leu
1               5                   10

<210> SEQ ID NO 142
<211> LENGTH: 12
<212> TYPE: PRT
<213> ORGANISM: artificial sequence
<220> FEATURE:
<223> OTHER INFORMATION: Synthetic construct

<400> SEQUENCE: 142

Lys Glu Leu Gln Thr Arg Asn Val Val Gln Arg Glu
1               5                   10

<210> SEQ ID NO 143
<211> LENGTH: 12
<212> TYPE: PRT
<213> ORGANISM: artificial sequence
<220> FEATURE:
<223> OTHER INFORMATION: Synthetic construct

<400> SEQUENCE: 143

Gln Arg Asn Ser Pro Pro Ala Met Ser Arg Arg Asp
1               5                   10

<210> SEQ ID NO 144
<211> LENGTH: 12
<212> TYPE: PRT
<213> ORGANISM: artificial sequence
<220> FEATURE:
<223> OTHER INFORMATION: Synthetic construct

<400> SEQUENCE: 144

Thr Pro Thr Ala Asn Gln Phe Thr Gln Ser Val Pro
1               5                   10

<210> SEQ ID NO 145
<211> LENGTH: 12
<212> TYPE: PRT
<213> ORGANISM: artificial sequence
<220> FEATURE:
<223> OTHER INFORMATION: Synthetic construct

<400> SEQUENCE: 145

Ala Ala Gly Leu Ser Gln Lys His Glu Arg Asn Arg
1               5                   10

<210> SEQ ID NO 146
<211> LENGTH: 12
<212> TYPE: PRT
<213> ORGANISM: artificial sequence
<220> FEATURE:
<223> OTHER INFORMATION: Synthetic construct

<400> SEQUENCE: 146
```

```
Glu Thr Val His Gln Thr Pro Leu Ser Asp Arg Pro
1               5                   10
```

<210> SEQ ID NO 147
<211> LENGTH: 12
<212> TYPE: PRT
<213> ORGANISM: artificial sequence
<220> FEATURE:
<223> OTHER INFORMATION: Synthetic construct

<400> SEQUENCE: 147

```
Lys Asn Phe Pro Gln Gln Lys Glu Phe Pro Leu Ser
1               5                   10
```

<210> SEQ ID NO 148
<211> LENGTH: 12
<212> TYPE: PRT
<213> ORGANISM: artificial sequence
<220> FEATURE:
<223> OTHER INFORMATION: Synthetic construct

<400> SEQUENCE: 148

```
Leu Pro Ala Leu His Ile Gln Arg His Pro Arg Met
1               5                   10
```

<210> SEQ ID NO 149
<211> LENGTH: 12
<212> TYPE: PRT
<213> ORGANISM: artificial sequence
<220> FEATURE:
<223> OTHER INFORMATION: Synthetic construct

<400> SEQUENCE: 149

```
Gln Pro Ser His Ser Gln Ser His Asn Leu Arg Ser
1               5                   10
```

<210> SEQ ID NO 150
<211> LENGTH: 12
<212> TYPE: PRT
<213> ORGANISM: artificial sequence
<220> FEATURE:
<223> OTHER INFORMATION: Synthetic construct

<400> SEQUENCE: 150

```
Arg Gly Ser Gln Lys Ser Lys Pro Pro Arg Pro Pro
1               5                   10
```

<210> SEQ ID NO 151
<211> LENGTH: 12
<212> TYPE: PRT
<213> ORGANISM: artificial sequence
<220> FEATURE:
<223> OTHER INFORMATION: Synthetic construct

<400> SEQUENCE: 151

```
Thr His Thr Gln Lys Thr Pro Leu Leu Tyr Tyr His
1               5                   10
```

<210> SEQ ID NO 152
<211> LENGTH: 12
<212> TYPE: PRT
<213> ORGANISM: artificial sequence
<220> FEATURE:
<223> OTHER INFORMATION: Synthetic construct

<400> SEQUENCE: 152

```
Thr Lys Gly Ser Ser Gln Ala Ile Leu Lys Ser Thr
```

<210> SEQ ID NO 153
<211> LENGTH: 7
<212> TYPE: PRT
<213> ORGANISM: artificial sequence
<220> FEATURE:
<223> OTHER INFORMATION: Synthetic construct

<400> SEQUENCE: 153

Thr Ala Ala Thr Thr Ser Pro
1               5

<210> SEQ ID NO 154
<211> LENGTH: 7
<212> TYPE: PRT
<213> ORGANISM: artificial sequence
<220> FEATURE:
<223> OTHER INFORMATION: Synthetic construct

<400> SEQUENCE: 154

Leu Gly Ile Pro Gln Asn Leu
1               5

<210> SEQ ID NO 155
<211> LENGTH: 20
<212> TYPE: PRT
<213> ORGANISM: artificial sequence
<220> FEATURE:
<223> OTHER INFORMATION: Synthetic construct

<400> SEQUENCE: 155

Thr His Ser Thr His Asn His Gly Ser Pro Arg His Thr Asn Ala Asp
1               5                   10                  15

Ala Gly Asn Pro
            20

<210> SEQ ID NO 156
<211> LENGTH: 20
<212> TYPE: PRT
<213> ORGANISM: artificial sequence
<220> FEATURE:
<223> OTHER INFORMATION: Synthetic construct

<400> SEQUENCE: 156

Gln Gln His Lys Val His His Gln Asn Pro Asp Arg Ser Thr Gln Asp
1               5                   10                  15

Ala His His Ser
            20

<210> SEQ ID NO 157
<211> LENGTH: 15
<212> TYPE: PRT
<213> ORGANISM: artificial sequence
<220> FEATURE:
<223> OTHER INFORMATION: Synthetic construct

<400> SEQUENCE: 157

His His Gly Thr His His Asn Ala Thr Lys Gln Lys Asn His Val
1               5                   10                  15

<210> SEQ ID NO 158
<211> LENGTH: 15
<212> TYPE: PRT
<213> ORGANISM: artificial sequence
<220> FEATURE:
<223> OTHER INFORMATION: Synthetic construct

<400> SEQUENCE: 158

Ser Thr Leu His Lys Tyr Lys Ser Gln Asp Pro Thr Pro His His
1               5                   10                  15

<210> SEQ ID NO 159
<211> LENGTH: 12
<212> TYPE: PRT
<213> ORGANISM: artificial sequence
<220> FEATURE:
<223> OTHER INFORMATION: Synthetic construct

<400> SEQUENCE: 159

Ser Val Ser Val Gly Met Lys Pro Ser Pro Arg Pro
1               5                   10

<210> SEQ ID NO 160
<211> LENGTH: 12
<212> TYPE: PRT
<213> ORGANISM: artificial sequence
<220> FEATURE:
<223> OTHER INFORMATION: Synthetic construct

<400> SEQUENCE: 160

Thr Pro Pro Thr Asn Val Leu Met Leu Ala Thr Lys
1               5                   10

<210> SEQ ID NO 161
<211> LENGTH: 12
<212> TYPE: PRT
<213> ORGANISM: artificial sequence
<220> FEATURE:
<223> OTHER INFORMATION: Synthetic construct

<400> SEQUENCE: 161

Thr Pro Pro Glu Leu Leu His Gly Asp Pro Arg Ser
1               5                   10

<210> SEQ ID NO 162
<211> LENGTH: 7
<212> TYPE: PRT
<213> ORGANISM: artificial sequence
<220> FEATURE:
<223> OTHER INFORMATION: Synthetic construct

<400> SEQUENCE: 162

Asn Thr Ser Gln Leu Ser Thr
1               5

<210> SEQ ID NO 163
<211> LENGTH: 15
<212> TYPE: PRT
<213> ORGANISM: artificial sequence
<220> FEATURE:
<223> OTHER INFORMATION: Synthetic construct

<400> SEQUENCE: 163

Ser Thr Leu His Lys Tyr Lys Ser Gln Asp Pro Thr Pro His His
1               5                   10                  15

<210> SEQ ID NO 164
<211> LENGTH: 12
<212> TYPE: PRT
<213> ORGANISM: artificial sequence
<220> FEATURE:
<223> OTHER INFORMATION: Synthetic construct

<400> SEQUENCE: 164

```
Gly Met Pro Ala Met His Trp Ile His Pro Phe Ala
1               5                   10

<210> SEQ ID NO 165
<211> LENGTH: 15
<212> TYPE: PRT
<213> ORGANISM: artificial sequence
<220> FEATURE:
<223> OTHER INFORMATION: Synthetic construct

<400> SEQUENCE: 165

His Asp His Lys Asn Gln Lys Glu Thr His Gln Arg His Ala Ala
1               5                   10                  15

<210> SEQ ID NO 166
<211> LENGTH: 20
<212> TYPE: PRT
<213> ORGANISM: artificial sequence
<220> FEATURE:
<223> OTHER INFORMATION: Synthetic construct

<400> SEQUENCE: 166

His Asn His Met Gln Glu Arg Tyr Thr Asp Pro Gln His Ser Pro Ser
1               5                   10                  15

Val Asn Gly Leu
            20

<210> SEQ ID NO 167
<211> LENGTH: 20
<212> TYPE: PRT
<213> ORGANISM: artificial sequence
<220> FEATURE:
<223> OTHER INFORMATION: Synthetic construct

<400> SEQUENCE: 167

Thr Ala Glu Ile Gln Ser Ser Lys Asn Pro Asn Pro His Pro Gln Arg
1               5                   10                  15

Ser Trp Thr Asn
            20

<210> SEQ ID NO 168
<211> LENGTH: 67
<212> TYPE: PRT
<213> ORGANISM: artificial sequence
<220> FEATURE:
<223> OTHER INFORMATION: Synthetic construct

<400> SEQUENCE: 168

Pro Asn Thr Ser Gln Leu Ser Thr Gly Gly Gly Arg Thr Asn Ala Ala
1               5                   10                  15

Asp His Pro Lys Cys Gly Gly Gly Asn Thr Ser Gln Leu Ser Thr Gly
            20                  25                  30

Gly Gly Arg Thr Asn Ala Ala Asp His Pro Lys Cys Gly Gly Gly Asn
        35                  40                  45

Thr Ser Gln Leu Ser Thr Gly Gly Gly Arg Thr Asn Ala Ala Asp His
    50                  55                  60

Pro Lys Cys
65

<210> SEQ ID NO 169
<211> LENGTH: 55
<212> TYPE: PRT
<213> ORGANISM: artificial sequence
<220> FEATURE:
```

-continued

<223> OTHER INFORMATION: Synthetic construct

<400> SEQUENCE: 169

Pro Arg Thr Asn Ala Ala Asp His Pro Ala Ala Val Thr Gly Gly Gly
1               5                   10                  15

Cys Gly Gly Gly Arg Thr Asn Ala Ala Asp His Pro Ala Ala Val Thr
            20                  25                  30

Gly Gly Gly Cys Gly Gly Gly Arg Thr Asn Ala Ala Asp His Pro Ala
        35                  40                  45

Ala Val Thr Gly Gly Gly Cys
    50                  55

<210> SEQ ID NO 170
<211> LENGTH: 50
<212> TYPE: PRT
<213> ORGANISM: artificial sequence
<220> FEATURE:
<223> OTHER INFORMATION: Synthetic construct

<400> SEQUENCE: 170

Pro Arg Thr Asn Ala Ala Asp His Pro Ala Ala Val Thr Gly Gly Gly
1               5                   10                  15

Cys Gly Gly Gly Ile Pro Trp Trp Asn Ile Arg Ala Pro Leu Asn Ala
            20                  25                  30

Gly Gly Gly Cys Gly Gly Gly Asp Leu Thr Leu Pro Phe His Gly Gly
        35                  40                  45

Gly Cys
    50

<210> SEQ ID NO 171
<211> LENGTH: 82
<212> TYPE: PRT
<213> ORGANISM: artificial sequence
<220> FEATURE:
<223> OTHER INFORMATION: Synthetic construct

<400> SEQUENCE: 171

Pro Arg Thr Asn Ala Ala Asp His Pro Gly Gly Gly Thr Pro Pro Glu
1               5                   10                  15

Leu Leu His Gly Asp Pro Arg Ser Lys Cys Gly Gly Gly Arg Thr Asn
            20                  25                  30

Ala Ala Asp His Pro Gly Gly Gly Thr Pro Pro Glu Leu Leu His Gly
        35                  40                  45

Asp Pro Arg Ser Lys Cys Gly Gly Gly Arg Thr Asn Ala Ala Asp His
    50                  55                  60

Pro Gly Gly Gly Thr Pro Pro Glu Leu Leu His Gly Asp Pro Arg Ser
65                  70                  75                  80

Lys Cys

<210> SEQ ID NO 172
<211> LENGTH: 82
<212> TYPE: PRT
<213> ORGANISM: artificial sequence
<220> FEATURE:
<223> OTHER INFORMATION: Synthetic construct

<400> SEQUENCE: 172

Pro Thr Pro Pro Thr Asn Val Leu Met Leu Ala Thr Lys Gly Gly Gly
1               5                   10                  15

Arg Thr Asn Ala Ala Asp His Pro Lys Cys Gly Gly Thr Pro Pro
            20                  25                  30

```
Thr Asn Val Leu Met Leu Ala Thr Lys Gly Gly Gly Arg Thr Asn Ala
            35                  40                  45

Ala Asp His Pro Lys Cys Gly Gly Gly Thr Pro Thr Asn Val Leu
    50                  55                  60

Met Leu Ala Thr Lys Gly Gly Gly Arg Thr Asn Ala Ala Asp His Pro
 65                  70                  75                  80

Lys Cys

<210> SEQ ID NO 173
<211> LENGTH: 82
<212> TYPE: PRT
<213> ORGANISM: artificial sequence
<220> FEATURE:
<223> OTHER INFORMATION: Synthetic construct

<400> SEQUENCE: 173

Pro Arg Thr Asn Ala Ala Asp His Pro Gly Gly Gly Thr Pro Pro Thr
  1               5                  10                  15

Asn Val Leu Met Leu Ala Thr Lys Lys Cys Gly Gly Gly Arg Thr Asn
                20                  25                  30

Ala Ala Asp His Pro Gly Gly Gly Thr Pro Pro Thr Asn Val Leu Met
            35                  40                  45

Leu Ala Thr Lys Lys Cys Gly Gly Gly Arg Thr Asn Ala Ala Asp His
    50                  55                  60

Pro Gly Gly Gly Thr Pro Pro Thr Asn Val Leu Met Leu Ala Thr Lys
 65                  70                  75                  80

Lys Cys

<210> SEQ ID NO 174
<211> LENGTH: 60
<212> TYPE: PRT
<213> ORGANISM: artificial sequence
<220> FEATURE:
<223> OTHER INFORMATION: Synthetic construct

<400> SEQUENCE: 174

Pro Gly Ile Pro Trp Trp Asn Ile Arg Ala Pro Leu Asn Ala Gly Ala
  1               5                  10                  15

Gly Ile Pro Trp Trp Asn Ile Arg Ala Pro Leu Asn Ala Gly Gly Ser
                20                  25                  30

Gly Pro Gly Ser Gly Gly Asn Thr Ser Gln Leu Ser Thr Gly Gly Gly
            35                  40                  45

Asn Thr Ser Gln Leu Ser Thr Gly Gly Pro Lys Lys
    50                  55                  60

<210> SEQ ID NO 175
<211> LENGTH: 12
<212> TYPE: PRT
<213> ORGANISM: artificial sequence
<220> FEATURE:
<223> OTHER INFORMATION: Synthetic construct

<400> SEQUENCE: 175

Lys Arg Gly Arg His Lys Arg Pro Lys Arg His Lys
  1               5                  10

<210> SEQ ID NO 176
<211> LENGTH: 7
<212> TYPE: PRT
<213> ORGANISM: artificial sequence
<220> FEATURE:
```

<223> OTHER INFORMATION: Synthetic construct

<400> SEQUENCE: 176

Arg Leu Leu Arg Leu Leu Arg
1               5

<210> SEQ ID NO 177
<211> LENGTH: 12
<212> TYPE: PRT
<213> ORGANISM: artificial sequence
<220> FEATURE:
<223> OTHER INFORMATION: Synthetic construct

<400> SEQUENCE: 177

His Lys Pro Arg Gly Gly Arg Lys Lys Ala Leu His
1               5                   10

<210> SEQ ID NO 178
<211> LENGTH: 18
<212> TYPE: PRT
<213> ORGANISM: artificial sequence
<220> FEATURE:
<223> OTHER INFORMATION: Synthetic construct

<400> SEQUENCE: 178

Lys Pro Arg Pro Pro His Gly Lys Lys His Arg Pro Lys His Arg Pro
1               5                   10                  15

Lys Lys

<210> SEQ ID NO 179
<211> LENGTH: 18
<212> TYPE: PRT
<213> ORGANISM: artificial sequence
<220> FEATURE:
<223> OTHER INFORMATION: Synthetic construct

<400> SEQUENCE: 179

Arg Gly Arg Pro Lys Lys Gly His Gly Lys Arg Pro Gly His Arg Ala
1               5                   10                  15

Arg Lys

<210> SEQ ID NO 180
<211> LENGTH: 12
<212> TYPE: PRT
<213> ORGANISM: artificial sequence
<220> FEATURE:
<223> OTHER INFORMATION: Synthetic construct

<400> SEQUENCE: 180

Thr Pro Phe His Ser Pro Glu Asn Ala Pro Gly Ser
1               5                   10

<210> SEQ ID NO 181
<211> LENGTH: 13
<212> TYPE: PRT
<213> ORGANISM: artificial sequence
<220> FEATURE:
<223> OTHER INFORMATION: Synthetic construct

<400> SEQUENCE: 181

Thr Pro Phe His Ser Pro Glu Asn Ala Pro Gly Ser Lys
1               5                   10

<210> SEQ ID NO 182
<211> LENGTH: 16
<212> TYPE: PRT

```
<213> ORGANISM: artificial sequence
<220> FEATURE:
<223> OTHER INFORMATION: Synthetic construct

<400> SEQUENCE: 182

Thr Pro Phe His Ser Pro Glu Asn Ala Pro Gly Ser Gly Gly Gly Ser
1               5                   10                  15

<210> SEQ ID NO 183
<211> LENGTH: 17
<212> TYPE: PRT
<213> ORGANISM: artificial sequence
<220> FEATURE:
<223> OTHER INFORMATION: Synthetic construct

<400> SEQUENCE: 183

Thr Pro Phe His Ser Pro Glu Asn Ala Pro Gly Ser Gly Gly Gly Ser
1               5                   10                  15

Ser

<210> SEQ ID NO 184
<211> LENGTH: 15
<212> TYPE: PRT
<213> ORGANISM: artificial sequence
<220> FEATURE:
<223> OTHER INFORMATION: Synthetic construct

<400> SEQUENCE: 184

Thr Pro Phe His Ser Pro Glu Asn Ala Pro Gly Ser Gly Gly Gly
1               5                   10                  15

<210> SEQ ID NO 185
<211> LENGTH: 7
<212> TYPE: PRT
<213> ORGANISM: artificial sequence
<220> FEATURE:
<223> OTHER INFORMATION: Synthetic construct

<400> SEQUENCE: 185

Phe Thr Gln Ser Leu Pro Arg
1               5

<210> SEQ ID NO 186
<211> LENGTH: 12
<212> TYPE: PRT
<213> ORGANISM: artificial sequence
<220> FEATURE:
<223> OTHER INFORMATION: Synthetic construct

<400> SEQUENCE: 186

Lys Gln Ala Thr Phe Pro Pro Asn Pro Thr Ala Tyr
1               5                   10

<210> SEQ ID NO 187
<211> LENGTH: 12
<212> TYPE: PRT
<213> ORGANISM: artificial sequence
<220> FEATURE:
<223> OTHER INFORMATION: Synthetic construct

<400> SEQUENCE: 187

His Gly His Met Val Ser Thr Ser Gln Leu Ser Ile
1               5                   10

<210> SEQ ID NO 188
<211> LENGTH: 7
<212> TYPE: PRT
```

<213> ORGANISM: artificial sequence
<220> FEATURE:
<223> OTHER INFORMATION: Synthetic construct

<400> SEQUENCE: 188

Leu Ser Pro Ser Arg Met Lys
1               5

<210> SEQ ID NO 189
<211> LENGTH: 7
<212> TYPE: PRT
<213> ORGANISM: artificial sequence
<220> FEATURE:
<223> OTHER INFORMATION: Synthetic construct

<400> SEQUENCE: 189

Leu Pro Ile Pro Arg Met Lys
1               5

<210> SEQ ID NO 190
<211> LENGTH: 7
<212> TYPE: PRT
<213> ORGANISM: artificial sequence
<220> FEATURE:
<223> OTHER INFORMATION: Synthetic construct

<400> SEQUENCE: 190

His Gln Arg Pro Tyr Leu Thr
1               5

<210> SEQ ID NO 191
<211> LENGTH: 7
<212> TYPE: PRT
<213> ORGANISM: artificial sequence
<220> FEATURE:
<223> OTHER INFORMATION: Synthetic construct

<400> SEQUENCE: 191

Phe Pro Pro Leu Leu Arg Leu
1               5

<210> SEQ ID NO 192
<211> LENGTH: 7
<212> TYPE: PRT
<213> ORGANISM: artificial sequence
<220> FEATURE:
<223> OTHER INFORMATION: Synthetic construct

<400> SEQUENCE: 192

Gln Ala Thr Phe Met Tyr Asn
1               5

<210> SEQ ID NO 193
<211> LENGTH: 11
<212> TYPE: PRT
<213> ORGANISM: artificial sequence
<220> FEATURE:
<223> OTHER INFORMATION: Synthetic construct

<400> SEQUENCE: 193

Val Leu Thr Ser Gln Leu Pro Asn His Ser Met
1               5                   10

<210> SEQ ID NO 194
<211> LENGTH: 7
<212> TYPE: PRT
<213> ORGANISM: artificial sequence
<220> FEATURE:

<223> OTHER INFORMATION: Synthetic construct

<400> SEQUENCE: 194

His Ser Thr Ala Tyr Leu Thr
1               5

<210> SEQ ID NO 195
<211> LENGTH: 12
<212> TYPE: PRT
<213> ORGANISM: artificial sequence
<220> FEATURE:
<223> OTHER INFORMATION: Synthetic construct

<400> SEQUENCE: 195

Ala Pro Gln Gln Arg Pro Met Lys Thr Phe Asn Thr
1               5                   10

<210> SEQ ID NO 196
<211> LENGTH: 12
<212> TYPE: PRT
<213> ORGANISM: artificial sequence
<220> FEATURE:
<223> OTHER INFORMATION: Synthetic construct

<400> SEQUENCE: 196

Ala Pro Gln Gln Arg Pro Met Lys Thr Val Gln Tyr
1               5                   10

<210> SEQ ID NO 197
<211> LENGTH: 7
<212> TYPE: PRT
<213> ORGANISM: artificial sequence
<220> FEATURE:
<223> OTHER INFORMATION: Synthetic construct

<400> SEQUENCE: 197

Pro Pro Trp Leu Asp Leu Leu
1               5

<210> SEQ ID NO 198
<211> LENGTH: 7
<212> TYPE: PRT
<213> ORGANISM: artificial sequence
<220> FEATURE:
<223> OTHER INFORMATION: Synthetic construct

<400> SEQUENCE: 198

Pro Pro Trp Thr Phe Pro Leu
1               5

<210> SEQ ID NO 199
<211> LENGTH: 7
<212> TYPE: PRT
<213> ORGANISM: artificial sequence
<220> FEATURE:
<223> OTHER INFORMATION: Synthetic construct

<400> SEQUENCE: 199

Ser Val Thr His Leu Thr Ser
1               5

<210> SEQ ID NO 200
<211> LENGTH: 7
<212> TYPE: PRT
<213> ORGANISM: artificial sequence
<220> FEATURE:
<223> OTHER INFORMATION: Synthetic construct

```
<400> SEQUENCE: 200

Val Ile Thr Arg Leu Thr Ser
1               5

<210> SEQ ID NO 201
<211> LENGTH: 12
<212> TYPE: PRT
<213> ORGANISM: artificial sequence
<220> FEATURE:
<223> OTHER INFORMATION: Synthetic construct

<400> SEQUENCE: 201

Asp Leu Lys Pro Pro Leu Leu Ala Leu Ser Lys Val
1               5                   10

<210> SEQ ID NO 202
<211> LENGTH: 12
<212> TYPE: PRT
<213> ORGANISM: artificial sequence
<220> FEATURE:
<223> OTHER INFORMATION: Synthetic construct

<400> SEQUENCE: 202

Ser His Pro Ser Gly Ala Leu Gln Glu Gly Thr Phe
1               5                   10

<210> SEQ ID NO 203
<211> LENGTH: 12
<212> TYPE: PRT
<213> ORGANISM: artificial sequence
<220> FEATURE:
<223> OTHER INFORMATION: Synthetic construct

<400> SEQUENCE: 203

Phe Pro Leu Thr Ser Lys Pro Ser Gly Ala Cys Thr
1               5                   10

<210> SEQ ID NO 204
<211> LENGTH: 12
<212> TYPE: PRT
<213> ORGANISM: artificial sequence
<220> FEATURE:
<223> OTHER INFORMATION: Synthetic construct

<400> SEQUENCE: 204

Asp Leu Lys Pro Pro Leu Leu Ala Leu Ser Lys Val
1               5                   10

<210> SEQ ID NO 205
<211> LENGTH: 7
<212> TYPE: PRT
<213> ORGANISM: artificial sequence
<220> FEATURE:
<223> OTHER INFORMATION: Synthetic construct

<400> SEQUENCE: 205

Pro Leu Leu Ala Leu His Ser
1               5

<210> SEQ ID NO 206
<211> LENGTH: 7
<212> TYPE: PRT
<213> ORGANISM: artificial sequence
<220> FEATURE:
<223> OTHER INFORMATION: Synthetic construct

<400> SEQUENCE: 206
```

```
Val Pro Ile Ser Thr Gln Ile
1               5
```

<210> SEQ ID NO 207
<211> LENGTH: 12
<212> TYPE: PRT
<213> ORGANISM: artificial sequence
<220> FEATURE:
<223> OTHER INFORMATION: Synthetic construct

<400> SEQUENCE: 207

```
Tyr Ala Lys Gln His Tyr Pro Ile Ser Thr Phe Lys
1               5                   10
```

<210> SEQ ID NO 208
<211> LENGTH: 7
<212> TYPE: PRT
<213> ORGANISM: artificial sequence
<220> FEATURE:
<223> OTHER INFORMATION: Synthetic construct

<400> SEQUENCE: 208

```
His Ser Thr Ala Tyr Leu Thr
1               5
```

<210> SEQ ID NO 209
<211> LENGTH: 12
<212> TYPE: PRT
<213> ORGANISM: artificial sequence
<220> FEATURE:
<223> OTHER INFORMATION: Synthetic construct

<400> SEQUENCE: 209

```
Ser Thr Ala Tyr Leu Val Ala Met Ser Ala Ala Pro
1               5                   10
```

<210> SEQ ID NO 210
<211> LENGTH: 12
<212> TYPE: PRT
<213> ORGANISM: artificial sequence
<220> FEATURE:
<223> OTHER INFORMATION: Synthetic construct

<400> SEQUENCE: 210

```
Ser Val Ser Val Gly Met Lys Pro Ser Pro Arg Pro
1               5                   10
```

<210> SEQ ID NO 211
<211> LENGTH: 12
<212> TYPE: PRT
<213> ORGANISM: artificial sequence
<220> FEATURE:
<223> OTHER INFORMATION: Synthetic construct

<400> SEQUENCE: 211

```
Thr Met Gly Phe Thr Ala Pro Arg Phe Pro His Tyr
1               5                   10
```

<210> SEQ ID NO 212
<211> LENGTH: 12
<212> TYPE: PRT
<213> ORGANISM: artificial sequence
<220> FEATURE:
<223> OTHER INFORMATION: Synthetic construct

<400> SEQUENCE: 212

```
Asn Leu Gln His Ser Val Gly Thr Ser Pro Val Trp
1               5                   10
```

<210> SEQ ID NO 213
<211> LENGTH: 15
<212> TYPE: PRT
<213> ORGANISM: artificial sequence
<220> FEATURE:
<223> OTHER INFORMATION: Synthetic construct

<400> SEQUENCE: 213

Gln Leu Ser Tyr His Ala Tyr Pro Gln Ala Asn His His Ala Pro
1               5                   10                  15

<210> SEQ ID NO 214
<211> LENGTH: 12
<212> TYPE: PRT
<213> ORGANISM: artificial sequence
<220> FEATURE:
<223> OTHER INFORMATION: Synthetic construct

<400> SEQUENCE: 214

Asn Gln Ala Ala Ser Ile Thr Lys Arg Val Pro Tyr
1               5                   10

<210> SEQ ID NO 215
<211> LENGTH: 14
<212> TYPE: PRT
<213> ORGANISM: artificial sequence
<220> FEATURE:
<223> OTHER INFORMATION: Synthetic construct

<400> SEQUENCE: 215

Ser Gly Cys His Leu Val Tyr Asp Asn Gly Phe Cys Asp His
1               5                   10

<210> SEQ ID NO 216
<211> LENGTH: 14
<212> TYPE: PRT
<213> ORGANISM: artificial sequence
<220> FEATURE:
<223> OTHER INFORMATION: Synthetic construct

<400> SEQUENCE: 216

Ala Ser Cys Pro Ser Ala Ser His Ala Asp Pro Cys Ala His
1               5                   10

<210> SEQ ID NO 217
<211> LENGTH: 14
<212> TYPE: PRT
<213> ORGANISM: artificial sequence
<220> FEATURE:
<223> OTHER INFORMATION: Synthetic construct

<400> SEQUENCE: 217

Asn Leu Cys Asp Ser Ala Arg Asp Ser Pro Arg Cys Lys Val
1               5                   10

<210> SEQ ID NO 218
<211> LENGTH: 12
<212> TYPE: PRT
<213> ORGANISM: artificial sequence
<220> FEATURE:
<223> OTHER INFORMATION: Synthetic construct

<400> SEQUENCE: 218

Asn His Ser Asn Trp Lys Thr Ala Ala Asp Phe Leu
1               5                   10

```
<210> SEQ ID NO 219
<211> LENGTH: 12
<212> TYPE: PRT
<213> ORGANISM: artificial sequence
<220> FEATURE:
<223> OTHER INFORMATION: Synthetic construct

<400> SEQUENCE: 219

Gly Ser Ser Thr Val Gly Arg Pro Leu Ser Tyr Glu
1               5                   10

<210> SEQ ID NO 220
<211> LENGTH: 12
<212> TYPE: PRT
<213> ORGANISM: artificial sequence
<220> FEATURE:
<223> OTHER INFORMATION: Synthetic construct

<400> SEQUENCE: 220

Ser Asp Thr Ile Ser Arg Leu His Val Ser Met Thr
1               5                   10

<210> SEQ ID NO 221
<211> LENGTH: 12
<212> TYPE: PRT
<213> ORGANISM: artificial sequence
<220> FEATURE:
<223> OTHER INFORMATION: Synthetic construct

<400> SEQUENCE: 221

Ser Pro Leu Thr Val Pro Tyr Glu Arg Lys Leu Leu
1               5                   10

<210> SEQ ID NO 222
<211> LENGTH: 12
<212> TYPE: PRT
<213> ORGANISM: artificial sequence
<220> FEATURE:
<223> OTHER INFORMATION: Synthetic construct

<400> SEQUENCE: 222

Ser Pro Tyr Pro Ser Trp Ser Thr Pro Ala Gly Arg
1               5                   10

<210> SEQ ID NO 223
<211> LENGTH: 12
<212> TYPE: PRT
<213> ORGANISM: artificial sequence
<220> FEATURE:
<223> OTHER INFORMATION: Synthetic construct

<400> SEQUENCE: 223

Val Gln Pro Ile Thr Asn Thr Arg Tyr Glu Gly Gly
1               5                   10

<210> SEQ ID NO 224
<211> LENGTH: 12
<212> TYPE: PRT
<213> ORGANISM: artificial sequence
<220> FEATURE:
<223> OTHER INFORMATION: Synthetic construct

<400> SEQUENCE: 224

Trp Pro Met His Pro Glu Lys Gly Ser Arg Trp Ser
1               5                   10

<210> SEQ ID NO 225
<211> LENGTH: 14
```

```
<212> TYPE: PRT
<213> ORGANISM: artificial sequence
<220> FEATURE:
<223> OTHER INFORMATION: Synthetic construct

<400> SEQUENCE: 225

Asp Ala Cys Ser Gly Asn Gly His Pro Asn Asn Cys Asp Arg
1               5                   10

<210> SEQ ID NO 226
<211> LENGTH: 14
<212> TYPE: PRT
<213> ORGANISM: artificial sequence
<220> FEATURE:
<223> OTHER INFORMATION: Synthetic construct

<400> SEQUENCE: 226

Asp His Cys Leu Gly Arg Gln Leu Gln Pro Val Cys Tyr Pro
1               5                   10

<210> SEQ ID NO 227
<211> LENGTH: 14
<212> TYPE: PRT
<213> ORGANISM: artificial sequence
<220> FEATURE:
<223> OTHER INFORMATION: Synthetic construct

<400> SEQUENCE: 227

Asp Trp Cys Asp Thr Ile Ile Pro Gly Arg Thr Cys His Gly
1               5                   10

<210> SEQ ID NO 228
<211> LENGTH: 12
<212> TYPE: PRT
<213> ORGANISM: artificial sequence
<220> FEATURE:
<223> OTHER INFORMATION: Synthetic construct

<400> SEQUENCE: 228

Ala Leu Pro Arg Ile Ala Asn Thr Trp Ser Pro Ser
1               5                   10

<210> SEQ ID NO 229
<211> LENGTH: 12
<212> TYPE: PRT
<213> ORGANISM: artificial sequence
<220> FEATURE:
<223> OTHER INFORMATION: Synthetic construct

<400> SEQUENCE: 229

Tyr Pro Ser Phe Ser Pro Thr Tyr Arg Pro Ala Phe
1               5                   10

<210> SEQ ID NO 230
<211> LENGTH: 20
<212> TYPE: PRT
<213> ORGANISM: artificial sequence
<220> FEATURE:
<223> OTHER INFORMATION: Synthetic construct

<400> SEQUENCE: 230

Ala His Pro Glu Ser Leu Gly Ile Lys Tyr Ala Leu Asp Gly Asn Ser
1               5                   10                  15

Asp Pro His Ala
            20

<210> SEQ ID NO 231
```

```
<211> LENGTH: 20
<212> TYPE: PRT
<213> ORGANISM: artificial sequence
<220> FEATURE:
<223> OTHER INFORMATION: Synthetic construct

<400> SEQUENCE: 231

Ala Ser Val Ser Asn Tyr Pro Pro Ile His His Leu Ala Thr Ser Asn
1               5                   10                  15

Thr Thr Val Asn
            20

<210> SEQ ID NO 232
<211> LENGTH: 14
<212> TYPE: PRT
<213> ORGANISM: artificial sequence
<220> FEATURE:
<223> OTHER INFORMATION: Synthetic construct

<400> SEQUENCE: 232

Asp Glu Cys Met Glu Pro Leu Asn Ala Ala His Cys Trp Arg
1               5                   10

<210> SEQ ID NO 233
<211> LENGTH: 14
<212> TYPE: PRT
<213> ORGANISM: artificial sequence
<220> FEATURE:
<223> OTHER INFORMATION: Synthetic construct

<400> SEQUENCE: 233

Asp Glu Cys Met His Gly Ser Asp Val Glu Phe Cys Thr Ser
1               5                   10

<210> SEQ ID NO 234
<211> LENGTH: 14
<212> TYPE: PRT
<213> ORGANISM: artificial sequence
<220> FEATURE:
<223> OTHER INFORMATION: Synthetic construct

<400> SEQUENCE: 234

Asp Leu Cys Ser Met Gln Met Met Asn Thr Gly Cys His Tyr
1               5                   10

<210> SEQ ID NO 235
<211> LENGTH: 14
<212> TYPE: PRT
<213> ORGANISM: artificial sequence
<220> FEATURE:
<223> OTHER INFORMATION: Synthetic construct

<400> SEQUENCE: 235

Asp Leu Cys Ser Ser Pro Ser Thr Trp Gly Ser Cys Ile Arg
1               5                   10

<210> SEQ ID NO 236
<211> LENGTH: 20
<212> TYPE: PRT
<213> ORGANISM: artificial sequence
<220> FEATURE:
<223> OTHER INFORMATION: Synthetic construct

<400> SEQUENCE: 236

Asp Pro Asn Glu Ser Asn Tyr Glu Asn Ala Thr Thr Val Ser Gln Pro
1               5                   10                  15

Thr Arg His Leu
```

20

<210> SEQ ID NO 237
<211> LENGTH: 20
<212> TYPE: PRT
<213> ORGANISM: artificial sequence
<220> FEATURE:
<223> OTHER INFORMATION: Synthetic construct

<400> SEQUENCE: 237

Glu Pro Thr His Pro Thr Met Arg Ala Gln Met His Gln Ser Leu Arg
1               5                   10                  15

Ser Ser Ser Pro
            20

<210> SEQ ID NO 238
<211> LENGTH: 20
<212> TYPE: PRT
<213> ORGANISM: artificial sequence
<220> FEATURE:
<223> OTHER INFORMATION: Synthetic construct

<400> SEQUENCE: 238

Gly Asn Thr Asp Thr Thr Pro Pro Asn Ala Val Met Glu Pro Thr Val
1               5                   10                  15

Gln His Lys Trp
            20

<210> SEQ ID NO 239
<211> LENGTH: 15
<212> TYPE: PRT
<213> ORGANISM: artificial sequence
<220> FEATURE:
<223> OTHER INFORMATION: Synthetic construct

<400> SEQUENCE: 239

Asn Gly Pro Asp Met Val Gln Ser Val Gly Lys His Lys Asn Ser
1               5                   10                  15

<210> SEQ ID NO 240
<211> LENGTH: 15
<212> TYPE: PRT
<213> ORGANISM: artificial sequence
<220> FEATURE:
<223> OTHER INFORMATION: Synthetic construct

<400> SEQUENCE: 240

Asn Gly Pro Glu Val Arg Gln Ile Pro Ala Asn Phe Glu Lys Leu
1               5                   10                  15

<210> SEQ ID NO 241
<211> LENGTH: 20
<212> TYPE: PRT
<213> ORGANISM: artificial sequence
<220> FEATURE:
<223> OTHER INFORMATION: Synthetic construct

<400> SEQUENCE: 241

Asn Asn Thr Ser Ala Asp Asn Pro Pro Glu Thr Asp Ser Lys His His
1               5                   10                  15

Leu Ser Met Ser
            20

<210> SEQ ID NO 242
<211> LENGTH: 20
<212> TYPE: PRT

-continued

```
<213> ORGANISM: artificial sequence
<220> FEATURE:
<223> OTHER INFORMATION: Synthetic construct

<400> SEQUENCE: 242

Asn Asn Thr Trp Pro Glu Gly Ala Gly His Thr Met Pro Ser Thr Asn
1               5                   10                  15

Ile Arg Gln Ala
            20

<210> SEQ ID NO 243
<211> LENGTH: 20
<212> TYPE: PRT
<213> ORGANISM: artificial sequence
<220> FEATURE:
<223> OTHER INFORMATION: Synthetic construct

<400> SEQUENCE: 243

Asn Pro Thr Ala Thr Pro His Met Lys Asp Pro Met His Ser Asn Ala
1               5                   10                  15

His Ser Ser Ala
            20

<210> SEQ ID NO 244
<211> LENGTH: 20
<212> TYPE: PRT
<213> ORGANISM: artificial sequence
<220> FEATURE:
<223> OTHER INFORMATION: Synthetic construct

<400> SEQUENCE: 244

Asn Pro Thr Asp His Ile Pro Ala Asn Ser Thr Asn Ser Arg Val Ser
1               5                   10                  15

Lys Gly Asn Thr
            20

<210> SEQ ID NO 245
<211> LENGTH: 15
<212> TYPE: PRT
<213> ORGANISM: artificial sequence
<220> FEATURE:
<223> OTHER INFORMATION: Synthetic construct

<400> SEQUENCE: 245

Asn Pro Thr Asp Ser Thr His Met Met His Ala Arg Asn His Glu
1               5                   10                  15

<210> SEQ ID NO 246
<211> LENGTH: 14
<212> TYPE: PRT
<213> ORGANISM: artificial sequence
<220> FEATURE:
<223> OTHER INFORMATION: Synthetic construct

<400> SEQUENCE: 246

Gln His Cys Ile Thr Glu Arg Leu His Pro Pro Cys Thr Lys
1               5                   10

<210> SEQ ID NO 247
<211> LENGTH: 14
<212> TYPE: PRT
<213> ORGANISM: artificial sequence
<220> FEATURE:
<223> OTHER INFORMATION: Synthetic construct

<400> SEQUENCE: 247
```

```
Thr Pro Cys Ala Pro Ala Ser Phe Asn Pro His Cys Ser Arg
1               5                   10

<210> SEQ ID NO 248
<211> LENGTH: 14
<212> TYPE: PRT
<213> ORGANISM: artificial sequence
<220> FEATURE:
<223> OTHER INFORMATION: Synthetic construct

<400> SEQUENCE: 248

Thr Pro Cys Ala Thr Tyr Pro His Phe Ser Gly Cys Arg Ala
1               5                   10

<210> SEQ ID NO 249
<211> LENGTH: 20
<212> TYPE: PRT
<213> ORGANISM: artificial sequence
<220> FEATURE:
<223> OTHER INFORMATION: Synthetic construct

<400> SEQUENCE: 249

Trp Cys Thr Asp Phe Cys Thr Arg Ser Thr Pro Thr Ser Thr Ser Arg
1               5                   10                  15

Ser Thr Thr Ser
            20

<210> SEQ ID NO 250
<211> LENGTH: 20
<212> TYPE: PRT
<213> ORGANISM: artificial sequence
<220> FEATURE:
<223> OTHER INFORMATION: Synthetic construct

<400> SEQUENCE: 250

Ala Pro Pro Leu Lys Thr Tyr Met Gln Glu Arg Glu Leu Thr Met Ser
1               5                   10                  15

Gln Asn Lys Asp
            20

<210> SEQ ID NO 251
<211> LENGTH: 20
<212> TYPE: PRT
<213> ORGANISM: artificial sequence
<220> FEATURE:
<223> OTHER INFORMATION: Synthetic construct

<400> SEQUENCE: 251

Glu Pro Pro Thr Arg Thr Arg Val Asn Asn His Thr Val Thr Val Gln
1               5                   10                  15

Ala Gln Gln His
            20

<210> SEQ ID NO 252
<211> LENGTH: 14
<212> TYPE: PRT
<213> ORGANISM: artificial sequence
<220> FEATURE:
<223> OTHER INFORMATION: Synthetic construct

<400> SEQUENCE: 252

Gly Tyr Cys Leu Arg Gly Asp Glu Pro Ala Val Cys Ser Gly
1               5                   10

<210> SEQ ID NO 253
<211> LENGTH: 20
```

```
<212> TYPE: PRT
<213> ORGANISM: artificial sequence
<220> FEATURE:
<223> OTHER INFORMATION: Synthetic construct

<400> SEQUENCE: 253

Leu Ser Ser Lys Asp Phe Gly Val Thr Asn Thr Asp Gln Arg Thr Tyr
1               5                   10                  15

Asp Tyr Thr Thr
            20

<210> SEQ ID NO 254
<211> LENGTH: 14
<212> TYPE: PRT
<213> ORGANISM: artificial sequence
<220> FEATURE:
<223> OTHER INFORMATION: Synthetic construct

<400> SEQUENCE: 254

Asn Phe Cys Glu Thr Gln Leu Asp Leu Ser Val Cys Thr Val
1               5                   10

<210> SEQ ID NO 255
<211> LENGTH: 14
<212> TYPE: PRT
<213> ORGANISM: artificial sequence
<220> FEATURE:
<223> OTHER INFORMATION: Synthetic construct

<400> SEQUENCE: 255

Asn Thr Cys Gln Pro Thr Lys Asn Ala Thr Pro Cys Ser Ala
1               5                   10

<210> SEQ ID NO 256
<211> LENGTH: 20
<212> TYPE: PRT
<213> ORGANISM: artificial sequence
<220> FEATURE:
<223> OTHER INFORMATION: Synthetic construct

<400> SEQUENCE: 256

Pro Ser Glu Pro Glu Arg Arg Asp Arg Asn Ile Ala Ala Asn Ala Gly
1               5                   10                  15

Arg Phe Asn Thr
            20

<210> SEQ ID NO 257
<211> LENGTH: 18
<212> TYPE: PRT
<213> ORGANISM: artificial sequence
<220> FEATURE:
<223> OTHER INFORMATION: Synthetic construct

<400> SEQUENCE: 257

Thr His Asn Met Ser His Phe Pro Pro Ser Gly His Pro Lys Arg Thr
1               5                   10                  15

Ala Thr

<210> SEQ ID NO 258
<211> LENGTH: 14
<212> TYPE: PRT
<213> ORGANISM: artificial sequence
<220> FEATURE:
<223> OTHER INFORMATION: Synthetic construct

<400> SEQUENCE: 258
```

```
Thr Thr Cys Pro Thr Met Gly Thr Tyr His Val Cys Trp Leu
1               5                   10
```

<210> SEQ ID NO 259
<211> LENGTH: 20
<212> TYPE: PRT
<213> ORGANISM: artificial sequence
<220> FEATURE:
<223> OTHER INFORMATION: Synthetic construct

<400> SEQUENCE: 259

```
Tyr Cys Ala Asp His Thr Pro Asp Pro Ala Asn Pro Asn Lys Ile Cys
1               5                   10                  15

Gly Tyr Ser His
            20
```

<210> SEQ ID NO 260
<211> LENGTH: 20
<212> TYPE: PRT
<213> ORGANISM: artificial sequence
<220> FEATURE:
<223> OTHER INFORMATION: Synthetic construct

<400> SEQUENCE: 260

```
Ala Ala Asn Pro His Thr Glu Trp Asp Arg Asp Ala Phe Gln Leu Ala
1               5                   10                  15

Met Pro Pro Lys
            20
```

<210> SEQ ID NO 261
<211> LENGTH: 20
<212> TYPE: PRT
<213> ORGANISM: artificial sequence
<220> FEATURE:
<223> OTHER INFORMATION: Synthetic construct

<400> SEQUENCE: 261

```
Asp Leu His Pro Met Asp Pro Ser Asn Lys Arg Pro Asp Asn Pro Ser
1               5                   10                  15

Asp Leu His Thr
            20
```

<210> SEQ ID NO 262
<211> LENGTH: 14
<212> TYPE: PRT
<213> ORGANISM: artificial sequence
<220> FEATURE:
<223> OTHER INFORMATION: Synthetic construct

<400> SEQUENCE: 262

```
Glu Ser Cys Val Ser Asn Ala Leu Met Asn Gln Cys Ile Tyr
1               5                   10
```

<210> SEQ ID NO 263
<211> LENGTH: 20
<212> TYPE: PRT
<213> ORGANISM: artificial sequence
<220> FEATURE:
<223> OTHER INFORMATION: Synthetic construct

<400> SEQUENCE: 263

```
His Asn Lys Ala Asp Ser Trp Asp Pro Asp Leu Pro Pro His Ala Gly
1               5                   10                  15

Met Ser Leu Gly
            20
```

```
<210> SEQ ID NO 264
<211> LENGTH: 20
<212> TYPE: PRT
<213> ORGANISM: artificial sequence
<220> FEATURE:
<223> OTHER INFORMATION: Synthetic construct

<400> SEQUENCE: 264

Leu Asn Asp Gln Arg Lys Pro Gly Pro Pro Thr Met Pro Thr His Ser
1               5                   10                  15

Pro Ala Val Gly
            20

<210> SEQ ID NO 265
<211> LENGTH: 14
<212> TYPE: PRT
<213> ORGANISM: artificial sequence
<220> FEATURE:
<223> OTHER INFORMATION: Synthetic construct

<400> SEQUENCE: 265

Asn Thr Cys Ala Thr Ser Pro Asn Ser Tyr Thr Cys Ser Asn
1               5                   10

<210> SEQ ID NO 266
<211> LENGTH: 14
<212> TYPE: PRT
<213> ORGANISM: artificial sequence
<220> FEATURE:
<223> OTHER INFORMATION: Synthetic construct

<400> SEQUENCE: 266

Ser Asp Cys Thr Ala Gly Leu Val Pro Pro Leu Cys Ala Thr
1               5                   10

<210> SEQ ID NO 267
<211> LENGTH: 20
<212> TYPE: PRT
<213> ORGANISM: artificial sequence
<220> FEATURE:
<223> OTHER INFORMATION: Synthetic construct

<400> SEQUENCE: 267

Thr Ile Glu Ser Ser Gln His Ser Arg Thr His Gln Gln Asn Tyr Gly
1               5                   10                  15

Ser Thr Lys Thr
            20

<210> SEQ ID NO 268
<211> LENGTH: 20
<212> TYPE: PRT
<213> ORGANISM: artificial sequence
<220> FEATURE:
<223> OTHER INFORMATION: Synthetic construct

<400> SEQUENCE: 268

Val Gly Thr Met Lys Gln His Pro Thr Thr Thr Gln Pro Pro Arg Val
1               5                   10                  15

Ser Ala Thr Asn
            20

<210> SEQ ID NO 269
<211> LENGTH: 20
<212> TYPE: PRT
<213> ORGANISM: artificial sequence
<220> FEATURE:
```

-continued

```
<223> OTHER INFORMATION: Synthetic construct

<400> SEQUENCE: 269

Tyr Ser Glu Thr Pro Asn Asp Gln Lys Pro Asn Pro His Tyr Lys Val
1               5                   10                  15

Ser Gly Thr Lys
            20

<210> SEQ ID NO 270
<211> LENGTH: 8
<212> TYPE: PRT
<213> ORGANISM: Artificial Sequence
<220> FEATURE:
<223> OTHER INFORMATION: Caspase 3 cleavage site

<400> SEQUENCE: 270

Leu Glu Ser Gly Asp Glu Val Asp
1               5
```

MUTANT ARABINOSE PROMOTER FOR INDUCIBLE GENE EXPRESSION

FIELD OF THE INVENTION

The invention relates generally to the field of recombinant DNA technology and microbial protein expression and specifically to an arabinose inducible expression system comprising a modified araB promoter that is operably-linked to a coding region of interest and wherein the modified araB promoter significantly increases its corresponding protein yield relative to the protein yield of the wild type araB promoter under similar expression conditions.

BACKGROUND OF THE INVENTION

Genetic information encoded in DNA molecules is expressed by a series of steps involving transcription of DNA into mRNA and the subsequent translation of the mRNA into polypeptides or proteins. The expression of the encoded information to form polypeptides is initiated at the promoter site, a region on the DNA molecule to which RNA polymerase binds and initiates transcription.

Recombinant production of proteins and peptides has become a hallmark of the biomedical and industrial biochemical industry. One of the factors influencing the cost of commercial protein/peptide production is the efficient expression of the desired gene product. Factors influencing the efficiency of the process include, but are lot limited to gene dosage (i.e. copy number), promoter strength, and the ability to control expression (i.e. inducibility).

Historically, one means to increase protein production has been the use of multi-copy plasmids. However, the increased metabolic burden placed on the cell often results in a decreased growth rate and plasmid instability. As such, it is desirable to use a strong promoter so that the copy number is minimized. The use of a strong promoter facilitates increased protein production while minimizing the metabolic burden on the host cell (i.e. fewer copies of the gene targeted for expression are required to achieve the same level of protein yield).

The use of strong promoters often requires a level of control when expressing the desired gene product. Uncontrolled constitutive expression often results in undesirable effects on the growth and/or viability of the recombinant host cell. As such, the use of strong, inducible promoters is desired. Preferably, the promoter used is characterized by tightly regulated expression and is induced using a condition or compound that is safe, environmentally friendly, and economical.

The araB gene and its promoter ("araB promoter" also known as the $P_{BAD}$ promoter) are located in the L-arabinose operon. The endogenous L-arabinose operon has been studied in various microorganisms including, but not limited to *Escherichia coli, Salmonella typhimurium*, and *Bacillus subtilis* ((Horwitiz et al., *Gene* (1981) 14:309-319; Lin et al., *Gene* (1985) 34:111-122; Lin et al. *Gene* (1985) 34:123-128; Lin et al., *Gene* (1985) 34: 129-134); Schleif, R., *Trends in Genet.* (2000) 16(12):559-565; U.S. Pat. Nos. 5,028,530; and 6,030,807). The operon is comprised of 3 structural genes (araA, araB, and araD) encoding enzymes responsible for converting L-arabinose to D-xylose-5-phosphate. The gene araA encodes the enzyme arabinose isomerase, responsible for converting arabinose to ribulose. Ribulokinase (encoded by the gene araB) phosphorylates ribulose to make ribulose-5-phosphate. The enzyme ribulose-5-phosphate epimerase (encoded by the gene araD) converts ribulose-5-phosphate to xylulose-5-phosphate, which can be metabolized via the pentose phosphate pathway. The araBAD operon is coordinately controlled by the inducer L-arabinose and the AraC regulatory gene product (Guzman et al., (1995) *J. Bacteriol.* 177: 4121-4130). $P_{BAD}$ based expression systems based are widely used and commercially available from companies such as Invitrogen (Carlsbad, Calif.).

The $P_{BAD}$ expression system is tightly controlled and the inducer, L-arabinose, is safe and economical. However, the wild type araB promoter is not generally considered a strong promoter once induced. As such, use of the currently available $P_{BAD}$-based expression systems is often unattractive for low cost peptide/protein production where optimal protein yield is desired.

The problem to be solved is to provide an arabinose inducible expression system having the ability to increase protein yield when operably linked to a coding sequence of interest.

SUMMARY OF THE INVENTION

The stated problem has been solved through the discovery of a mutant araB promoter that, when operably-linked to a coding region of interest, improves the yield of the corresponding gene product. The mutant promoter, when operably-linked to an AraC transcription factor binding region, exhibits tightly regulated and inducible expression in an AraC+ microbial host cell.

Several structurally similar mutant araB promoters have been identified. A consensus nucleic acid sequence representative of the conserved structure is provided by SEQ ID NO: 2.

The present mutant araB promoter can be operably linked to additional regulatory elements, which are referred to herein as an "AraC transcription factor binding region", located upstream—in the 5' direction— of the present promoter, and which provide the tightly regulated and inducible control associated with commercially available $P_{BAD}$-based expression systems. Further, a nucleic acid molecule encoding an araB expression system comprises the provided AraC transcription factor binding region operably linked to SEQ ID NO: 2.

Described herein is an arabinose-inducible expression cassette comprising:
  a) an AraC transcription factor binding region;
  b) an araB promoter of SEQ ID NO: 2; and
  c) a coding region of interest;
  wherein the AraC transcription factor binding region, the araB promoter, and the coding region of interest are in operable linkage.

Also described herein is a vector comprising the arabinose-inducible expression cassette.

Typically, the AraC transcription factor is provided by including at least one expressible copy of an araC gene in a recombinant microbial host cell, preferably, on an expression vector. Moreover, a vector comprising the present araB expression system may further comprise an expressible copy of the araC gene.

The AraC transcription factor binding region may comprise nucleic acid sequence SEQ ID NO: 33.

A microbial host cell comprising the present vector is also provided and the vector may comprise at least one transcription terminator, which may comprise SEQ ID NO: 28.

Also described herein are methods to produce a target gene product in a recombinant microbial host cell comprising:
  a) providing a recombinant microbial host cell comprising an L-arabinose inducible expression system, said expression system comprising:
    i) a nucleic acid molecule encoding a chimeric gene, said chimeric gene comprising at least one copy of the present araB expression system, said araB expression system comprising the araB promoter of SEQ ID NO: 2 operably linked to a coding region of interest encoding a target gene product;

ii) at least one expressible copy of an araC gene encoding an AraC regulatory protein;

b) contacting said recombinant microbial host cell with an effective amount of L-arabinose, whereby said chimeric gene is expressed and the target gene product is produced; and c) optionally isolating the target gene product produced in step (b).

Increasing the strength of a promoter is important to reducing the cost of producing a desired gene product. Use of the present araB promoter is particularly attractive when producing small bioactive peptides that typically do not require a specific tertiary structure for activity, i.e. complex folding often associated with larger enzymes. The cost of producing and isolating small peptides is often limited due to their solubility and the endogenous protease activity of the host cell; that is, the small, soluble peptides are often proteolytically degraded. Because of this, it is desirable to produce small peptides in the form of inclusion bodies by producing the peptides as fusion peptides. The fusion peptides are comprised of the small peptide of interest fused to one or more solubility tags ("inclusion body tags"). The present arabinose inducible expression system may be operably linked to a coding region of interest encoding at least one fusion peptide. Preferably, the fusion peptide comprises an inclusion body tag linked to a peptide of interest, wherein the peptide of interest comprises at least one domain having affinity for at least one body surface and is also known as a "body surface-binding peptide".

BRIEF DESCRIPTION OF THE FIGURES

FIG. 2 is a CLUSTALW (version 1.83) multiple sequence alignment of 8 selected mutants. The alignment shows that the −10 region of all the sequenced constructs from the library had different sequences (underlined region). The −35 region of all the constructs remains wild type. About half the constructs had deletions around the ribosome binding site (RBS).

FIG. 3 is a CLUSTALW (version 1.83) multiple sequence alignment of various mutant araB promoter sequences and the sequence of the wild type araB promoter. Mutant GFP B1 ["B1"]; (SEQ ID NO: 17) was the brightest mutant sequence accounting for approximately 20% of the brightest cells. Mutants GFP M1 (SEQ ID NO: 18), M2 (SEQ ID NO: 19), and M3 (SEQ ID NO: 20) were less fluorescent than Mutant GFP B1 (SEQ ID NO: 17) but more fluorescent than the wild type araB promoter sequence (SEQ ID NO: 1).

FIG. 5 is a CLUSTALW (version 1.83) alignment of several mutant araB promoter sequences and the resulting consensus sequence (SEQ ID NO: 2) of the present araB promoter.

BRIEF DESCRIPTION OF THE BIOLOGICAL SEQUENCES

Figure 1:
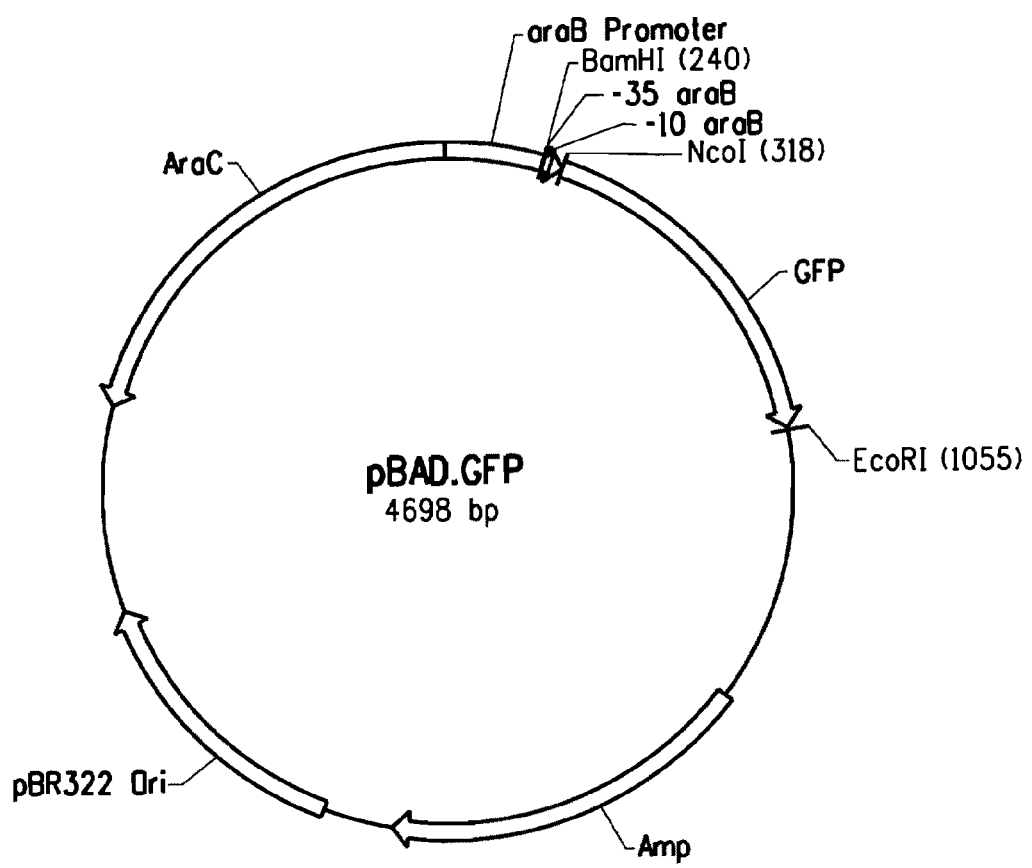
FIG. 1 is a plasmid map of plasmid pBAD.GFP. The NcoI-EcoRI, restriction fragment encoding for GFP gene (coding region provided by SEQ ID NO: 6) from plasmid pAcGFP (Clontech, Mountainview, Calif.) was subcloned into the NcoI and EcoRI sites of plasmid pBAD.HisB (Invitrogen, Carlsbad, Calif.; SEQ ID NO: 5) to yield plasmid pBAD.GFP (SEQ ID NO: 8).

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPC and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the nucleic acid sequence of the wild-type araB promoter from pBAD-HisB (Invitrogen).

SEQ ID NO: 2 is the nucleic acid sequence of the consensus sequence of the present mutant araB promoter.

SEQ ID NO: 3 is the nucleic acid sequence of "Primer 1".

SEQ ID NO: 4 is the nucleic acid sequence of "Primer 2".

SEQ ID NO: 5 is the nucleic acid sequence of plasmid pBAD-HisB.

SEQ ID NO: 6 is the nucleic acid sequence of the coding region encoding the Green Fluorescence Protein (GFP).

SEQ ID NO: 7 is the amino acid sequence of GFP encoded by plasmid pBAD.GFP.

SEQ ID NO: 8 is the nucleic acid sequence of plasmid pBAD.GFP.

SEQ ID NO: 9 is the nucleic acid sequence of mutant araB promoter "mut1".

SEQ ID NO: 10 is the nucleic acid sequence of mutant araB promoter "mut2".

SEQ ID NO: 11 is the nucleic acid sequence of mutant araB promoter "mut3".

SEQ ID NO: 12 is the nucleic acid sequence of mutant araB promoter "mut4".

SEQ ID NO: 13 is the nucleic acid sequence of mutant araB promoter "mut5".

SEQ ID NO: 14 is the nucleic acid sequence of mutant araB promoter "mut6".

SEQ ID NO: 15 is the nucleic acid sequence of mutant araB promoter "mut7".

SEQ ID NO: 16 is the nucleic acid sequence of mutant araB promoter "mut8".

SEQ ID NO: 17 is the nucleic acid sequence of mutant araB promoter GFP.B1 (also referred to herein as "araB1").

SEQ ID NO: 18 is the nucleic acid sequence of mutant araB promoter GFP.M1.

SEQ ID NO: 19 is the nucleic acid sequence of mutant araB promoter GFP.M2

SEQ ID NO: 20 is the nucleic acid sequence of mutant araB promoter GFP.M3.

SEQ ID NO: 21 is the amino acid sequence of the N-terminus addition associated with promoter araB GFP.B1.

SEQ ID NO: 22 is the nucleic acid sequence of mutant araB promoter GFP.1B (also referred to herein as promoter "ara1b").

SEQ ID NO: 23 is the nucleic acid sequence of mutant araB promoter GFP.4a (also referred to herein as promoter "ara4a").

SEQ ID NO: 24 is the nucleic acid sequence of mutant araB promoter GFP.5a (also referred to herein as promoter "ara5a").

SEQ ID NO: 25 is the nucleic acid sequence of mutant araB promoter GFP.8a (also referred to herein as promoter "ara8a").

SEQ ID NO: 26 is the nucleic acid sequence of the coding region of the araC gene.

SEQ ID NO: 27 is the amino acid sequence of the AraC protein.

SEQ ID NO: 28 is the nucleic acid sequence of the transcription terminator rrnB $T_1$ and $T_2$.

SEQ ID NO: 29 is the nucleic acid sequence of an $O_2$ binding site within an araB expression system.

SEQ ID NO: 30 is the nucleic acid sequence an $O_1$ binding site within an araB expression system.

SEQ ID NO: 31 is the nucleic acid sequence of the CRP protein binding site within an araB expression system.

SEQ ID NO: 32 is the nucleic acid sequence of the AraC $I_1/I_2$ binding site within an araB expression system.

SEQ ID NO: 33 is the nucleic acid sequence of an AraC transcription factor binding region located upstream (5') of an araB promoter. The AraC transcription factor binding region can be operably linked to an araB promoter to form an araB expression system.

SEQ ID NO: 34 is the nucleic acid sequence of an araB expression system comprising the AraC transcription factor binding region of SEQ ID NO: 33 operably linked to SEQ ID NO: 2.

SEQ ID NO: 35 is the nucleic acid sequence of an araB expression system comprising the AraC transcription factor binding region of SEQ ID NO: 33 operably linked to SEQ ID NO: 17.

SEQ ID NO: 36 is the nucleic acid sequence of an araB expression system comprising the AraC transcription factor binding region of SEQ ID NO: 33 operably linked to SEQ ID NO: 22.

SEQ ID NO: 37 is the nucleic acid sequence of an araB expression system comprising the AraC transcription factor binding region of SEQ ID NO: 33 operably linked to SEQ ID NO: 23.

SEQ ID NO: 38 is the nucleic acid sequence of an araB expression system comprising the AraC transcription factor binding region of SEQ ID NO: 33 operably linked to SEQ ID NO: 24.

SEQ ID NO: 39 is the nucleic acid sequence of an araB expression system comprising the AraC transcription factor binding region of SEQ ID NO: 33 operably linked to SEQ ID NO: 25.

SEQ ID NO: 40 is the nucleic acid sequence of primer "Ara1F".

SEQ ID NO: 41 is the nucleic acid sequence of primer "Ara1R".

SEQ ID NO: 42 is the nucleic acid sequence of primer "Ara5F".

SEQ ID NO: 43 is the nucleic acid sequence of primer "Ara5R".

SEQ ID NO: 44 is the nucleic acid sequence of primer "Ara8F".

SEQ ID NO: 45 is the nucleic acid sequence of primer "Ara8R".

SEQ ID NOs: 46-179 are the amino acid sequences of various hair-binding peptides.

SEQ ID NOs: 175-227 are the amino acid sequences of various skin-binding peptides.

SEQ ID NOs: 228-229 are the amino acid sequences of various nail-binding peptides.

SEQ ID NOs: 230-269 are the amino acid sequences of various teeth-binding peptides.

SEQ ID NO: 270 is the nucleic acid sequence of the Caspase-3 cleavage sequence.

DETAILED DESCRIPTION OF THE INVENTION

The present invention provides an arabinose inducible expression system comprising the present araB promoter (SEQ ID NO: 2). The present arabinose inducible expression system is characterized by a improvement in protein yield in comparison to the commercially available $P_{BAD}$ expression system from which it was derived.

The following definitions are used herein and should be referred to for interpretation of the claims and the specification.

As used herein, the terms "comprises," "comprising," "includes," "including," "has," "having," "contains" or "containing," or any other variation thereof, are intended to cover a non-exclusive inclusion.

This means a composition, a mixture, process, method, article, or apparatus that comprises a list of elements is not limited to only those elements but may include others not expressly listed or inherent to it. As used herein, "or" refers to an inclusive and an exclusive "or". For example, a condition A or B is satisfied by any one of the following: A is true (or present) and B is false (or not present), A is false (or not present) and B is true (or present), and both A and B are true (or present).

As used herein, the indefinite articles "a" and "an" preceding an element of the invention do not refer to a specific number of instances of the element within the recited invention. "A" or "an" include one or at least one or "one or more than one", and the singular word form of the element or component also includes the plural unless the number is obviously meant to be singular.

As used herein, the term "about" refers to modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like.

"About" also encompasses amounts that differ due to different equilibrium conditions for a composition resulting from a particular initial mixture. Whether or not modified by the term "about", the claims include equivalents to the quantities.

As used herein, the term "invention" or "present invention" is a non-limiting term and does not refer to any single variation of an invention described herein but encompasses all possible variations described in the specification and defined by the claims.

"Open reading frame" is abbreviated ORF.

"Polymerase chain reaction" is abbreviated PCR.

As used herein, the term "arabinose" refers to L-arabinose as well as all synonyms of compounds classified under CAS # 87-79-9. L-arabinose is used to induce and control expression in the present arabinose expression system.

As used herein, the terms "arabinose expression system", "arabinose inducible expression system", and "araB expression system" refers to the combination of genetic elements associated with L-arabinose inducible expression and includes (1) an expressible copy of the araC gene and its corresponding gene product (AraC), (2) suitable regulatory region wherein the AraC transcription regulator can bind and exhibit the tightly-regulated and inducible expression associated with commercially available $P_{BAD}$-based expression systems, and (3) a promoter, that is, the "arabinose promoter", capable of promoting transcription when operably-linked to a target coding region of interest.

As used herein, the terms "tightly regulated" and "tightly controlled" refer to an arabinose expression system that is easily modulated and controlled by the presence of an effective concentration of arabinose. Expression activity is dependent upon the presence of an effective concentration of arabinose.

Arabinose operon and expression systems based on the wild type E. coli promoter are well known in the art (Schleif, R., Trends in Genet. (2000) 16:559-565). Expression vectors based on the wild type arabinose expression system are commercially available (for example, PBAD-based expression vectors from Invitrogen). As used herein, the term "wild-type araB promoter" will refer to a nucleic acid molecule having a nucleic acid sequence as provided by SEQ ID NO: 1 (the sequence of the araB promoter used in the commercially available vector pBAD-HisB from Invitrogen (Carlsbad, Calif.)).

As used herein, the term "mutant araB promoter having the consensus sequence of SEQ ID NO: 2" comprises a nucleic acid sequence longer than the wild type araB promoter sequence (SEQ ID NO: 1). The present mutant araB promoter is characterized by the ability to increase peptide production at least a 2-fold, preferably a 5-fold, and most preferably at least a 1 0-fold relative to the amount of protein produced by the wild type araB promoter under substantially identical reaction conditions.

As used herein, the term "AraC" will refer to the transcription factor protein capable of binding to various sites within the arabinose inducible expression system described herein. The araC gene (SEQ ID NO: 26) encodes the AraC protein (SEQ ID NO: 27). The mechanism of AraC transcription factor control of the araBAD operon is well known (Schleif, R., supra). An arabinose inducible expression system comprising the present araB promoter is used in a microbial host cell that produces an effective amount of the AraC protein. The expressible araC gene may be expressed either chromosomally or extrachromosomally, such as by a plasmid. Preferably, the expressible araC gene resides on a vector further comprising the present araB promoter.

As used herein, the term "AraC+" microbial host cell refers to any microbial host cell that produces an effective amount of the AraC protein.

As used herein, the terms "effective amount of AraC" or "effective concentration of AraC" refers to that amount or concentration of AraC regulatory protein within the microbial host that inhibits transcription of the araB promoter system in the absence of an effective amount of L-arabinose.

As used herein, the terms "effective amount of L-arabinose" or "effective concentration of L-arabinose" refers to the amount or concentration of L-arabinose that induces expression of the heterologous gene. The amount of L-arabinose added to the culture medium may vary but typically provides an L-arabinose concentration ranging from 0.00002% to 20%, preferably 0.002% to 2%, and most preferably about 0.01% to 0.5%. It is well known in the art to determine the effective amount or concentration of AraC and L-arabinose required to inhibit or promote expression using the present araB promoter system (Guzman et al., supra).

As used herein, the term "operon" refers to a combination of elements including a gene encoding a peptide and the control region which regulates that expression.

As used herein, the term "operator" refers to a DNA sequence capable of interacting with a specific transcription factor, thereby controlling the function of the adjacent gene(s).

As used herein, the term "promoter" refers to a DNA sequence within the control region at which RNA polymerase binds and initiates transcription of the adjacent gene(s), that is, coding regions/target sequences. The present promoter may also include a start codon that introduces a small N-terminal addition to the coding region of interest so long as the function of the gene product encoded by the coding region is retained. Alternatively, the present promoter need not include such a start codon.

As used herein, the term "arabinose promoter" or "araB promoter" refers to a region of DNA known to bind RNA polymerase and initiate transcription and will typically include the region spanning from just upstream (5') the −35 sequence upstream of the actual ribosomal binding site and downstream and up to, but not including, the target coding region. One of skill in the art will recognize that the −35 region will typically include all or a portion of the $I_1/I_2$ AraC binding site (SEQ ID NO: 32). As shown and defined herein, the present arabinose promoter sequence may include an alternative start codon upstream of the target coding region which may add a short N-terminal extension to the resulting peptide. It is well known in the art to determine if the short N-terminal extension adversely affects the target coding sequence gene product.

The consensus sequence of the present mutant araB promoter is provided as SEQ ID NO: 2. As described herein, structurally similar versions of the present mutant araB promoter that do not add a short N-terminal extension to the desired gene product retained the characteristic increase in relative protein yield. The present araB promoter may comprise a nucleic acid molecule having a nucleic acid sequence selected from the group consisting of SEQ ID NOs: 17, 22, 23, 24, and 25.

As used herein, the term "AraC transcription factor binding region" refers to regulatory regions upstream (5') of the present araB promoter which aid in the binding of the transcription factor AraC when inhibiting transcription. This region can include the $O_1$ (SEQ ID NO: 30) and $O_2$ (SEQ ID NO: 29) sites as well as the CRP (cAMP receptor protein; also known a "CAP") binding site (SEQ ID NO: 31). An AraC transcription factor binding region as exemplified herein is SEQ ID NO: 33.

As used herein, the terms "araB promoter control system", "araB promoter system", "araB expression system", and the "arabinose inducible expression system comprising the present promoter" refer to a nucleic acid molecule encoding the AraC transcription factor binding region operably linked to the present mutant araB promoter. The araB promoter system may comprise the AraC transcription factor binding region (SEQ ID NO: 33) operably linked to the consensus sequence of the present araB mutant promoters (SEQ ID NO: 2), resulting in SEQ ID NO: 34. Differently, the araB promoter system may comprise a nucleic acid molecule having a nucleic acid sequence selected from the group consisting of SEQ ID NOs: 34, 35, 36, 37, 38, and 39 or from the group consisting of SEQ ID NOs: 35, 36, 37, 38, and 39.

As used herein, the term "heterologous gene" refers to a gene that is foreign, i.e. originating from a donor different from the host or a chemically synthesized or modified gene and can include a donor of a different species form the host. The gene typically encodes for polypeptides ordinarily not produced by the organism susceptible to transformation.

As used herein, the term "isolated nucleic acid molecule" refers to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the terms "coding region", "coding sequence", "target coding region", and "coding region of interest" refers to a DNA molecule having a DNA sequence that encodes a desired gene product. The coding region of interest is operably linked to the present araB promoter system (i.e. forming a chimeric gene) for L-arabinose induced expression. The coding region typically includes the start codon encoding the first amino acid of the desired gene product. In one embodiment, the present promoter may introduce a start codon 5' to the target coding region, that is, a start codon in addition to the start codon in the target coding region, which is in-frame with the coding region and introduces a small N-terminal addition to the target gene product.

As used herein, the terms "gene product", "target gene product", "target coding region gene product", and "peptide of interest" refer to the desired peptide/protein product encoded by the target coding region. The gene product optionally includes a small N-terminal addition. e.g. 22 amino acids encoded by a promoter region providing an additional start codon so long as the activity/function of the gene product is not adversely affected. Moreover, the target gene product need not include such an N-terminal addition, that is i.e. the promoter region does not include a start codon 5'. The target gene product may include any peptide/protein product including, but not limited to proteins, fusion proteins, enzymes, peptides, polypeptides, and oligopeptides. The target gene product may be a fusion peptide comprising at least one inclusion body tag and at least one target surface-binding peptide. The target surface-binding peptide may be a body surface-binding peptide. The body surface-binding peptide may be selected from the group consisting of hair-binding peptides, skin-binding peptides, nail-binding peptides, and teeth-binding peptides. The body surface-binding peptide may comprise at least one peptide selected from the group consisting of hair-binding peptides having an amino acid sequence as provided by SEQ ID NOs: 46-179, skin-binding peptides having an amino acid sequence as provided by SEQ ID NOs: 175-227, nail-binding peptides having an amino acid sequence as provided by SEQ ID NOs: 228-229, and teeth-binding peptides having an amino acid sequence as provided by SEQ ID NOs: 230-269.

As used herein, the term "body surface-binding peptide" refers to a peptide having high affinity (less than $10^{-5}$ M Kd or less than $10^{-5}$ MB$_{50}$) for a body surface. Examples of body surfaces include, but are not limited to hair, skin, nail, and oral cavity surfaces (teeth, pellicle, gum, tongue, etc.). The body surface-binding peptides are typically used to couple a personal or health care agent to the body surface. These agents include colorants, conditioners, antimicrobials, etc.). Means to identify suitable body-surface binding peptides are well known in the art and may include biopanning techniques such as phage display, bacterial display, yeast display, ribosome display, and mRNA-display, etc. The body surface-binding peptide may be empirically-generated.

As used herein, the term "hair" refers to human hair, eyebrows, and eyelashes.

As used herein, the term "skin" refers to human skin, or substitutes for human skin, such as pig skin, VITRO-SKIN® and EPIDERM™ and refers to a body surface generally comprising a layer of epithelial cells and may additionally comprise a layer of endothelial cells.

As used herein, the term "nails" refers to human fingernails and toenails.

As used herein, the term "pigment" refers to an insoluble, organic or inorganic colorant.

As used herein, "HBP" means hair-binding peptide. An HBP is a peptide that binds with high affinity (less than $10^{-5}$ M Kd) to human hair. Examples of hair binding peptides have been reported (U.S. patent application Ser. No. 11/074473 to Huang et al.; Int'l App. Pub. No. WO 0179479; U.S. Pat. App. No. 2002/0098524 to Murray et al.; U.S. Pat. App. Pub. No. 2003/0152976 to Janssen et al.; Int'l App. Pub. No. WO 04048399; U.S. Pat. App. Pub. Nos. 2007/0067924; and 2007/0249805) and are provided in Table A.

As used herein, "SBP" refers to and is an abbreviation for skin-binding peptide. A SBP is a peptide that binds with high affinity (less than $10^{-5}$ M Kd) to human or mammalian skin. Examples of skin binding peptides are provided in Table A and have been reported in U.S. patent application Ser. No. 11/069858 to Buseman-Williams; Int'l App. Pub. No. WO 2004/000257 to Rothe et. al.; and U.S. Pat. App. Pub. No. 2007/0249805.

As used herein, "NBP" refers to and is an abbreviation for nail-binding peptide. A NBP is a peptide that binds with high affinity (less than $10^{-5}$ M Kd) to human. Examples of nail binding peptides are provided in Table A and have been reported in U.S. Pat. App. Pub. No. 2007/0249805.

As used herein, "TBP" refers to and is an abbreviation for teeth-binding peptide. A TBP is a peptide that binds with high affinity (less than $10^{-5}$ M Kd) to mammalian or human tooth enamel or tooth pellicle, which is a glycoprotein naturally found on the surface of mammalian teeth. Examples of teeth-binding peptides are provided in Table A and have been reported in U.S. patent application Ser. No. 11/877,692.

As used herein, an "antimicrobial peptide" refers to a peptide having the ability to kill microbial cell populations. See U.S. Pat. App. Pub. No. 2007/0249805.

As used herein, the term "inclusion body tag", abbreviated as "IBT" and refers to a polypeptide that facilitates formation of inclusion bodies when fused to a peptide of interest. The peptide of interest is typically soluble within the host cell and/or host cell lysate when not fused to an inclusion body tag. Fusion of the peptide of interest to the inclusion body tag produces a fusion protein that agglomerates into intracellular bodies, also called inclusion bodies, within the host cell. The fusion protein comprises a portion having an inclusion body tag and a peptide/protein of interest. The polypeptide/protein of interest may be separated from the inclusion body tags using cleavable peptide linker elements. See U.S. patent application Ser. Nos. 11/641936, 11/641273, and 11/782836.

As used herein, "cleavable linker elements", "peptide linkers", and "cleavable peptide linkers" are used interchangeably and refer to cleavable peptide segments typically found between inclusion body tags and the peptide of interest. After the inclusion bodies are separated and/or partially-purified or purified from the cell lysate, the cleavable linker elements can be cleaved chemically and/or enzymatically to separate the inclusion body tag from the peptide of interest. The fusion peptide may also include a plurality of regions encoding one or more peptides of interest separated by one or more cleavable peptide linkers. The peptide of interest can then be isolated from the inclusion body tag, if necessary.

The inclusion body tag(s) and the peptide of interest may exhibit different solubilities in a defined medium, typically aqueous, thereby facilitating separation of the inclusion body tag from the peptide of interest. Preferably, the inclusion body tag is insoluble in an aqueous solution while the protein/polypeptide of interest is appreciably soluble in an aqueous solution. The pH, temperature, and/or ionic strength of the aqueous solution can be adjusted to facilitate recovery of the peptide of interest. In a preferred embodiment, the differential solubility between the inclusion body tag and the peptide of interest occurs in an aqueous solution having a pH of 5 to 10 and a temperature range of 15° C. to 50° C. The cleavable peptide linker may be from 1 to about 50 amino acids, preferably from 1 to about 20 amino acids in length. An example of an enzymatically cleavable peptide linker is provided by SEQ ID NO: 270 (Caspase-3 cleavage sequence). In a preferred embodiment, the cleavable linker is an acid cleavable aspartic acid—proline dipeptide (D-P) moiety. The cleavable peptide linkers may be incorporated into the fusion proteins using any number of techniques well known in the art.

As used herein, the term "operably linked" refers to the association of two or more nucleic acid molecules having known function on a single nucleic acid fragment so that the function of one is affected by the presence of the other. For example, a promoter is operably linked with a coding sequence when it is capable of affecting the expression of that coding sequence, that is when the coding sequence is under the transcriptional control of the promoter. "Operably linked" may include the association of the present promoter sequence with well characterized upstream (5') regulatory elements associated with AraC-based transcription control of the L-arabinose operon/expression system. A non-limiting example would be operably linking the present promoter sequence of SEQ ID NO: 2 downstream of a DNA region associated with AraC transcription factor binding and regulatory control (for example, SEQ ID NO: 33 comprising the $O_2$ region (SEQ ID NO: 30) and all and/or portions of the CRP receptor protein binding site (SEQ ID NO: 31) and portion of the $I_1/I_2$ region (SEQ ID NO: 32) not encompassed by the 5' region of the present araB promoter as defined by SEQ ID NO: 2). Chimeric genes may be provided by operably linking (in a 5' to 3' direction) a nucleic acid molecule encoding the AraC transcription factor binding region to the present araB promoter which is further operably linked to a coding region of interest. Such a chimeric gene may further comprise a transcription terminator sequence operably linked to the 3' end of the coding region of interest. The transcription terminator sequence may be the rrnB T1 and T2 terminator provided by SEQ ID NO: 28.

"Operably linked" may also refer to the products of chimeric genes, such as fusion proteins. As such, "operably linked" refers to the linking of an inclusion body tag to a peptide of interest to be produced and recovered. The inclusion body tag is "operably linked" to the peptide of interest if upon expression the fusion protein is insoluble and accumulates in inclusion bodies in the expressing host cell.

As used herein, the terms "fusion protein", "fusion peptide", "chimeric protein", and "chimeric peptide" are interchangeable and refer to a polymer of amino acids (peptide, oligopeptide, polypeptide, or protein) comprising at least two portions, each portion comprising a distinct function. A first portion of the fusion peptide may comprise at least one inclusion body tag and a second portion of the fusion peptide may comprise at least one peptide of interest. The fusion protein may additionally include at least one cleavable peptide linker that facilitates chemical and/or enzymatic cleavage and separation of the inclusion body tag(s) and the peptide(s) of interest.

Means to prepare the present promoters are well known in the art as disclosed in Stewart et al., *Solid Phase Peptide Synthesis, Pierce Chemical* Co., Rockford, Ill., 1984; Bodanszky, *Principles of Peptide Synthesis*, Springer-Verlag, N.Y., 1984; and Pennington et al., *Peptide Synthesis Protocols*, Humana Press, Totowa, N.J., 1994. Preferably, the present promoters and the corresponding chimeric genes, expression cassettes, and vectors may be prepared using recombinant DNA and molecular cloning techniques.

As used herein, the terms "polypeptide" and "peptide" are interchangeable and refer to a polymer of two or more amino acids joined together by a peptide bond, wherein the peptide is of unspecified length, thus, peptides, oligopeptides, polypeptides, and proteins are included within the present definition. This term also includes post expression modifications of the polypeptide, for example, glycosylations, acetylations, phosphorylations and the like. Also included are peptides containing one or more analogues of an amino acid or labeled amino acids and peptidomimetics.

As used herein, the terms "protein of interest", "polypeptide of interest", "peptide of interest", "targeted protein", "target gene product", "target coding region gene product" "targeted polypeptide", "targeted peptide", "expressible protein", and "expressible polypeptide" are interchangeable and refer to a bioactive protein, polypeptide, or peptide that is targeted for expression using the present araB promoter system.

As used herein, the terms "bioactive" or "peptide of interest activity" refer to the activity or characteristic associated with the peptide and/or protein of interest. The bioactive peptides may be used as, for example, curative agents for diseases (e.g., insulin, interferon, interleukins, anti-angiogenic peptides (U.S. Pat. No. 6,815,426); polypeptides that bind to defined cellular targets such as receptors, channels, lipids, cytosolic proteins, and membrane proteins; peptides having antimicrobial activity; peptides having an affinity for a particular material (e.g., hair-binding polypeptides, skin-binding polypeptides, nail-binding polypeptides, cellulose-binding polypeptides, polymer-binding polypeptides, clay-binding polypeptides, silica-binding polypeptides, carbon nanotube-binding polypeptides and peptides that have an affinity for particular animal or plant tissues) for targeted delivery of benefit agents.

As used herein, the term "benefit agent" refers to a molecule that imparts a desired functionality to the complex for a defined application. The benefit agent may be the peptide of interest itself or may be one or more molecules bound to, either covalently or non-covalently, or associated with, the peptide of interest wherein the binding affinity of the targeted polypeptide is used to selectively target the benefit agent to the targeted material. The targeted polypeptide comprises at least one region having an affinity for at least one target material (e.g., biological molecules, polymers, hair, skin, nail, other peptides, etc.) and at least one region having an affinity for the benefit agent (e.g., pharmaceutical agents, pigments, conditioners, dyes, fragrances, etc.). Examples of benefits agents may include, but are not limited to, conditioners for personal care products, pigments, dye, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides).

As used herein, the term "inclusion body" refers to an intracellular amorphous deposit comprising aggregated protein found in the cytoplasm of a cell. Small peptides are typically soluble with the host cell and/or cell lysates can be fused to one or more inclusion body tags to facilitate formation of an insoluble fusion protein. In an alternative embodiment, the peptide may be partially insoluble in the host cell, but produced at relatively lows levels where significant inclusion body formation does not occur. As such, the formation of inclusion bodies will enhance peptide yield.

"Codon degeneracy" refers to the nature in the genetic code permitting variation of the nucleotide sequence without affecting the amino acid sequence of an encoded polypeptide. Accordingly, the instant invention relates to any nucleic acid fragment that encodes the present amino acid sequences. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Miscellaneous (or as defined in the present application) | Xaa | X |

As used herein, the term "gene" refers to a nucleic acid fragment that expresses a specific protein, including regulatory sequences preceding (5' sequences) and following (3' sequences) the coding sequence. "Native gene" refers to a gene as found in nature with its own regulatory sequences "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "foreign" gene refers to a gene not normally found in the host organism, but that is introduced into the host organism by gene transfer. Foreign genes can comprise native genes inserted into a non-native organism, or chimeric genes.

As used herein, the term "coding sequence" refers to a DNA sequence that encodes for a specific amino acid sequence. "Suitable regulatory sequences" refer to nucleotide sequences located upstream (5' sequences), within, or downstream (3' sequences) of a coding sequence, and which influence the transcription, RNA processing or stability, or translation of the associated coding sequence. Regulatory sequences may include promoters, promoter systems (i.e., the promoter region and additional transcription factor binding sites upstream of the promoter required for inducible, controlled expression), enhancers, ribosomal binding sites, translation leader sequences, introns, polyadenylation recognition sequences, RNA processing site, effector binding sites, and stem-loop structures. One of skill in the art recognizes that selection of suitable regulatory sequences will depend upon host cell and/or expression system used.

As used herein, the term "genetic construct" refers to a series of contiguous nucleic acids useful for modulating the genotype or phenotype of an organism. Non-limiting examples of genetic constructs include but are not limited to a nucleic acid molecule, and open reading frame, a gene, an expression cassette, a vector, a plasmid and the like.

As used herein, the term "transformation" refers to the transfer of a nucleic acid fragment into the genome of a host organism. As used herein, the host cell's genome is comprised of chromosomal and extrachromosomal (e.g., plasmid) genes. Host organisms containing the transformed nucleic acid fragments are referred to as "transgenic" or "recombinant" or "transformed" organisms.

As used herein, the term "host cell" refers to cell which has been transformed or transfected, or is capable of transformation or transfection by an exogenous polynucleotide sequence.

As used herein, the terms "plasmid" or "vector" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

Standard recombinant DNA and molecular cloning techniques used herein are well known in the art and are described by Sambrook, J., and Russell, D., *Molecular Cloning: A Laboratory Manual*, Third Edition, Cold Spring Harbor Laboratory Press, Cold Spring Harbor, N.Y. (2001) (hereinafter "Sambrook"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

araB Operon and L-arabinose Inducible Expression Systems

The endogenous L-arabinose operon has been studied in various microorganisms including, but not limited to *Escherichia coli, Salmonella typhimurium*, and *Bacillus subtilis* ((Horwitz et al., Gene (1981) 14:309-319; Lin et al., Gene (1985) 34:111-122; Lin et al. Gene (1985) 34:123-128; Lin et al., Gene (1985) 34: 129-134); Schleif, R. Trends in Genet. (2000) 16:559-565; U.S. Pat. Nos. 5,028,530; and 6,030, 807). The operon is comprised of 3 structural genes (araA, araB, and araD) encoding enzymes responsible for converting L-arabinose to D-xylose-5-phosphate. The gene araA encodes the enzyme arabinose isomerase, responsible for converting arabinose to ribulose. Ribulokinase (encoded by the gene araB) phosphorylates ribulose to make ribulose-5-phosphate. The enzyme ribulose-5-phosphate epimerase (encoded by the gene araD) converts ribulose-5-phosphate to xylulose-5-phosphate, which can be metabolized via the pentose phosphate pathway. The araBAD operon is coordinately controlled by the inducer L-arabinose and the AraC regulatory gene product (Guzman et al., (1995) *J. Bacteriol.* 177: 4121-4130). $P_{BAD}$-based expression systems developed from a wild type araBAD operon (i.e. pBAD expression vectors) are widely used and commercially available from companies such as Invitrogen (Carlsbad, Calif.).

The regulatory control elements and the underlying control mechanism of $P_{BAD}$-based expression systems have been extensively studied (Schleif, R., 2000, supra). The araC gene product (AraC) is a transcription factor that, as a homodimer, acts to both positively and negatively influence transcription of the araB promoter. In the absence of L-arabinose, the AraC dimer binds to the $O_2$ and $I_1$ binding sites, forming a DNA loop that inhibits transcription. The $I_1$ half site overlaps with the −35 region of the wild type araB promoter.

In the presence of an effective concentration of L-arabinose, the AraC acts to stimulate transcription. Upon binding to L-arabinose, the AraC dimer releases its association with the $O_2$ binding site, forming an association with the $I_1/I_2$ half sites, that is the $I_1/I_2$ region that partially overlaps with the −35 region of the present promoter sequence. Release of the DNA loop and subsequent association of the AraC dimer with the $I_1/I_2$ region stimulates transcription.

The sensitivity of the araB operon is also influenced by the level of cyclic AMP in the cell, which in turn influences the level of cAMP receptor protein (CRP, also referred to as "CAP"). A cyclic AMP receptor protein binding site (CRP binding site) is upstream of, and partially overlaps with, the $I_1/I_2$ region. In the presence of glucose, catabolic repression of the araB expression system is observed. Conversely, increased levels of cAMP promote binding of CRP to the CRP binding site. Binding of CRP to the CRP binding site in combination with L-arabinose induction is required for maximum transcription activity.

The araB promoter region described herein generally spans a portion of the araB expression system that encompasses a region starting immediately upstream and adjacent to the start codon of the coding region targeted for expression through the −35 region (encoding a portion of the $I_1/I_2$ half sites). One of skill in the art can operably link the present mutant araB promoter sequence (SEQ ID NO: 2) to a nucleic acid molecule comprising the upstream AraC transcription factor binding sites, e.g., $O_2$ as well as other regulatory elements associated with L-arabinose induction. The upstream region encompassing the AraC transcription factor binding site(s) may include at least one $O_2$ site (SEQ ID NO: 29), at least one $O_1$ site (SEQ ID NO: 30), at least one CRP binding site (SEQ ID NO: 31), and the remaining portion of the $I_1/I_2$ region not included in the 5' end of the araB promoter sequence (SEQ ID NO: 2), where each of the elements are appropriately spaced to facilitate effective AraC regulated L-arabinose induction. Preferably, the upstream AraC transcription factor binding region comprises SEQ ID NO: 33.

The mutant araB promoter region may have the consensus sequence provided by SEQ ID NO: 2. The mutant araB promoter region may comprise a nucleic acid molecule having a sequence selected from the group consisting of SEQ ID NOs: 17, 22, 23, 24, and 25.

The mutant araB promoter region described herein may be operably linked to an upstream (5' to the present mutant araB promoter sequence; SEQ ID NO: 2) AraC transcription factor binding region. Or, in an L-arabinose inducible expression system, the araB promoter system, may comprise an AraC transcription factor binding region operably linked to the present araB promoter sequence. Preferably, the araB promoter system comprises the AraC transcription factor binding region of SEQ ID NO: 33 operably linked to SEQ ID NO: 2. The araB promoter system comprising the present araB promoter is provided by SEQ ID NO: 34. In addition, the present araB promoter system may comprise a nucleic acid molecule having a nucleic acid sequence selected from the group consisting of SEQ ID NOs: 34, 35, 36, 37, 38, and 39.

The present araB promoter can be used to construct chimeric genes, expression cassettes, and expression vectors as well as host cells comprising such constructs. For example, a chimeric expression cassette may be provided comprising i) a nucleic acid molecule encoding an L-arabinose inducible expression system, said L-arabinose inducible expression system comprising an AraC transcription factor binding region operably linked to the an araB promoter having a nucleic acid sequence of SEQ ID NO: 2;

ii) a coding region of interest operably linked to the nucleic acid molecule of (i).

In addition, a vector comprising the chimeric expression cassette may be provided. In such a vector, it is preferred that an expressible copy of the araC gene be included.

Microbial host cells comprising the present vectors are also provided. Examples of host strains include, but are not limited to bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. The preferred host cells may be bacterial host cells, such as an *Enterobacteriaceae* or selected from the genera consisting of *Escherichia, Salmonella*, and *Bacillus*. Preferably, the host strain is *Escherichia coli*.

The microbial cell comprising the present araB promoter expression system requires an effective amount of intracellular AraC protein to act as a transcriptional regulator. A microbial host cell comprising an effective amount of AraC will be referred to an "AraC+" microbial host cell. The AraC protein can be provided by an expressible copy of araC anywhere within the transformed microbial host cell. Preferably, the transformed microbial host cell comprises an expressible copy of the araC gene on a vector and more preferably, the expressible copy of the araC gene in located on the same vector as the present araB promoter expression system. The present vector preferably comprises an araC gene comprising an $O_1$ region (SEQ ID NO: 30; a binding site for AraC that represses transcription of the araC promoter (Pc) (Schleif, R., supra). In addition, the araC gene may be located on the same expression vector and transcribed in opposite orientation relative to the araB promoter expression system (FIG. 1).

Expressible Peptides of Interest

As used herein, the terms "expressible peptides of interest", "expressible protein of interest", and "target gene product" refer to the desired peptide/protein product encoded by the coding region of interest. The target gene product may optionally include a small N-terminal addition (e.g. 22 amino acids) encoded by a promoter region providing an additional start codon so long as the activity/function of the gene product is not adversely affected. Alternatively, the target gene product need not include a small N-terminal addition, that is, the promoter region does not include a start codon 5'). The target gene product may include any peptide/protein product including, but not limited to peptides, polypeptides, proteins, fusion peptides/proteins, and enzymes. The target gene product may be a fusion peptide comprising at least one inclusion body tag and at least one target surface-binding peptide.

Body Surface-Binding Peptides

The target surface-binding peptide may be a body surface-binding peptide (See Table A). As defined herein, body surface-binding peptides refer to peptide sequences that specifically bind with high affinity to a specific body surface including, but not limited to hair, nails, skin, and the tissues of the oral cavity (gums, teeth, etc.), for example, the body surface-binding peptides may be selected from the group consisting of hair-binding peptides, skin-binding peptides, nail-binding peptides, and teeth-binding peptides.

Phage display has been used to identify various body surface-binding peptides. For example, peptides having an affinity for a body surface have been described in (U.S. Pat. Nos. 7,220,405 and 7,285,264; U.S. Pat. App. Pub. Nos. 2005/0226839, 2005/0249682, 2007/0065387, 2007/0067924, 2007/0196305, 2007/0110686, 2006/0073111, and 2006/0199206; U.S. patent application Ser. No.11/877,692; U.S. patent applicaiton Pub. Ser. No. 11/939583; and Int'l Pat. App. Pub. No. WO2004048399)

Examples of various body surface-binding peptides are provided in Table A.

TABLE A

Examples of Body Surface-Binding Peptides

| Body Surface | Amino Acid Sequence | SEQ ID NO: | Reference |
|---|---|---|---|
| Hair | RVPNKTVTVDGA | 46 | US 2005/0226839<br>US 7,220,405 |
| Hair | DRHKSKYSSTKS | 47 | US 2005/0226839<br>US 7,220,405 |
| Hair | KNFPQQKEFPLS | 48 | US 2005/0226839<br>US 7,220,405 |
| Hair | QRNSPPAMSRRD | 49 | US 2005/0226839<br>US 7,220,405 |
| Hair | TRKPNMPHGQYL | 50 | US 2005/0226839<br>US 7,220,405 |
| Hair | KPPHLAKLPFTT | 51 | US 2005/0226839<br>US 7,220,405 |
| Hair | NKRPPTSHRIHA | 52 | US 2005/0226839<br>US 7,220,405 |
| Hair | NLPRYQPPCKPL | 53 | US 2005/0226839<br>US 7,220,405 |
| Hair | RPPWKKPIPPSE | 54 | US 2005/0226839<br>US 7,220,405 |
| Hair | RQRPKDHFFSRP | 55 | US 2005/0226839<br>US 7,220,405 |
| Hair | SVPNKXVTVDGX | 56 | US 2005/0226839<br>US 7,220,405 |
| Hair | TTKWRHRAPVSP | 57 | US 2005/0226839<br>US 7,220,405 |
| Hair | WLGKNRIKPRAS | 58 | US 2005/0226839<br>US 7,220,405 |
| Hair | SNFKTPLPLTQS | 59 | US 2005/0226839<br>US 7,220,405 |
| Hair | SVSVGMKPSPRP | 60 | US 2005/0226839<br>US 7,220,405 |
| Hair | DLHTVYH | 61 | US 2005/0226839<br>US 7,220,405 |
| Hair | HIKPPTR | 62 | US 2005/0226839<br>US 7,220,405 |
| Hair | HPVWPAI | 63 | US 2005/0226839<br>US 7,220,405 |
| Hair | MPLYYLQ | 64 | US 2005/0226839<br>US 7,220,405 |
| Hair | HLTVPWRGGGSAVPFYSHSQI<br>TLPNH | 65 | US 2005/0226839<br>US 7,220,405 |

TABLE A-continued

Examples of Body Surface-Binding Peptides

| Body Surface | Amino Acid Sequence | SEQ ID NO: | Reference |
|---|---|---|---|
| Hair | GPHDTSSGGVRPNLHHTSKKE KRENRKVPFYSHSVTSRGNV | 66 | US 2005/0226839 US 7,220,405 |
| Hair | KHPTYRQ | 67 | US 2005/0226839 US 7,220,405 |
| Hair | HPMSAPR | 68 | US 2005/0226839 US 7,220,405 |
| Hair | MPKYYLQ | 69 | US 2005/0226839 US 7,220,405 |
| Hair | MHAHSIA | 70 | US 2005/0226839 US 7,220,405 |
| Hair | AKPISQHLQRGS | 71 | US 2005/0226839 US 7,220,405 |
| Hair | APPTPAAASATT | 72 | US 2005/0226839 US 7,220,405 |
| Hair | DPTEGARRTIMT | 73 | US 2005/0226839 US 7,220,405 |
| Hair | LDTSFPPVPFHA | 74 | US 2005/0226839 US 7,220,405 |
| Hair | LDTSFHQVPFHQ | 75 | US 2005/0226839 US 7,220,405 |
| Hair | LPRIANTWSPS | 76 | US 2005/0226839 US 7,220,405 |
| Hair | RTNAADHPAAVT | 77 | US 2005/0226839 US 7,220,405 US 2007/0065387 |
| Hair | SLNWVTIPGPKI | 78 | US 2005/0226839 US 7,220,405 |
| Hair | TDMQAPTKSYSN | 79 | US 2005/0226839 US 7,220,405 |
| Hair | TIMTKSPSLSCG | 80 | US 2005/0226839 US 7,220,405 |
| Hair | TPALDGLRQPLR | 81 | US 2005/0226839 US 7,220,405 |
| Hair | TYPASRLPLLAP | 82 | US 2005/0226839 U5 7,220,405 |
| Hair | AKTHKHPAPSYS | 83 | US 2005/0226839 U5 7,220,405 |
| Hair | TDPTPFSISPER | 84 | US 2005/0226839 US 7,220,405 |
| Hair | SQNWQDSTSYSN | 85 | US 2005/0226839 US 7,220,405 |
| Hair | WHDKPQNSSKST | 86 | US 2005/0226839 US 7,220,405 |
| Hair | LDVESYKGTSMP | 87 | US 2005/0226839 US 7,220,405 |
| Hair | NTPKENW | 88 | WO2004048399 |
| Hair | NTPASNR | 89 | WO2004048399 |
| Hair | PRGMLST | 90 | WO2004048399 |
| Hair | PPTYLST | 91 | WO2004048399 |

TABLE A-continued

Examples of Body Surface-Binding Peptides

| Body Surface | Amino Acid Sequence | SEQ ID NO: | Reference |
|---|---|---|---|
| Hair | TIPTHRQHDYRS | 92 | WO2004048399 |
| Hair | TPPTHRL | 93 | WO2004048399 |
| Hair | LPTMSTP | 94 | WO2004048399 |
| Hair | LGTNSTP | 95 | WO2004048399 |
| Hair | TPLTGSTNLLSS | 96 | WO2004048399 |
| Hair | TPLTKET | 97 | WO2004048399 |
| Hair | KQSHNPP | 98 | WO2004048399 |
| Hair | QQSHNPP | 99 | WO2004048399 |
| Hair | TQPHNPP | 100 | WO2004048399 |
| Hair | STNLLRTSTVHP | 101 | WO2004048399 |
| Hair | HTQPSYSSTNLF | 102 | WO2004048399 |
| Hair | SLLSSHA | 103 | WO2004048399 |
| Hair | QQSSISLSSHAV | 104 | WO2004048399 |
| Hair | NASPSSL | 105 | WO2004048399 |
| Hair | HSPSSLR | 106 | WO2004048399 |
| Hair | K H/R/N SHHTH | 107 | WO2004048399 |
| Hair | E H/R/N SHHTH | 108 | WO2004048399 |
| Hair | SHHTHYGQPGPV | 109 | WO2004048399 |
| Hair | LESTSLL | 110 | WO2004048399 |
| Hair | DLTLPFH | 111 | US 2007/0065387 |
| Hair | RTNAADHP | 112 | US 2007/0067924 |
| Hair | IPWWNIRAPLNA | 113 | US 2007/0067924 |
| Hair | EQISGSLVAAPWEGEGER | 114 | US 11/877,692 |
| Hair | PKRGRHKRPKRHKGGGTPPELLHGAPRSC | 115 | US 11/877,692 |
| Hair | LDTSFHQVPFHQKRKRKD | 116 | US 11/877,692 |
| Hair | EQISGSLVAAPWKRKRKD | 117 | US 11/877,692 |
| Hair | TPPELLHGDPRSKRKRKD | 118 | US 11/877,692 |
| Hair | NTSQLSTEGEGED | 119 | US 11/877,692 |
| Hair | TPPELLHGDPRSC | 120 | US 2007/0067924 |
| Hair | HINKTNPHQGNHHSEKTQRQ | 121 | US 11/939583 |
| Hair | HAHKNQKETHQRHAA | 122 | US 11/939583 |
| Hair | HEHKNQKETHQRHAA | 123 | US 11/939583; US 7,285,264 |
| Hair | HNHMQERYTEPQHSPSVNGL | 124 | US 11/939583 |
| Hair | THSTHNHGSPRHTNADA | 125 | US 2007/0196305 |
| Hair | GSCVDTHKADSCVANNGPAT | 126 | US 11/939583 |
| Hair | AQSQLPDKHSGLHERAPQRY | 127 | US 11/939583 |
| Hair | AQSQLPAKHSGLHERAPQRY | 128 | US 11/939583 |

TABLE A-continued

Examples of Body Surface-Binding Peptides

| Body Surface | Amino Acid Sequence | SEQ ID NO: | Reference |
|---|---|---|---|
| Hair | AQSQLPEKHSGLHERAPQRY | 129 | US 11/939583 |
| Hair | TDMMHNHSDNSPPHRRSPRN | 130 | US 11/939583 |
| Hair | TPPELAHTPHHLAQTRLTDR | 131 | US 11/939583 |
| Hair | RLLRLLRLLRLL | 132 | US 11/939583 |
| Hair | TPPELLHGEPRS | 133 | US 11/939583 |
| Hair | TPPELLHGAPRS | 134 | US 7,285,264 |
| Hair (normal and bleached) | EQISGSLVAAPW | 135 | US 2005/0226839 US 7,220,405 |
| Hair (bleached) | NEVPARNAPWLV | 136 | US 2005/0226839 US 7,220,405 |
| Hair (bleached) | NSPGYQADSVAIG | 137 | US 2005/0226839 US 7,220,405 |
| Hair (bleached) | AKPISQHLQRGS | 138 | US 2005-0226839 US 7,220,405 |
| Hair (bleached) | LDTSFPPVPFHA | 139 | US 2005/0226839 US 7,220,405 |
| Hair (bleached) | SLNWVTIPGPKI | 140 | US 2005/0226839 US 7,220,405 |
| Hair (bleached) | TQDSAQKSPSPL | 141 | US 2005/0226839 US 7,220,405 |
| Hair (bleached) | KELQTRNVVQRE | 142 | US 2005/0226839 US 7,220,405 |
| Hair (bleached) | QRNSPPAMSRRD | 143 | US 2005/0226839 US 7,220,405 |
| Hair (bleached) | TPTANQFTQSVP | 144 | US 2005/0226839 US 7,220,405 |
| Hair (bleached) | AAGLSQKHERNR | 145 | US 2005/0226839 US 7,220,405 |
| Hair (bleached) | ETVHQTPLSDRP | 146 | US 2005/0226839 US 7,220,405 |
| Hair (bleached) | KNFPQQKEFPLS | 147 | US 2005/0226839 US 7,220,405 |
| Hair (bleached) | LPALHIQRHPRM | 148 | US 2005/0226839 US 7,220,405 |
| Hair (bleached) | QPSHSQSHNLRS | 149 | US 2005/0226839 US 7,220,405 |
| Hair (bleached) | RGSQKSKPPRPP | 150 | US 2005/0226839 US 7,220,405 |
| Hair (bleached) | THTQKTPLLYYH | 151 | US 2005/0226839 US 7,220,405 |
| Hair (bleached) | TKGSSQAILKST | 152 | US 2005/0226839 US 7,220,405 |
| Hair (normal and bleached) | TAATTSP | 153 | US 2005/0226839 US 7,220,405 |

TABLE A-continued

Examples of Body Surface-Binding Peptides

| Body Surface | Amino Acid Sequence | SEQ ID NO: | Reference |
|---|---|---|---|
| Hair (bleached) | LGIPQNL | 154 | US 2005/0226839 US 7,220,405 |
| Hair (Conditioner resistant) | THSTHNHGSPRHTNADAGNP | 155 | US 2007/0065387 US 2007/0196305 |
| Hair (Conditioner resistant) | QQHKVHHQNPDRSTQDAHHS | 156 | US 2007/0196305 |
| Hair (Conditioner resistant) | HHGTHHNATKQKNHV | 157 | US 2007/0196305 |
| Hair (Conditioner resistant) | STLHKYKSQDPTPHH | 158 | US 2007/0196305 |
| Hair (Conditioner resistant) | SVSVGMKPSPRP | 159 | US 2007/0196305 |
| Hair (shampoo resistant) | TPPTNVLMLATK | 160 | US 2006/0073111 |
| Hair (shampoo resistant) | TPPELLHGDPRS | 161 | US 2006/0073111 |
| Hair (shampoo resistant) | NTSQLST | 162 | US 2007/0067924 US 7,285,264 |
| Hair (conditioner resistant) | STLHKYKSQDPTPHH | 163 | US 2007/0196305 |
| Hair (shampoo and conditioner resistant) | GMPAMHWIHPFA | 164 | US 2006/0073111 US 7,285,264 |
| Hair (shampoo and conditioner resistant) | HDHKNQKETHQRHAA | 165 | US 2006/0073111 US 7,285,264 |
| Hair (shampoo and conditioner resistant) | HNHMQERYTDPQHSPSVNGL | 166 | US 2006/0073111 US 7,285,264 |
| Hair (shampoo and conditioner resistant) | TAEIQSSKNPNPHPQRSWTN | 167 | US 2006/0073111 US 7,285,264 |
| Hair (multiple binding domains) | P-NTSQLST (hair-binding peptide)-GGG (spacer)-RTNAADHPKC (hair-binding peptide)-GGG (spacer)-NTSQLST (hair-binding peptide)-GGG (spacer)-RTNAADHPKC (hair-binding | 168 | US 11/939583 |

TABLE A-continued

Examples of Body Surface-Binding Peptides

| Body Surface | Amino Acid Sequence | SEQ ID NO: | Reference |
|---|---|---|---|
| | peptide)-GGG (spacer)-NTSQLST (hair-binding peptide)-GGG (spacer)-RTNAADHPKC (hair-binding peptide) | | |
| Hair (multiple binding domains) | P-RTNAADHPAAVT (hair-binding peptide)-GGGCGGG (spacer)-RTNAADHPAAVT (hair-binding peptide)-GGGCGGG (spacer)-RTNAADHPAAVT (hair-binding peptide)-GGGC (spacer) | 169 | US 11/939583 |
| Hair (multiple binding domains) | P-RTNAADHPAAVT (hair-binding peptide)-GGGCGGG (spacer)-IPWWNIRAPLNA (hair-binding peptide)-GGGCGGG (spacer)-DLTLPFH (hair-binding peptide)-GGGC (spacer) | 170 | US 11/939583 |
| Hair (multiple binding domains) | P-RTNAADHP (hair-binding peptide)-GGG (spacer)-TPPELLHGDPRSKC (hair-binding peptide)-GGG (spacer)-RTNAADHP (hair-binding peptide)-GGG (spacer)-TPPELLHGDPRSKC (hair-binding peptide)-GGG (spacer)-RTNAADHP (hair-binding peptide)-GGG (spacer)-TPPELLHGDPRSKC (hair-binding peptide) | 171 | US 11/939583 |
| Hair (multiple binding domains) | P-TPPTNVLMLATK (hair-binding peptide)-GGG (spacer)-RTNAADHPKC (hair-binding peptide)-GGG (spacer)-TPPTNVLMLATK (hair-binding peptide)-GGG (spacer)-RTNAADHPKC (hair-binding peptide)-GGG (spacer)-TPPTNVLMLATK (hair-binding peptide)-GGG (spacer)-RTNAADHPKC (hair-binding peptide) | 172 | US 11/939583 |
| Hair (multiple binding domains) | P-RTNAADHP (hair-binding peptide)-GGG (spacer) TPPTNVLMLATKKC (hair-binding peptide)-GGG (spacer)-RTNAADHP (hair-binding peptide)-GGG (spacer)-TPPTNVLMLATKKC (hair-binding peptide) GGG (spacer)-RTNAADHP (hair-binding peptide)-GGG (spacer)-TPPTNVLMLATKKC (hair-binding peptide) | 173 | US 11/939583 |
| Hair (multiple binding domains) | PG (Spacer)-IPWWNIRAPLNA (hair-binding peptide)- GAG (spacer)-IPWWNIRAPLNA (hair-binding peptide)-GGSGPGSGG (spacer)-NTSQLST (hair-binding peptide)-GGG (spacer)-NTSQLST (hair-binding peptide)-GGPKK (spacer) | 174 | US 11/939583 |
| Hair and skin (Empirical) | KRGRHKRPKRHK | 175 | US 2007/0065387 US 2007/0110686 US 2007/0067924 |

TABLE A-continued

Examples of Body Surface-Binding Peptides

| Body Surface | Amino Acid Sequence | SEQ ID NO: | Reference |
|---|---|---|---|
| Hair and skin (Empirical) | RLLRLLR | 176 | US 2007/0065387 US 2007/0110686 |
| Hair and skin (Empirical) | HKPRGGRKKALH | 177 | US 2007/0065387 US 2007/0110686 |
| Hair and skin (Empirical) | KPRPPHGKKHRPKHRPKK | 178 | US 2007/0065387 US 2007/0110686 |
| Hair and skin (Empirical) | RGRPKKGHGKRPGHRARK | 179 | US 2007/0065387 US 2007/0110686 |
| Skin | TPFHSPENAPGS | 180 | US 11/877,692 US 2005/0249682 |
| Skin | TPFHSPENAPGSK | 181 | US 2007/0110686 |
| Skin | TPFHSPENAPGSGGGS | 182 | US 2007/0110686 |
| Skin | TPFHSPENAPGSGGGSS | 182 | US 2007/0110686 |
| Skin | TPFHSPENAPGSGGG | 184 | US 2007/0110686 |
| Skin | FTQSLPR | 185 | US 11/877,692 US 2005/0249682 |
| Skin | KQATFPPNPTAY | 186 | US 11/877,692 US 2005/0249682 WO2004048399 |
| Skin | HGHMVSTSQLSI | 187 | US 11/877,692 US 2005/0249682 WO2004048399 |
| Skin | LSPSRMK | 188 | US 11/877,692 US 2005/0249682 WO2004048399 |
| Skin | LPIPRMK | 189 | US 2005/0249682 WO2004048399 |
| Skin | HQRPYLT | 190 | US 2005/0249682 WO2004048399 |
| Skin | FPPLLRL | 191 | US 2005/0249682 WO2004048399 |
| SKIN | QATFMYN | 192 | WO2004048399 |
| SKIN | VLTSQLPNHSM | 193 | WO2004048399 |
| Skin | HSTAYLT | 194 | WO2004048399 |
| Skin | APQQRPMKTFNT | 195 | WO2004048399 |
| Skin | APQQRPMKTVQY | 196 | WO2004048399 |
| Skin | PPWLDLL | 197 | WO2004048399 |
| Skin | PPWTFPL | 198 | WO2004048399 |
| Skin | SVTHLTS | 199 | WO2004048399 |
| Skin | VITRLTS | 200 | WO2004048399 |
| Skin | DLKPPLLALSKV | 201 | WO2004048399 |
| Skin | SHPSGALQEGTF | 202 | WO2004048399 |
| Skin | FPLTSKPSGACT | 203 | WO2004048399 |

TABLE A-continued

Examples of Body Surface-Binding Peptides

| Body Surface | Amino Acid Sequence | SEQ ID NO: | Reference |
|---|---|---|---|
| Skin | DLKPPLLALSKV | 204 | WO2004048399 |
| Skin | PLLALHS | 205 | WO2004048399 |
| Skin | VPISTQI | 206 | WO2004048399 |
| Skin | YAKQHYPISTFK | 207 | WO2004048399 |
| Skin | HSTAYLT | 208 | WO2004048399 |
| Skin | STAYLVAMSAAP | 209 | WO2004048399 |
| Skin (Body Wash Resistant) | SVSVGMKPSPRP | 210 | US 11/877,692 US 2006/0199206 |
| Skin (Body Wash Resistant) | TMGFTAPRFPHY | 211 | US 11/877,692 US 2006/0199206 |
| Skin (Body Wash Resistant) | NLQHSVGTSPVW | 212 | US 11/877,692 US 2006/0199206 |
| Skin (Body Wash Resistant) | QLSYHAYPQANHHAP | 213 | US 11/877,692 US 2006/0199206 |
| Skin (Body Wash Resistant) | NQAASITKRVPY | 214 | US 2006/0199206 |
| Skin (Body Wash Resistant) | SGCHLVYDNGFCDH | 215 | US 11/877,692 US 2006/0199206 |
| Skin (Body Wash Resistant) | ASCPSASHADPCAH | 216 | US 11/877,692 US 2006/0199206 |
| Skin (Body Wash Resistant) | NLCDSARDSPRCKV | 217 | US 11/877,692 US 2006/0199206 |
| Skin (Body Wash Resistant) | NHSNWKTAADFL | 218 | US 11/877,692 US 2006/0199206 |
| Skin (Body Wash Resistant) | GSSTVGRPLSYE | 219 | US 2006/0199206 |
| Skin (Body Wash Resistant) | SDTISRLHVSMT | 220 | US 11/877,692 US 2006/0199206 |
| Skin (Body Wash Resistant) | SPLTVPYERKLL | 221 | US 2006/0199206 |

TABLE A-continued

Examples of Body Surface-Binding Peptides

| Body Surface | Amino Acid Sequence | SEQ ID NO: | Reference |
|---|---|---|---|
| Skin (Body Wash Resistant) | SPYPSWSTPAGR | 222 | US 11/877,692 US 2006/0199206 |
| Skin (Body Wash Resistant) | VQPITNTRYEGG | 223 | US 2006/0199206 |
| Skin (Body Wash Resistant) | WPMHPEKGSRWS | 224 | US 2006/0199206 |
| Skin (Body Wash Resistant) | DACSGNGHPNNCDR | 225 | US 11/877,692 US 2006/0199206 |
| Skin (Body Wash Resistant) | DHCLGRQLQPVCYP | 226 | US 2006/0199206 |
| Skin (Body Wash Resistant) | DWCDTIIPGRTCHG | 227 | US 11/877,692 US 2006/0199206 |
| Fingernail | ALPRIANTWSPS | 228 | US 2005/0226839 US 7,220,405 |
| Fingernail and Hair | YPSFSPTYRPAF | 229 | US 2005/0226839 US 7,220,405 |
| Tooth (pellicle) | AHPESLGIKYALDGNSDPHA | 230 | US 11/877,692 |
| Tooth (pellicle) | ASVSNYPPIHHLATSNTTVN | 231 | US 11/877,692 |
| Tooth (pellicle) | DECMEPLNAAHCWR | 232 | US 11/877,692 |
| Tooth (pellicle) | DECMHGSDVEFCTS | 233 | US 11/877,692 |
| Tooth (pellicle) | DLCSMQMMNTGCHY | 234 | US 11/877,692 |
| Tooth (pellicle) | DLCSSPSTWGSCIR | 235 | US 11/877,692 |
| Tooth (pellicle) | DPNESNYENATTVSQPTRHL | 236 | US 11/877,692 |
| Tooth (pellicle) | EPTHPTMRAQMHQSLRSSSP | 237 | US 11/877,692 |
| Tooth (pellicle) | GNTDTTPPNAVMEPTVQHKW | 238 | US 11/877,692 |
| Tooth (pellicle) | NGPDMVQSVGKHKNS | 239 | US 11/877,692 |
| Tooth (pellicle) | NGPEVRQIPANFEKL | 240 | US 11/877,692 |
| Tooth (pellicle) | NNTSADNPPETDSKHHLSMS | 241 | US 11/877,692 |
| Tooth (pellicle) | NNTWPEGAGHTMPSTNIRQA | 242 | US 11/877,692 |

TABLE A-continued

Examples of Body Surface-Binding Peptides

| Body Surface | Amino Acid Sequence | SEQ ID NO: | Reference |
|---|---|---|---|
| Tooth (pellicle) | NPTATPHMKDPMHSNAHSSA | 243 | US 11/877,692 |
| Tooth (pellicle) | NPTDHIPANSTNSRVSKGNT | 244 | US 11/877,692 |
| Tooth (pellicle) | NPTDSTHMMHARNHE | 245 | US 11/877,692 |
| Tooth (pellicle) | QHCITERLHPPCTK | 246 | US 11/877,692 |
| Tooth (pellicle) | TPCAPASFNPHCSR | 247 | US 11/877,692 |
| Tooth (pellicle) | TPCATYPHFSGCRA | 248 | US 11/877,692 |
| Tooth (pellicle) | WCTDFCTRSTPTSTSRSTTS | 249 | US 11/877,692 |
| Tooth (enamel) | APPLKTYMQERELTMSQNKD | 250 | US 11/877,692 |
| Tooth (enamel) | EPPTRTRVNNHTVTVQAQQH | 251 | US 11/877,692 |
| Tooth (enamel) | GYCLRGDEPAVCSG | 252 | US 11/877,692 |
| Tooth (enamel) | LSSKDFGVTNTDQRTYDYTT | 253 | US 11/877,692 |
| Tooth (enamel) | NFCETQLDLSVCTV | 254 | US 11/877,692 |
| Tooth (enamel) | NTCQPTKNATPCSA | 255 | US 11/877,692 |
| Tooth (enamel) | PSEPERRDRNIAANAGRFNT | 256 | US 11/877,692 |
| Tooth (enamel) | THNMSHFPPSGHPKRTAT | 257 | US 11/877,692 |
| Tooth (enamel) | TTCPTMGTYHVCWL | 258 | US 11/877,692 |
| Tooth (enamel) | YCADHTPDPANPNKICGYSH | 259 | US 11/877,692 |
| Tooth (enamel) | AANPHTEWDRDAFQLAMPPK | 260 | US 11/877,692 |
| Tooth (enamel) | DLHPMDPSNKRPDNPSDLHT | 261 | US 11/877,692 |
| Tooth (enamel) | ESCVSNALMNQCIY | 262 | US 11/877,692 |
| Tooth (enamel) | HNKADSWDPDLPPHAGMSLG | 263 | US 11/877,692 |
| Tooth (enamel) | LNDQRKPGPPTMPTHSPAVG | 264 | US 11/877,692 |
| Tooth (enamel) | NTCATSPNSYTCSN | 265 | US 11/877,692 |
| Tooth (enamel) | SDCTAGLVPPLCAT | 266 | US 11/877,692 |
| Tooth (enamel) | TIESSQHSRTHQQNYGSTKT | 267 | US 11/877,692 |

TABLE A-continued

Examples of Body Surface-Binding Peptides

| Body Surface | Amino Acid Sequence | SEQ ID NO: | Reference |
|---|---|---|---|
| Tooth (enamel) | VGTMKQHPTTTQPPRVSATN | 268 | US 11/877,692 |
| Tooth (enamel) | YSETPNDQKPNPHYKVSGTK | 269 | US 11/877,692 |

The body surface-binding peptide may be selected from the group consisting of hair-binding peptides, skin-binding peptides, nail-binding peptides, and teeth-binding peptides. The body surface-binding peptide may be selected from the group consisting of hair-binding peptides (SEQ ID NOs: 46-179 and 229), skin-binding peptides (SEQ ID NOs. 175-227), nail-binding peptides (SEQ ID NOs. 228-229), and teeth-binding peptides (SEQ ID NOs. 230-269).

Production of Fusion Peptides Comprising at Least One Inclusion Body Tag

The present araB expression system can be operably linked to any coding region of interest. The resulting chimeric gene is transformed and expressed in an appropriate microbial host cell, typically in the form of an expression vector. Induction with an effective amount of L-arabinose is used to produce the desired gene product.

The desired gene product is a small bioactive peptide of interest that is appreciably soluble in the host cell and/or host cell liquid lysate under normal physiological conditions. The peptides of interest are preferably, generally short (<50 amino acids in length) and difficult to produce in sufficient amounts due to proteolytic degradation. Fusion of the peptide of interest to at least one inclusion body forming tags creates a fusion peptide that is insoluble in the host cell and/or host cell lysate under normal physiological conditions. Production of the peptide of interest is typically increased when expressed and accumulated in the form of an insoluble inclusion body as the peptide is generally more protected from proteolytic degradation. Furthermore, the insoluble fusion protein can be easily separated from the host cell lysate using centrifugation or filtration.

The length of the peptide of interest may vary as long as (1) the peptide is appreciably soluble in the host cell and/or cell lysate, and/or (2) the amount of the targeted peptide produced is significantly increased when expressed in the form of an insoluble fusion peptide/inclusion body; that is, expression in the form of a fusion protein protect the peptide of interest from proteolytic degradation. Typically the peptide of interest is less than 200 amino acids in length, preferably less than 100 amino acids in length, more preferably less than 75 amino acids in length, even more preferably less than 50 amino acids in length, and most preferably less than 25 amino acids in length.

The function of the peptide of interest is not limited by the present method and may include, but is not limited to, bioactive molecules that act as curative agents for diseases, such as insulin, interferon, interleukins, peptide hormones, anti-angiogenic peptides, and peptides that bind to and affect defined cellular targets such as receptors, channels, lipids, cytosolic proteins, and membrane proteins (see U.S. Pat. No. 6,696, 089); peptides having an affinity for a particular material, such as biological tissues, biological molecules, hair-binding peptides (see U.S. patent application Ser. No. 11/074473; Int'l Pat. App. No. WO 0179479; U.S. Pat. App. Pub. Nos. 2002/0098524; 2003/0152976; Int'l Pat. App. No. WO 04048399; U.S. Pat. App. Pub. No 2007/0067924; and 2007/0249805), skin-binding peptides (see U.S. Pat. No. 7,309, 482; Int'l. Pat. App. No. WO 2004/000257; and U.S. Pat. App. Pub. No. 2007/0249805), nail-binding peptides (see U.S. Pat. App. Pub. No. 2007/0249805), cellulose-binding peptides, polymer-binding peptides (see U.S. Pat. App. Pub. Nos. 2007/0141629, 2007/0264720, 2008/0207872, 2007/0141628, and 2007/0261775), clay-binding peptides, silica-binding peptides, and carbon nanotube binding peptides) for targeted delivery of at least one benefit agent (see U.S. patent application Ser. Nos. 10/935642; 11/074473; and U.S. Pat. App. Pub. No. 2007/0249805).

The peptide of interest may comprise at least one body surface-binding peptide selected from the group of hair-binding peptides, skin-binding peptides, nail-binding peptides, antimicrobial peptides, and polymer-binding peptides. The peptide of interest may be selected from the group consisting of a hair-binding peptide comprising an amino acid sequence selected from the group consisting of SEQ ID NOs 46 to 179 (SEQ ID NOs: 168-174 are examples of hair binding-domains comprising multiple hair-binding peptides coupled together by short spacers), a skin-binding peptide comprising an amino acid sequence selected from the group consisting of SEQ ID NOs: 175 to 227, a nail-binding peptide comprising an amino acid sequence selected from the group consisting of SEQ ID NOs: 228 and 229, and a teeth-binding peptide comprising an amino acid sequence selected from the group consisting of SEQ ID NOs. 230 to 269.

Typically, the fusion peptide should be insoluble in an aqueous matrix at a temperature of 10° C. to 50° C., preferably 10° C. to 40° C. The aqueous matrix typically comprises a pH range of 5 to 12, preferably 6 to 10, and most preferably 6 to 8. The temperature, pH, and/or ionic strength of the aqueous matrix can be adjusted to obtain the desired solubility characteristics of the fusion peptide/inclusion body.

As used herein, the term "benefit agent" refers to a molecule that imparts a desired functionality to a target material, such as hair, skin, etc., (see U.S. patent application Ser. Nos. 10/935642; 11/074473; and U.S. patent application Ser. No. 11/696380 for a list of typical benefit agents such as conditioners, pigments/colorants, fragrances, etc.). The benefit agent may be a peptide of interest itself or may be one or more molecules bound to, (covalently or non-covalently, or associated with, the peptide of interest wherein the binding affinity of the peptide of interest is used to selectively target the benefit agent to the targeted material. The peptide of interest may comprise at least one region having an affinity for at least one target material, e.g., biological molecules, polymers, hair, skin, nail, other peptides, etc., and at least one region having an affinity for the benefit agent, e.g., pharmaceutical agents, antimicrobial agents, pigments, conditioners, dyes, fragrances, etc. The peptide of interest may comprise a plurality of regions having an affinity for the target material and a plurality of regions having an affinity for one or more benefit agents. Moreover, the peptide of interest may comprise at least one region having an affinity for a targeted material and a plurality of regions having an affinity for a variety of benefit agents wherein the benefit agents may be the same or different. Examples of benefits agents include, but are not limited to, conditioners for personal care products, pigments, dye, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides).

Cleavable Peptide Linkers

The use of cleavable peptide linkers is well known in the art. Fusion peptides comprising at least one inclusion body tag will typically include at least one cleavable sequence separating the inclusion body tag from the peptide of interest. The cleavable sequence facilitates separation of the inclusion body tag(s) from the peptide(s) of interest. The cleavable sequence may be provided by a portion of the inclusion body tag and/or the peptide of interest (e.g., inclusion of an acid cleavable aspartic acid—proline moiety). The cleavable sequence preferably includes in the fusion peptide at least one cleavable peptide linker between the inclusion body tag and the peptide of interest.

Means to cleave the peptide linkers are well known in the art and may include chemical hydrolysis, enzymatic cleavage agents, and combinations thereof. One or more chemically cleavable peptide linkers are included in the fusion construct to facilitate recovery of the peptide of interest from the inclusion body fusion protein. Examples of chemical cleavage reagents include cyanogen bromide, which cleaves methionine residues; N-chloro succinimide, iodobenzoic acid or BNPS-skatole [2-(2-nitrophenylsulfenyl)-3-methylindole], which cleaves tryptophan residues; dilute acids, which cleave at aspartyl-prolyl bonds, and hydroxylamine, which cleaves at asparagine-glycine bonds at pH 9.0. See Gavit, P. and Better, M., *J. Biotechnol.*, 79:127-136 (2000); Szoka et al., *DNA*, 5(1):11-20 (1986); and Walker, J. M., *The Proteomics Protocols Handbook*, 2005, Humana Press, Totowa, N.J. One or more aspartic acid—proline acid cleavable recognition sites (i.e., a cleavable peptide linker comprising one or more D-P dipeptide moieties) may preferably be included in the fusion protein construct to facilitate separation of the inclusion body tag(s) form the peptide of interest. The fusion peptide may include multiple regions encoding peptides of interest separated by one or more cleavable peptide linkers.

Moreover, one or more enzymatic cleavage sequences may be included in the fusion protein construct to facilitate recovery of the peptide of interest. Proteolytic enzymes and their respective cleavage site specificities are well known in the art. Preferably, the proteolytic enzyme is selected to specifically cleave only the peptide linker separating the inclusion body tag and the peptide of interest. Examples of enzymes useful for cleaving the peptide linker include, but are not limited to Arg-C proteinase, Asp-N endopeptidase, chymotrypsin, clostripain, enterokinase, Factor Xa, glutamyl endopeptidase, Granzyme B, Achromobacter proteinase I, pepsin, proline endopeptidase, proteinase K, Staphylococcal peptidase I, thermolysin, thrombin, trypsin, and members of the Caspase family of proteolytic enzymes (e.g. Caspases 1-10) (Walker, J. M., supra). An example of a cleavage site sequence is provided by SEQ ID NO: 270 (Caspase-3 cleavage site; Thornberry et al. *J. Biol. Chem.*, 272:17907-17911 (1997) and Tyas et al., *EMBO Reports*, 1 (3):266-270 (2000)).

Typically, the cleavage step occurs after the insoluble inclusion bodies and/or insoluble fusion peptides are isolated from the cell lysate. The cells can be lysed using any number of means well known in the art, such as mechanical and/or chemical lysis. Methods to isolate the insoluble inclusion bodies/fusion peptides from the cell lysate are well known in the art, such as, centrifugation, filtration, and combinations thereof. Once recovered from the cell lysate, the insoluble inclusion bodies and/or fusion peptides can be treated with a chemical or enzymatic cleavage agent to cleave the inclusion body tag from the peptide of interest. The fusion protein and/or inclusion body may be diluted and/or dissolved in a suitable solvent prior to treatment with the cleavage agent. Alternatively, the cleavage step may be omitted if the inclusion body tag does not interfere with the activity of the peptide of interest.

After the cleavage step, preferably, the peptide of interest can be separated and/or isolated from the fusion protein and the inclusion body tags based on a differential solubility of the components. Parameters such as pH, salt concentration, and temperature may be adjusted to facilitate separation of the inclusion body tag from the peptide of interest. The peptide of interest may be soluble while the inclusion body tag and/or fusion protein is insoluble in the defined process matrix, typically aqueous. Alternatively, the peptide of interest may be insoluble while the inclusion body tag is soluble in the defined process matrix.

In an optional embodiment, the peptide of interest may be further purified using any number of well known purification techniques in the art such as ion exchange, gel purification techniques, and column chromatography (see U.S. Pat. No. 5,648,244).

Transformation and Expression

Given the mutant araB promoter system described herein and a coding region of interest, one of skill in the art can construct chimeric genes and/or expression vectors suitable for use in an appropriate expression host.

Typically, the vector or cassette contains sequences directing transcription and translation of the relevant chimeric gene, a selectable marker, and sequences allowing autonomous replication or chromosomal integration. As used herein, the present mutant araB promoter (SEQ ID NO: 2) is operably linked to a coding sequence encoding a peptide or protein of interest. The present araB promoter may be used to drive expression chromosomally or extrachromosomally, i.e. in vector based expression. The present arabinose inducible expression system comprising the mutant araB promoter is used to direct expression of a chromosomally-integrated heterologous gene. In addition, the present arabinose inducible expression system comprising the mutant araB promoter may be used to direct expression on an autonomously replicating vector, such as a plasmid). Additional 5' and 3' regulatory elements may be included to further aid in transcription initiation and/or transcriptional termination.

Termination control regions may also be derived from various genes native to the preferred hosts. Optionally, a termination site may be unnecessary but is most preferably included. The termination control region comprises the rrnB $T_1$ and $T_2$ terminators as provided by SEQ ID NO: 28.

Preferred host cells are microbial hosts that can be found broadly within the fungal or bacterial families and which grow over a wide range of temperature, pH values, and solvent tolerances. It is contemplated that any bacteria, yeast, or filamentous fungi can be suitable hosts for expression of the present nucleic acid molecules encoding the fusion peptides. Transcription, translation, and the protein biosynthetic apparatus are universal genetic processes. Because of this, large-scale microbial growth and functional gene expression may utilize a wide range of simple or complex carbohydrates, organic acids and alcohols, i.e. methanol, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules added to the culture and not typically considered nutrient or energy sources. Growth rate may also be an important regulatory factor in gene expression. Examples of host strains include, but are not limited to bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. The preferred host cells may be bacterial host cells, such as an *Enterobacteriaceae* or selected from the genera consisting of *Escherichia, Salmonella*, and *Bacillus*. Preferably, the host strain is *Escherichia coli*.

Fermentation Media

Fermentation media must contain suitable carbon substrates. Suitable substrates may include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. L-arabinose is used to induce the present arabinose inducible expression system. As such, L-arabinose is typically not included in the fermentation media until expression of the desired chimeric gene (encoding the peptide or protein of interest) is desired. L-arabinose can be added at any time during the fermentation, although it is often preferable to induce expression only after a desired cell density/mass is achieved in the fermentor. It is contemplated that the source of carbon utilized in the present invention may encompass a wide variety of carbon containing substrates and will only be limited by the choice of organism. Preferred carbon substrates include glucose, fructose, and sucrose.

In addition to a carbon source, fermentation media may or must contain other components suitable and/or necessary for the growth of the cultures and promotion of the expression of the present fusion peptides. These are known to those skilled in the art and include minerals, salts, cofactors, buffers, etc.

Culture Conditions

Suitable culture conditions can vary and depend on the chosen production host and are generally known in the art. Typically, cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where pH 6.0 to pH 8.0 is preferred.

Fermentation may be performed under either aerobic or anaerobic conditions whereas aerobic conditions are generally preferred.

Industrial Batch and Continuous Fermentations

Classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, (1992) 36:227-234.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable.

One of skill in the art will recognize that typically any amount, concentration, or other value or parameter that is given either as a range, preferred range, or a list of upper preferable values and lower preferable values, is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further illustrated by the following Examples, which indicate preferred aspects of the invention. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmol" means micromole(s), "pmol" means picomole(s), "g" means gram(s), "µg" means microgram(s), "mg" means milligram(s), "g" means the gravitation constant, "rpm" means revolutions per minute, "DTT" means dithiothreitol, "$OD_{600}$" means optical density at a 600 nm wavelength, "GFP" means green fluorescent protein; "nm" mean nanometer, "amp" means ampicillin; "LB" means Luria-Bertani broth or lysogeny broth; "FACS" means fluorescence activated cell sorter; "RFU" means relative fluorescence units, "wt" means wild type; and "cat#" means catalog number.

General Methods

Standard recombinant DNA and molecular cloning techniques used in the Examples are well known in the art and are described by Sambrook and Russell, (supra); Silhavy et al., (supra); and Ausubel et al., (supra).

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, DC., 1994, or in Brock (supra). All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.) or Sigma-Aldrich Chemical Company (St. Louis, Mo.), unless otherwise specified.

Example 1

Construction of Mutant araB Promoter Library

Typically, strong *E. coli* promoters share significantly more sequence homology with the consensus −35 and −10 regions of the strong *E. coli* promoters (in *Biochemistry*, Voet, D. & Voet. J. G., 1990, John Wiley & Sons, Inc., Hoboken, N.J., pp. 855-858; $1^{st}$ edition). The araB promoter is a medium strength promoter. Its −10 promoter sequence (TACTGT) is significantly different from the consensus −10 region (TATAAT) of stronger *E. coli* promoters. This difference is believed to lead to lower gene expression levels depending on the sequence context of the 5' end sequence of the gene. One strategy of improving the araB promoter strength is to change the −10 promoter sequence of araB into that of the consensus sequence. An alternative approach is to introduce randomization at the −10 promoter region, while keeping the −35 promoter region unchanged as it overlaps with the binding site of the transcriptional regulator AraC.

AraC is the transcriptional regulator for the araB promoter that activates transcription of araB gene in the presence of L-arabinose, and represses the transcription in the absence of L-arabinose (Guzman et al., *J Bacteriol.* 177(14):4121-4130 (1995) and U.S. Pat. No. 5,028,530 to Lai et al.). The araB promoter is also regulated by catabolite repression. In order to provide a reporter plasmid for the improvement selection of stronger araB mutant promoters, a reporter plasmid pBAD.GFP was constructed (FIG. 1; SEQ ID NO: 8). Green Fluorescent Protein (Aequorea coerulescens GFP; SEQ ID NO: 7) was used as a reporter gene product expressed from a plasmid in *E. coli*. The NcoI-EcoRI restriction fragment encoding for GFP gene (SEQ ID NO: 6) from plasmid pAcGFP (Clontech, Mountainview, Calif.) was subcloned into the NcoI and EcoRI sites of plasmid pBAD.HisB (Invitrogen, Carlsbad, Calif.; SEQ ID NO: 5) to yield plasmid pBAD.GFP (FIG. 1; SEQ ID NO: 8).

The *E. coli* strain TOP10 (Invitrogen, Carlsbad, Calif.) transformed with pBAD.GFP (strain DPD5146) was induced with 0.2% L-arabinose overnight in LB media with 100 µg/mL ampicillin, and an induction of fluorescence intensity was detected using the Perkin Elmer HTS7000Plus bioassay plate reader (Perkin Elmer, Boston, Mass.), with excitation wavelength at 485 nm and emission wavelength at 535 nm (pBAD.GFP(−)=no L-arabinose added (control); pBAD.GFP (+)−1=0.2% L-arabinose added at inoculation; and pBAD.GFP(+)−2=0.2% L-arabinose added at mid-log growth phase). The results are provided in Table 1.

TABLE 1

| Strain | Relative Fluorescence Units | Relative Fluorescence Units |
|---|---|---|
| pBAD.GFP(−) (control) | 653 | 857 |
| pBAD.GFP(+)-1 (early log phase) | 1552 | 1756 |
| pBAD.GFP(+)-2 (mid log phase) | 2419 | 2623 |

As expected for typical gene expression in *E. coli*, a higher level of GFP fluorescence was detected when the culture was induced at mid log growth phase vs. early log phase.

An araB promoter mutant library was constructed by synthesizing two complementary oligonucleotides encompassing the wild type araB promoter (SEQ ID NO: 1) sequence.

```
primer 1:
                                          (SEQ ID NO: 3)
5'-gatcctacctgacgcttttatcgcaactctcNNNNNNNttctccata cccgttttttgggctaacaggaggaattaaccatg-3' primer 2:
                                          (SEQ ID NO: 4)
5'-catggttaattcctcctgttagcccaaaaaacgggtatggagaaNNN NNNgagagttgcgataaaaagcgtcaggtag-3'.
```

"N" indicates randomized positions which are equal mixtures of G,A,T, and C nucleotides) The two oligonucleotides, when annealed, contain a BamHI overhang at the 5' end, and a NcoI site containing blunt end at the 3' end. This fragment can be ligated into pBAD.GFP plasmid (SEQ ID NO: 8) at the BamHI (upstream of araB promoter) and NcoI (at ATG start codon) sites. The blunt end at NcoI site generated additional diversity for varying the distance between ribosomal binding site (RBS) and the ATG start codon.

The ligation mixture for the araB promoter mutant library was used to carry out transformation. A Fluorescence Activated Cell Sorter (FACS) was used to identify and select clones with stronger fluorescence intensity. Increased fluorescence (i.e. amount of GFP produced) allowed the detection of araB promoter mutants characterized by their ability to improved protein production level by monitoring fluorescence.

Example 2

Transformation and Quality Control of the Library

The ligation mix of the library was transformed into electro-competent *E. coli* TOP10 cells (Invitrogen) and plated on LB/ampicillin plates (100 µg/mL). Approximately 20,000 colonies were obtained. In order to test whether mutations were actually introduced into the −10 region of the promoter, eight random constructs were selected for sequencing. The eight colonies were inoculated into 3 mL of LB-ampicillin broth (10 g/L bacto-tryptone, 5 g/L bacto-yeast extract, 10 g/L NaCl, 100 mg/L ampicillin; pH 7.0). Plasmid DNA was extracted with the Qiagen miniprep kit (Qiagen, Valencia, Calif.) and the DNA sequence was determined.

FIG. 2 shows that the −10 region of the 8 sequenced mutant promoter constructs (SEQ ID NOs: 9-16) from the library had different sequences (underlined region) in comparison to the wild type (wt) starting sequence. The −35 region of all the constructs remained wild type. About half the constructs had deletions around the ribosome binding site (RBS), which was expected based on the initial cloning strategy (Example 1).

The mixed library of 20,000 colonies were transferred from the LB/Amp plates and resuspended in LB/Ampicillin (100 µg/mL). Glycerol was added to 15% (v/v) and the cells frozen at −80° C.

Example 3

Use of a Fluorescence Activated Cell Sorter (FACS) to Identify Mutants with Increased Expression An aliquot of the library of mixed constructs was inoculated in LB/Amp (100 µg/mL), grown up to $OD_{600}$ of 0.3, and induced with 0.2% arabinose for about 4 hours. *E. coli* TOP10 cells comprising the wild type arabinose promoter sequence (SEQ ID NO: 1) in the pBAD.GFP vector were grown up in the same manner to serve as controls.

The cells were analyzed with a fluorescence activated cell sorter (FACS; FACSVantage™ SE system; BD Biosciences, San Jose, Calif.), using a 488 nm laser. The *E. coli* TOP10 cells served as a negative control and were used to set up the parameters of the FACS and to set the boundaries for the subsequent gating of the cells. Fluorescence was measured at an emitted wavelength of 530 nm (±15 nm). *E. coli* TOP cells not transformed to express GFP (i.e. no fluorescence) served as a negative control.

FACS measurement of the TOP10 cells expressing the GFP protein under the control of the wild type araB promoter (SEQ ID NO: 1) were measured after induction. The measured fluorescence from the wild type araB driven expression of GFP was used to set a baseline fluorescence to measure the effect of the araB promoter mutations on GFP production. Cells having an increased fluorescence relative to the cells expressing GFP from the wild type promoter were selected and isolated for sequence analysis (i.e. "positive" hits).

Approximately 96% of the cells from the mutant promoter library fell into the 'negative' gating region (no significant increase in fluorescence relative to the observed fluorescence of cells expressing the wild type araB promoter). Approximately 1.6% fell into the 'intermediate' gating (slight increase in fluorescence relative to the wild type araB driven GFP expression), and about 0.04% of cells into the 'positive' gating (significantly higher fluorescence measured).

Approximately 1.6 million cells were sorted into the 'intermediate' bin, and approximately 36,000 cells in the 'positive' bin. These two populations were grown up overnight in LB/Amp medium (100 µg/mL). An aliquot of each was used to start a new 3-mL culture in LB/Amp medium, grown to $OD_{600}$ of 0.3, and induced with 0.2% L-arabinose for 4 hours. After letting the GFP mature for about 8 hours, a second round of FACS analysis/sorting was performed.

Results from the Second Round of FACS Enrichment

Approximately 56,000 cells from gate 'P3' (i.e. the top 0.3% of fluorescing cells) were sorted. This population was grown up overnight on LB/Amp plates (100 µg/mL). Fifty (50) colonies were picked and grown up in 3-mL LB/Amp medium to $OD_{600}$ of 0.3 and induced with 0.2% L-arabinose for 4 hours. After letting the GFP mature for approximately 8 hours, the cells were checked for fluorescence under a fluorescence microscope. About 20% of the cells were markedly brighter than the rest.

Example 4

Sequence Analysis of Promoter Mutants

The sequence of each araB mutant from the 50 colonies picked in Example 3 were determined to identify the mutations that give rise to higher fluorescence of the cells due to higher levels of expressed GFP. The brightest fraction of cells, which consisted of about 20% of the population, all contained the same promoter mutation (Mutant "GFP-B1"; SEQ ID NO: 17). An additional three mutations were identified that yielded intermediate brightness, similar to cells with pBAD.GFP (denoted as mutants GFP-M1 (SEQ ID NO:18), GFP-M2 (SEQ ID NO: 19), and GFP-M3 (SEQ ID NO: 20)), as determined visually by fluorescence microscopy.

The sequence of mutant promoter GFP-B1 (a.k.a. "B1") was identical for all the very bright constructs that were identified. GFP-M1, GFP-M2, and GFP-M3 were only represented once in the samples that were sequenced (FIG. 3). The sequence shown in this alignment includes sequences upstream of the promoter region up to, but not including the ATG start codon of GFP. The coding sequence of GFP was wild type in all cases, ruling out the possibility that the increased fluorescence is due to a mutation in GFP itself.

Two main features become apparent from FIG. 3: (1) the −10 sequence is different in all constructs, and (2) there is an insertion of about 75 bases (bold type) after the RBS in constructs GFP-B1 and GFP-M3. This duplication has high sequence similarity to the region encompassing the promoter region and its flanking sequences.

Example 5

Fluorescence Assay of Mutant Clones GFP-B1 and GFP-M2

Two clones from the initial FACS experiment (Example 3) were selected for further analysis using a fluorescence plate reader (Perkin Elmer HTS7000Plus bioassay plate reader; PerkinElmer Life and Analytical Sciences, Waltham, Mass.). E. coli TOP10 cells transformed with pBAD.GFP (wt), pBAD.GFP-B1 and pBAD.GFP-M2 (comprising SEQ ID NO: 19) were grown in LB, 100 μg/mL ampicillin and induced at mid log growth phase by 0.2% L-arabinose overnight. Two hundred microliters of each cell culture was transferred to a 96-well plate in duplicates, and the fluorescence signal was measured at excitation wavelength at 485 nm and emission wavelength at 535 nm. The fluorescence intensity was normalized to $OD_{600}$ levels to 1 (measured absorbance in same instrument at 595 nm) (Table 2).

TABLE 2

| Clones | Relative Fluorescence Intensity (RFU) | | |
|---|---|---|---|
|  | LB | LB, 0.2% arabinose | LB, 0.2% glucose |
| Wild type | 230 | 827 | 162 |
| GFP-B1 | 232 | 9697 | 383 |
| GFP-M2 | 234 | 576 | 271 |

Results:

The clone comprising the GFP-B1 mutant araB promoter (SEQ ID NO: 17) was the brightest clone, its fluorescence intensity was about 10× higher compared to wild type (SEQ ID NO: 1) araB-GFP clone. The GFP expression in mutant GFP-B1 is low in the absence of arabinose, or in the presence of glucose. This indicates that GFP-B1 mutant is tightly controlled by arabinose, and is subjected to catabolite repression (similar to the tightly regulated expression control observed in wild type araB promoter). Another clone from the FACS selection, GFP-M2, did not show improved fluorescence when analyzed using a fluorescence plate reader. The increased fluorescence associated with the promoter activity of mutant araB promoter GFP-B1 was confirmed.

Example 6

N-Terminal Sequencing of the Protein Product

Analysis of the GFP-B1 promoter (SEQ ID NO: 17) sequence shows that there are two potential translational start sites, one being the start site of the wild type GFP protein, the other the first ATG after the RBS (see FIG. 6). The introduced ATG start codon is in frame with the second ATG start codon (the start codon in the coding region for the wild type GFP protein). In order to determine which one is used in the cell, the N-terminal sequence of the over expressed product was determined. The cells transformed with plasmid pBAD.GFP-B1 (B1) were grown up to $OD_{600}$ of 0.3 and induced for 3 hours. An aliquot was run on a NUPAGE® 4-12% Bis-Tris gel (Invitrogen) and transferred to a PVDF (polyvinylidene difluoride) membrane. The blot was stained with COO-MASSIE® Blue R-250 (Invitrogen), and the band of interest excised and submitted to N-terminal sequencing using Edman chemistry. The N-terminal sequence obtained (MVP-DAFYRNSL; SEQ ID NO: 21) corresponds to the first ATG codon (located right after the ribosomal biding site (RBS) and 5' to the wild type GFP start codon) being used. Thus, mutant araB promoter GFP-B1 (SEQ ID NO: 17) adds an additional 24 amino acids to the N-terminus of the over expressed protein.

Example 7

Analysis of the araB Mutant Promoter B1

In order to gain more insights into what features of the araB B1 mutant promoter are responsible for the increased production of GFP, the fluorescence of various mutant constructs was compared.

Figure 4:
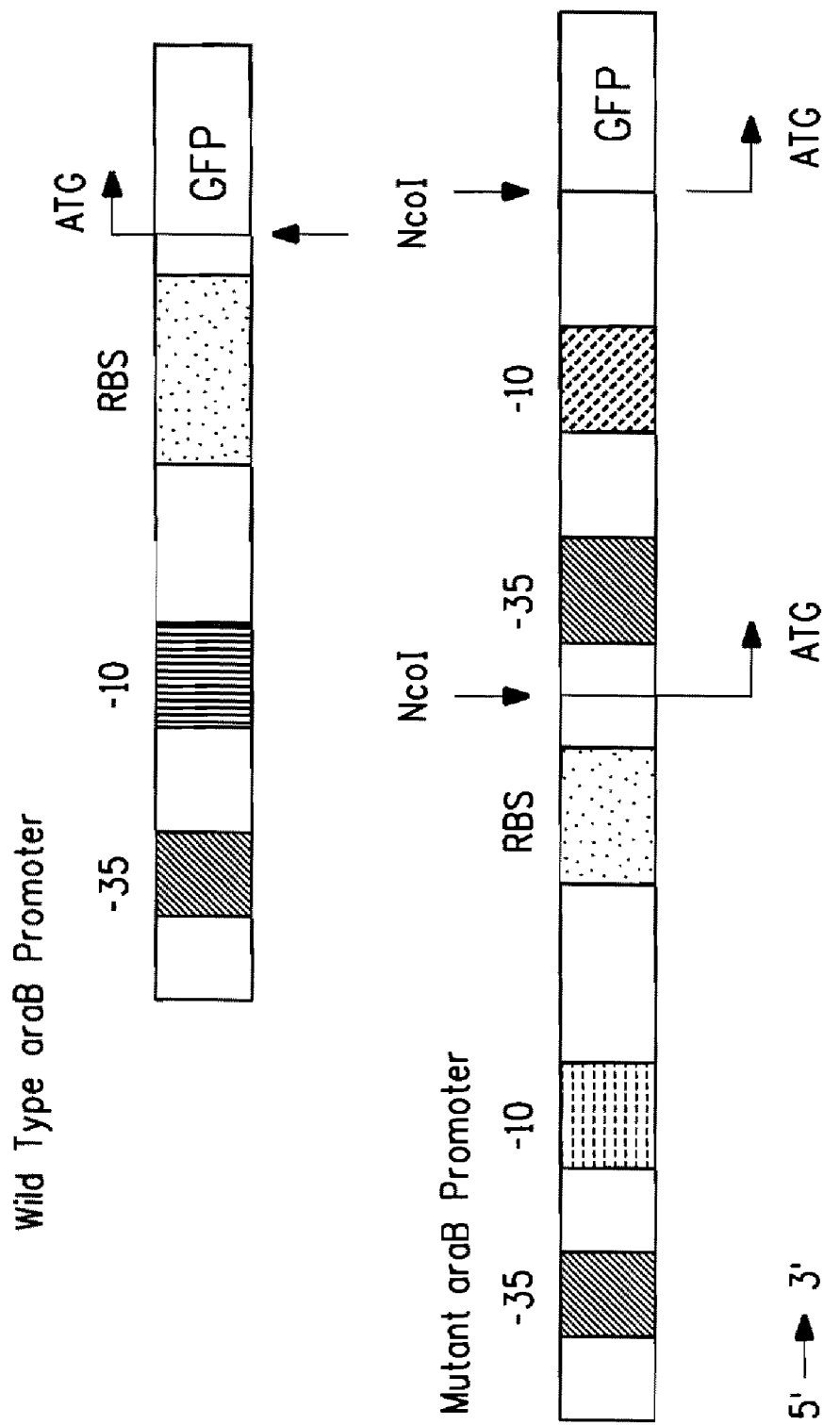
FIG. 4 is a comparative illustration of the various elements found in the araB wild type promoter and mutant araB promoter GFP B1 ("B1"). Regions within each promoter that correlate to sequences associated with proposed functional elements are labeled ("RBS"=ribosome binding site; "−10"=minus ten-like sequence; "−35"=minus thirty five-like sequence; "GFP"=coding region of the green fluorescent protein operably linked to the promoter including the location of the ATG start codon; and "NcoI"=NcoI restriction enzyme recognition sequence).

A comparison of the wild type araB promoter (SEQ ID NO: 1) versus the mutant araB B1 promoter of SEQ ID NO: 17 indicates that the mutant promoter comprises a general duplication of a promoter-like region as shown in FIG. 4. The sequence of the −10 region of the first promoter element is not identical to the sequence of the −10 region of the second promoter element in the mutant B1 promoter. No discernable ribosomal binding sequence could be identified in the duplicated motif of araB mutant promoter B1.

Example 8

Preparation of Various Additional Mutant Promoters Derived from the Wild-Type araB Promoter or the Mutant araB Promoter B1

Various additional mutant promoter sequences were prepared using primer pairs for targeted modification to either the wild type araB promoter or the mutant araB promoter B1 (Example 7). The following PCR conditions were used unless otherwise noted.

QuickChange PCR was used according to the manufacturer's instructions (Stratagene, La Jolla, Calif.)

| PCR Protocol: | |
|---|---|
| Temperature | Time |
| 95° C. | 30 sec |
| 95° C. | 30 sec |
| 55° C. | 10 min (repeated 17 times) |
| 68° C. | 10 min |
| 68° C. | 10 min |
| 4° C. | hold |

The products from the PCR reactions were gel purified. Constructs were transformed into *E. coli* TOP10 electrocompetent cells.

A. Preparation of Mutant araB Promoter by Removing the ATG Start Codon in Mutant B1

A derivative of mutant promoter B1 (SEQ ID NO: 17) was prepared by removing the ATG start codon so that a GFP fusion product was not formed. Using mutant araB promoter B1 (SEQ ID NO: 17) as a template, several sets of primers were used to prepare a modified version of mutant promoter B1 lacking the ATG start codon (ATG→ATC). (Table 3; mutant promoter Ara1b; "1b")

B. Preparation of Mutant Promoter ara4a by Replacing the First −10 Sequence of the Promoter by the −10 Wild Type Sequence A derivative of mutant promoter B1 was prepared by introducing the wild type −10 sequence into the first −10 hexamer of the mutant B1 sequence. This was achieved by cloning the NcoI fragment (about 100 nucleotides) of mutant promoter B1 into the wild type sequence, yielding sequence mutant promoter ara4a (SEQ ID NO: 23)

C. Preparation of Mutant Promoter ara5a by Replacing the NcoI Site that Contains the Start Codon of GFP, with an NdeI Site.

Using mutant araB promoter B1 (SEQ ID NO: 17) as a template, two primers were used to prepare a modified version of mutant promoter B1 by replacing the NcoI site that contains the start codon of GFP, with an NdeI site (Table 3; mutant promoter Ara5a; "5a").

D. Preparation of Mutant Promoter ara8a by Having Two Different −10 Regions Compared to Mutant B1.

Using mutant araB promoter GFP-M2 (SEQ ID NO: 19) as a template, two primers were used to prepare a modified version of mutant promoter B1 to result in a sequence that contains two different −10 sequences. (Table 3; mutant promoter Ara8a; "8a").

Summary of All the Constructs and Their Fluorescence:

All plasmid constructs were transformed into *E. coli* Top10. Cells were grown in 3 mL LB (+100 μg/mL Ampicillin) overnight. New 3-mL growths were grown to $OD_{600}$ of about 0.3, induced with 0.2% L-arabinose and grown for 4 hours. $OD_{600}$ and fluorescence were measured and values below represent fluorescent units per one OD equivalent of cells.

Measurement of fluorescence: Perkin Elmer HTS7000Plus bioassay plate reader, with excitation wavelength at 485 nm and emission wavelength at 535 nm. Subtracted background fluorescence and normalized OD levels to 1 (measured absorbance in same instrument at 595 nm).

Table 4 shows the fluorescence (Relative fluorescence units; RFU) of various araB mutant promoters vs. the wild type araB promoter control when operably linked to a GFP fluorescent reporter.

TABLE 4

GFP Fluorescence of Various Mutant Promoters vs. The Wild Type araB Promoter

| Promoter ID. | SEQ ID NO. | Measured Fluorescence[1,2] (RFU) | Percent Increase in Fluorescence vs. wild type[1] | Fold difference[1] |
|---|---|---|---|---|
| Wild type araB promoter | 1 | 366<br>500<br>344<br>Mean = 403<br>S.D. = 69 | NA | NA |
| B1 | 17 | 3166<br>3420<br>3692<br>Mean = 3426<br>S.D. = 215 | 750 | 8.5 |
| ara1B | 22 | 3741 | 829 | 9.3 |

TABLE 3

| Template Used | Primer Name | Primer Sequence (SEQ ID NO.) | Modification Introduced | Resulting Mutant Promoter (SEQ ID NO:) |
|---|---|---|---|---|
| Mutant B1 (SEQ ID NO: 17) | Ara1F | gaggaattaaccatcgta cctgacgc (SEQ ID NO: 40) | Change ATG to ACT in mutant B1 | Ara1b (SEQ ID NO: 22) |
| Mutant B1 (SEQ ID NO: 17) | Ara1R | gcgtcaggtacgatggtt aattcctc (SEQ ID NO: 41) | | |
| Mutant B1 (SEQ ID NO: 17) | Ara5F | ggctaacagaaatcatat ggtgagcaagggc (SEQ ID NO: 42) | Mutated NcoI to NdeI in construct | Ara5a (SEQ ID NO: 24) |
| Mutant B1 (SEQ ID NO: 17) | Ara5R | gcccttgctcaccatatga tttctgttagcc (SEQ ID NO: 43) | | |
| Mutant GFP-M2 (SEQ ID NO: 19) | Ara8F | ccatacccgttttttggcta acagaaataccatggtg agcaagggcgcc (SEQ ID NO: 44) | Put duplicated sequence back in frame. | Ara8a (SEQ ID NO: 25) |
| Mutant GFP-M2 (SEQ ID NO: 19) | Ara8R | ggcgcccttgctcaccat ggtatttctgttagccaaa aaacgggtatgg (SEQ ID NO: 45) | Results in same sequence as mutant B1, except for different −10 sequences. | |

TABLE 4-continued

GFP Fluorescence of Various Mutant Promoters vs. The Wild Type araB Promoter

| Promoter ID. | SEQ ID NO. | Measured Fluorescence[1,2] (RFU) | Percent Increase in Fluorescence vs. wild type[1] | Fold difference[1] |
|---|---|---|---|---|
| ara4A | 23 | 2846 | 620 | 7.2 |
|  |  | 2956 |  |  |
|  |  | Mean = 2901 |  |  |
|  |  | S.D. = 55 |  |  |
| ara5A | 24 | 2115 | 425 | 5.2 |
| ara8A | 25 | 8378 | 1980 | 21 |
| M2 | 19 | 369 | −0.25 | 1 |
|  |  | 434 |  |  |
|  |  | Mean = 402 |  |  |
|  |  | S.D. = 32.5 |  |  |

[1]= Mean value used for comparison to average value for wild type fluorescence. Fluorescence is proportional to the amount of GFP present.
[2]= normalized per 1 $OD_{600}$ of cells after subtracting out background.

A CLUSTALW sequence alignment (version 1.83) was performed using mutant araB promoters B1, ara1B, ara4A, ara5A, and ara8a to generate a consensus mutant araB promoter sequence (FIG. 5). The araB promoter consensus sequence is provided as SEQ ID NO: 2.

What is claimed is:

1. An isolated nucleic acid molecule encoding an araB promoter comprising a nucleic acid sequence SEQ ID NO: 2.

2. The isolated nucleic acid molecule of claim 1, further comprising an AraC transcription factor binding region operably linked to SEQ ID NO: 2.

3. The isolated nucleic acid molecule of claim 2, wherein the AraC transcription factor binding region comprises SEQ ID NO: 33.

4. An expression cassette comprising the isolated nucleic acid molecule of claim 2 operably linked to a coding region of interest.

5. An arabinose-inducible expression cassette comprising:
   a) an AraC transcription factor binding region;
   b) an araB promoter of SEQ ID NO: 2; and
   c) a coding region of interest;
   wherein the AraC transcription factor binding region, the araB promoter, and the coding region of interest are in operable linkage.

6. The expression cassette of any one of claim 4 or 5, wherein the coding region of interest encodes for a peptide comprising at least one body surface-binding peptide selected from the group consisting of hair-binding peptides, skin-binding peptides, nail-binding peptides, and teeth-binding peptides.

7. A vector comprising in operable linkage:
   a) an AraC transcription factor binding region;
   b) an araB promoter comprising a nucleic acid sequence SEQ ID NO: 2;
   b) a coding region of interest encoding a polypeptide of interest;
   wherein expression of the araB promoter is repressed in the absence of L-arabinose and induced in the presence of an effective amount of L-arabinose.

8. The vector of claim 7, further comprising at least one transcription terminator operably linked downstream to the coding region of interest.

9. The vector of claim 7, wherein the AraC transcription factor binding region comprises SEQ ID NO: 33.

10. The vector of claim 7, wherein the vector further comprises at least one expressible copy of an araC gene.

11. The vector of claim 7, wherein the coding region of interest encodes from a peptide comprising at least one body surface-binding peptide selected from the group consisting of hair-binding peptides, skin-binding peptides, nail-binding peptides, and teeth-binding peptides.

12. A microbial host cell comprising the vector of any one of claims 7 to 11.

13. The microbial host cell of claim 12, wherein the microbial host cell is AraC+.

14. The microbial host cell of claim 13, wherein the recombinant microbial host cell is a member of the genus *Escherichia*.

15. The microbial host cell of claim 14, wherein the recombinant microbial host cell is *Escherichia coli*.

16. A method of expressing a coding region of interest in a microbial host cell comprising;
   a) providing an AraC+ microbial host cell comprising a chimeric gene, said chimeric gene comprising the following nucleic acid molecules in operable linkage:
      i) an AraC transcription factor binding region;
      ii) an araB promoter of SEQ ID NO: 2; and
      iii) a coding region of interest encoding a desired gene product; and
   b) contact the microbial host cell of (a) with an effective amount of L-arabinose whereby the coding sequence of interest is expressed and the desired gene product is produced.

17. The method of claim 16, further comprising:
   c) isolating the desired gene product produced in step (b).

18. The method of claim 17, wherein the chimeric gene is expressed from an expression vector.

19. The method of claim 18, wherein the expression vector further comprises a transcription terminator operably linked to the coding region of interest.

20. The method of claim 19, wherein the transcription terminator comprises SEQ ID NO: 28.

21. The method of claim 16, wherein the coding region of interest encodes for a peptide comprising at least one body surface-binding peptide selected from the group consisting of hair-binding peptides, skin-binding peptides, nail-binding peptides, and teeth-binding peptides.

22. The method of claim 16, wherein the microbial host cell comprises an arabinose inducible operon comprising SEQ ID NO: 34.

* * * * *